(12) United States Patent
Feng et al.

(10) Patent No.: US 8,546,427 B2
(45) Date of Patent: *Oct. 1, 2013

(54) TETRAHYDROQUINOLINE DERIVATIVES

(75) Inventors: Lichun Feng, Shanghai (CN); Mengwei Huang, Shanghai (CN); Yongfu Liu, Shanghai (CN); Guolong Wu, Shanghai (CN); Mingwei Zhou, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/272,259

(22) Filed: Oct. 13, 2011

(65) Prior Publication Data

US 2012/0101127 A1    Apr. 26, 2012

(30) Foreign Application Priority Data

Oct. 20, 2010    (WO) ................ PCT/CN2010/077907

(51) Int. Cl.
*A61K 31/47*    (2006.01)
*C07D 215/00*    (2006.01)

(52) U.S. Cl.
USPC ............ 514/311; 546/112; 546/164; 514/299

(58) Field of Classification Search
USPC ................ 546/26, 112, 152, 164; 514/299, 514/311
See application file for complete search history.

(56) References Cited

U.S. PATENT DOCUMENTS 7,138,412 B2 *    11/2006    Quan et al. .................... 514/311
7,709,646 B2 *    5/2010    Quan et al. .................... 546/159

FOREIGN PATENT DOCUMENTS

WO    2004/080971    9/2004
WO    2011/128251    10/2011

OTHER PUBLICATIONS

Friedman et al., "Nature" 395:763-770 ( 1998).
Kadowaki et al., "The Journal of Clinical Investigation" 116:1784-1792 ( 2006).
Kobayashi et al., "Synthesis" 9(1):1195-1202 ( 1995).
Carling, D., "Trends in Biochem. Sci." 29:18-24 ( 2004).
Cool et al., "Cell Metabolism" 3:403-416 ( 2006).
Woods et al., "Molecular & Cellular Biology" 20:6704-6711 ( 2000).
Kahn et al., "Cell Metabolism" 1:15-25 ( 2005).
Minokoshi et al., "Nature" 415:339-343 ( 2002).
Zhou et al., "The Journal of Clinical Investigation" 108:1167-1174 (2001).
Fryer et al., "The Journal of Biological Chemistry" 277:25226-25232 (2002).
El-Mir et al., "The Journal of Biological Chemistry" 275:223-228 (2000).
Shaw et al., "Science (New York) NY" 310:1642-1646 ( 2005).
Muoio et al., "Diabetes" 46:1360-1363 ( 1997).
Hardie, D. G., "Annual Review of Pharmacology & Toxicology" 47:185-210 ( 2007).
Pang et al., "The Journal of Biological Chemistry" 283:16051-16060 (2008).
Owen et al., "The Biochemical Journal" 348:607-614 ( 2000).
Hardie et al., "Nature Reviews Molecular Cell Biology" 8:774-785 (2007).
Semple et al., "The Journal of Clinical Investigation" 116:581-589 (2006).
Long et al., "The Journal of Clinical Investigation" 116:1776-1783 (2006).
Yamauchi et al., "Nature Medicine" 7:941-946 ( 2001).
"International Search Report PCT/EP2011/068053 mailed Nov. 21, 2011".
Yamauchi et al., "Nature Medicine" 8:1288-1295 ( 2002).

* cited by examiner

*Primary Examiner* — Golam M M Shameem

(57) ABSTRACT

The present invention relates to compounds according to formula (I)

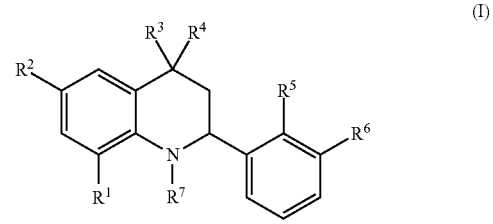

and pharmaceutically acceptable salts or esters thereof, wherein $R^1$ to $R^7$ have the significance given herein. The compounds are activators of AMP-activated protein kinase (AMPK) and are useful in the treatment or prophylaxis of diseases that are related to AMPK regulation, such as obesity, dyslipidemia, hyperglycemia, type 1 or type 2 diabetes and cancers.

24 Claims, No Drawings

TETRAHYDROQUINOLINE DERIVATIVES

PRIORITY TO RELATED APPLICATIONS

This application claims the benefit of European Patent Application No. PCT/CN2010/077907, filed Oct. 20, 2010, which is hereby incorporated by reference in its entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes and cancers.

BACKGROUND OF THE INVENTION

Obesity and type 2 diabetes, hypertension and cardiovascular disease are diseases that feature serious disturbances in glucose or lipid metabolism that severely affect the health and quality of life of affected individuals. In addition, cancer metabolism is known to be different from normal cellular metabolism. The increasing prevalence of these diseases makes finding new drug targets for treating these syndromes an urgent task.

AMP-activated protein kinase acts as a cellular energy sensor and regulator. It is activated by an increase in the cellular AMP:ATP ratio induced by metabolic stress, hormone and nutrient signals and other cellular mechanisms such as phosphorylation and protein-protein interaction. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. *Nature reviews* 8 (2007b), 774-785; Woods, A et al. *Molecular and cellular biology* 20 (2000), 6704-6711). The growing evidence of AMPK regulatory effects on glucose and lipid metabolism makes it a potential drug target for treatment of diabetes, metabolic syndrome and cancer (Carling, D. *Trends Biochem Sci* 29 (2004), 18-24; Hardie, D G. *Annual review of pharmacology and toxicology* 47 (2007a), 185-210; Kahn, B B et al. *Cell metabolism* 1 (2005), 15-25; Long, Y C et al. *The Journal of clinical investigation* 116 (2006), 1776-1783).

At the physiological level, this concept has been supported by two adipokines, leptin and adiponectin, both of which exert excellent effects on glucose and lipid metabolism (Friedman, J M and Halaas, J L. *Nature* 395 (1998), 763-770; Muoio, D M et al. *Diabetes* 46 (1997), 1360-1363; Yamauchi, T et al. *Nature medicine* 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. *Nature* 415 (2002), 339-343). Adiponectin stimulates glucose uptake and fatty acid oxidation in vitro by activation of AMPK. Furthermore, it exerts its hypoglycemic effect by decreasing PEPCK and G6Pase expression, whereas the administration of dominant negative α1 adenovirus reverses the effect in vivo (Yamauchi, T et al. *Nature medicine* 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. *The Journal of clinical investigation* 116 (2006), 581-589). Recent findings indicate that AMPK may be involved in the antidiabetic effects of rosiglitazone (Brunmair, B et al. *The Journal of biological chemistry* 277 (2002), 25226-25232; Kadowaki, T et al. *The Journal of clinical investigation* 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. *The Journal of biological chemistry* 275 (2000), 223-228; Owen, M R et al. *The Biochemical journal* 348 Pt 3 (2000), 607-614; Zhou, G et al. *The Journal of clinical investigation* 108 (2001), 1167-1174), and the hypoglycemic effect could be blocked completely by knockout of its upstream kinase LKB1, confirming the key role of AMPK in mediating the antidiabetic effect of metformin (Shaw, R J et al. *Science* (New York) N.Y. 310 (2005), 1642-1646).

Most recently, Cool and coworkers have identified a small direct AMPK activator, A-769662, which exerts antidiabetic effects in vivo (Cool, B et al. *Cell metabolism* 3 (2006), 403-416). Li's laboratory has also identified a small AMPK activator, PT1, which activates the inactive forms of AMPK α2$_{398}$ and α1$_{394}$ with micromolar activity and exerts some cellular effects (Pang, T et al. *The Journal of biological chemistry* 283 (2008), 16051-16060).

It has been found that the compounds of the present invention are potent AMPK activators. The compounds of the invention are therefore useful in the treatment or prophylaxis of diseases that are related to AMPK regulation, such as obesity, dyslipidemia, hyperglycemia, type 1 or type 2 diabetes and cancers.

SUMMARY OF THE INVENTION

The invention relates in particular to a compound of formula (I)

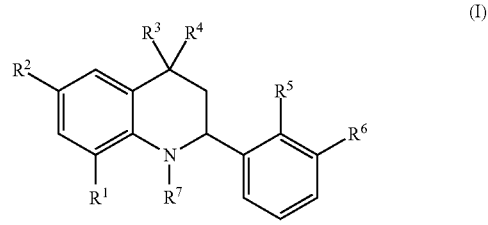

wherein
$R^1$ is selected from the group consisting of hydrogen, alkyl, haloalkyl, halogen, cyano and carboxy;
$R^2$ is selected from the group consisting of hydrogen, alkyl, haloalkyl, halogen, cyano and carboxy;
$R^3$ and $R^4$ are independently alkyl;
$R^5$ and $R^6$ are independently selected from the group consisting of hydrogen, carboxyalkylamino, carboxycycloalkylamino, alkylsulfonylamino, phenylsulfonylamino, halophenylsulfonylamino, alkylphenylsulfonylamino, phenylcarbonylamino, halophenylcarbonylamino, pyridinylsulfonylamino, alkylaminosulfonyl and halophenylaminosulfonyl;

provided that $R^5$ and $R^6$ are not both hydrogen at the same time; and $R^7$ is hydrogen or alkyl;

or a pharmaceutically acceptable salt or ester thereof.

The present invention also relates to a pharmaceutical composition comprising a compound as described above and a therapeutically inert carrier.

The invention further relates to a process for the manufacture of these novel compounds and medicaments containing them. The compounds of the invention have activation effect on AMP (adenosine monophosphate)-activated protein kinase, which results in lowered blood glucose and lipid levels. The invention thus also concerns the use of such compounds for the treatment or prophylaxis of diseases that are related to AMPK regulation, such as obesity, dyslipidemia, hyperglycemia, type 1 or type 2 diabetes, and cancers.

DETAILED DESCRIPTION OF THE INVENTION

As used herein, the term "alkyl", alone or in combination, signifies a saturated, linear or branched chain alkyl group containing 1 to 8, preferably 1 to 6, more preferably 1 to 4 carbon atoms, for example methyl, ethyl, propyl, isopropyl, 1-butyl, 2-butyl and tert-butyl. Preferred alkyl groups are methyl, ethyl, isopropyl and tert-butyl.

The term "cycloalkyl", alone or in combination, refers to a saturated carbon ring containing from 3 to 7 carbon atoms, preferably from 3 to 6 carbon atoms, for example, cyclopropyl, cyclobutyl, cyclopentyl, cyclohexyl, cycloheptyl. Preferred cycloalkyl groups are cyclopropyl, cyclopentyl and cyclohexyl.

The term "halogen" means fluorine, chlorine, bromine or iodine. Halogen is preferably fluorine, chlorine or bromine.

The term "haloalkyl" means alkyl substituted by one to seven halogens, preferably one to three halogens, preferably fluorine. A preferred haloalkyl is trifluoromethyl.

The term "halophenyl" means phenyl substituted by halogen.

The term "carboxy", alone or in combination, refers to the group —COOH.

The term "carbonyl", alone or in combination, refers to the group —C(O)—.

The term "amino", alone or in combination, refers to primary (—NH$_2$—), secondary (—NH—) or tertiary amino (—N—).

The term "sulfonyl", alone or in combination, refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al. organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred is the sodium salt of the compound of formula (I).

"Pharmaceutically acceptable ester" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

The invention relates in particular to a compound of formula (I)

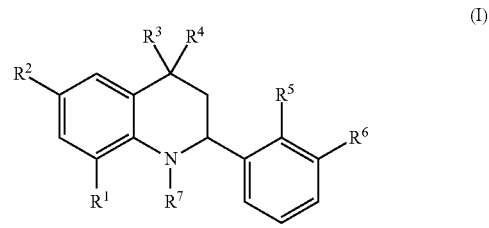

wherein $R^1$ is selected from the group consisting of hydrogen, alkyl, haloalkyl, halogen, cyano and carboxy;

$R^2$ is selected from the group consisting of hydrogen, alkyl, haloalkyl, halogen, cyano and carboxy;

$R^3$ and $R^4$ are independently alkyl;

$R^5$ and $R^6$ are independently selected from the group consisting of hydrogen, carboxyalkylamino, carboxycycloalkylamino, alkylsulfonylamino, phenylsulfonylamino, halophenylsulfonylamino, alkylphenylsulfonylamino, phenylcarbonylamino, halophenylcarbonylamino, pyridinylsulfonylamino, alkylaminosulfonyl and halophenylaminosulfonyl;

provided that $R^5$ and $R^6$ are not both hydrogen at the same time; and $R^7$ is hydrogen or alkyl;

or a pharmaceutically acceptable salt or ester thereof.

The invention relates in particular to a compound of formula (I) wherein $R^1$ and $R^2$ are not both hydrogen at the same time.

In a particular embodiment of the invention, $R^1$ is selected from the group consisting of hydrogen, alkyl, halogen and carboxy.

In another particular embodiment of the invention, $R^1$ is selected from the group consisting of hydrogen, methyl and chloro.

Still in a particular embodiment of the invention, $R^2$ is selected from the group consisting of haloalkyl, halogen, cyano and carboxy.

In a further embodiment of the invention, $R^2$ is selected from the group consisting of trifluoromethyl, chloro, cyano and carboxy.

In another particular embodiment of the invention, $R^3$ and $R^4$ are both methyl at the same time.

The invention relates in particular to a compound of formula (I) wherein $R^5$ is selected from the group consisting of hydrogen, alkylsulfonylamino, halophenylsulfonylamino, carboxyalkylamino, carboxycycloalkylamino, halophenylcarbonylamino, pyridinylsulfonylamino and phenylsulfonylamino.

In particular, the invention relates also to a compound of formula (I) wherein $R^5$ is selected from the group consisting of hydrogen, carboxyalkylamino, halophenylsulfonylamino, pyridinylsulfonylamino and phenylsulfonylamino.

The invention relates also to a compound of formula (I) wherein $R^5$ is selected from the group consisting of hydrogen, carboxyisopropylamino, phenylsulfonylamino, fluorophenylsulfonylamino and pyridinylsulfonylamino.

The invention further relates to a compound of formula (I) wherein $R^6$ is selected from the group consisting of hydrogen, carboxyalkylamino, carboxycycloalkylamino, alkylsulfonylamino, phenylsulfonylamino, halophenylsulfonylamino, alkylphenylsulfonylamino, halophenylaminosulfonyl, pyridinylsulfonylamino and alkylaminosulfonyl.

In a further embodiment of this invention, $R^6$ is selected from the group consisting of hydrogen, carboxyalkylamino and carboxycycloalkylamino.

In another embodiment of the invention, $R^6$ is selected from the group consisting of hydrogen, carboxyisopropylamino and carboxycyclopropylamino.

The invention relates also in particular to a compound of formula (I) wherein $R^7$ is hydrogen or methyl.

Particular compounds of formula (I) according to the invention can be selected from the group consisting of 2-[3-(6-Chloro-4,4-dimethyl-1,2,3,4-tetrahydro-quinolin-2-yl)-phenylamino]-2-methyl-propionic acid;
1-[3-(6-Chloro-4,4-dimethyl-1,2,3,4-tetrahydro-quinolin-2-yl)-phenylamino]-cyclopropanecarboxylic acid;
2-[3-(6-Cyano-4,4-dimethyl-1,2,3,4-tetrahydro-quinolin-2-yl)-phenylamino]-2-methyl-propionic acid;
1-[3-(6-Cyano-4,4-dimethyl-1,2,3,4-tetrahydro-quinolin-2-yl)-phenylamino]-cyclopropanecarboxylic acid;
2-[3-(1-Carboxy-cyclopropylamino)-phenyl]-4,4-dimethyl-1,2,3,4-tetrahydro-quinoline-8-carboxylic acid;
2-[3-(1-Carboxy-cyclopropylamino)-phenyl]-6-chloro-4,4-dimethyl-1,2,3,4-tetrahydro-quinoline-8-carboxylic acid;
2-[3-(1-Carboxy-cyclopropylamino)-phenyl]-6-chloro-4,4-dimethyl-1,2,3,4-tetrahydro-quinoline-8-carboxylic acid;
1-[3-(6-Cyano-4,4,8-trimethyl-1,2,3,4-tetrahydro-quinolin-2-yl)-phenylamino]-cyclopropanecarboxylic acid;
2-[3-(4,4-Dimethyl-6-trifluoromethyl-1,2,3,4-tetrahydro-quinolin-2-yl)-phenylamino]-2-methyl-propionic acid;
N-[2-(6-Chloro-4,4-dimethyl-1,2,3,4-tetrahydro-quinolin-2-yl)-phenyl]-methanesulfonamide;
2-Methyl-2-[3-(1,4,4-trimethyl-6-trifluoromethyl-1,2,3,4-tetrahydro-quinolin-2-yl)-phenylamino]-propionic acid;
2-[3-(6-Cyano-4,4,8-trimethyl-1,2,3,4-tetrahydro-quinolin-2-yl)-phenylamino]-2-methyl-propionic acid;
1-[3-(1,4,4-Trimethyl-6-trifluoromethyl-1,2,3,4-tetrahydro-quinolin-2-yl)-phenylamino]-cyclopropanecarboxylic acid;
N-[2-(6-Chloro-4,4-dimethyl-1,2,3,4-tetrahydro-quinolin-2-yl)-phenyl]-3-fluoro-benzenesulfonamide;
2-[3-(1-Carboxy-1-methyl-ethylamino)-phenyl]-4,4-dimethyl-1,2,3,4-tetrahydro-quinoline-8-carboxylic acid;
Ethanesulfonic acid [2-(6-chloro-4,4-dimethyl-1,2,3,4-tetrahydro-quinolin-2-yl)-phenyl]-amide;
1-[3-(4,4-Dimethyl-6-trifluoromethyl-1,2,3,4-tetrahydro-quinolin-2-yl)-phenylamino]-cyclopropanecarboxylic acid;
1-[3-(8-Chloro-6-cyano-4,4-dimethyl-1,2,3,4-tetrahydro-quinolin-2-yl)-phenylamino]-cyclopropanecarboxylic acid;
N-[2-(6-Chloro-4,4-dimethyl-1,2,3,4-tetrahydro-quinolin-2-yl)-phenyl]-4-fluoro-benzenesulfonamide;
2-[2-(6-Cyano-4,4-dimethyl-1,2,3,4-tetrahydro-quinolin-2-yl)-phenylamino]-2-methyl-propionic acid;
N-[2-(6-Chloro-4,4-dimethyl-1,2,3,4-tetrahydro-quinolin-2-yl)-phenyl]-2-fluoro-benzenesulfonamide;
1-[2-(6-Chloro-4,4-dimethyl-1,2,3,4-tetrahydro-quinolin-2-yl)-phenylamino]-cyclopropanecarboxylic acid;
N-[2-(6-Cyano-4,4-dimethyl-1,2,3,4-tetrahydro-quinolin-2-yl)-phenyl]-methanesulfonamide;
2-[3-(6-Cyano-1,4,4-trimethyl-1,2,3,4-tetrahydro-quinolin-2-yl)-phenylamino]-2-methyl-propionic acid;
1-[2-(6-Cyano-4,4-dimethyl-1,2,3,4-tetrahydro-quinolin-2-yl)-phenylamino]-cyclopropanecarboxylic acid;
2-[2-(6-Chloro-4,4-dimethyl-1,2,3,4-tetrahydro-quinolin-2-yl)-phenylamino]-2-methyl-propionic acid;
1-[3-(6-Fluoro-4,4,8-trimethyl-1,2,3,4-tetrahydro-quinolin-2-yl)-phenylamino]-cyclopropanecarboxylic acid;
1-[3-(6-Cyano-1,4,4-trimethyl-1,2,3,4-tetrahydro-quinolin-2-yl)-phenylamino]-cyclopropanecarboxylic acid;
2-[3-(8-Chloro-6-cyano-4,4-dimethyl-1,2,3,4-tetrahydro-quinolin-2-yl)-phenylamino]-2-methyl-propionic acid;
2-Methyl-2-[3-(4,4,6-trimethyl-1,2,3,4-tetrahydro-quinolin-2-yl)-phenylamino]-propionic acid;
2-[3-(6-Fluoro-4,4,8-trimethyl-1,2,3,4-tetrahydro-quinolin-2-yl)-phenylamino]-2-methyl-propionic acid;
2-[2-(4-Fluoro-benzoylamino)-phenyl]-4,4-dimethyl-1,2,3,4-tetrahydro-quinoline-6-carboxylic acid;
2-(2-Ethanesulfonylamino-phenyl)-4,4-dimethyl-1,2,3,4-tetrahydro-quinoline-6-carboxylic acid;
4,4-Dimethyl-2-[2-(pyridine-3-sulfonylamino)-phenyl]-1,2,3,4-tetrahydro-quinoline-6-carboxylic acid;
2-[2-(2-Fluoro-benzoylamino)-phenyl]-4,4-dimethyl-1,2,3,4-tetrahydro-quinoline-6-carboxylic acid;
Pyridine-3-sulfonic acid [2-(6-chloro-4,4-dimethyl-1,2,3,4-tetrahydro-quinolin-2-yl)-phenyl]-amide;
2-[2-(3-Fluoro-benzoylamino)-phenyl]-4,4-dimethyl-1,2,3,4-tetrahydro-quinoline-6-carboxylic acid;
N-[2-(6-Chloro-4,4-dimethyl-1,2,3,4-tetrahydro-quinolin-2-yl)-phenyl]-benzenesulfonamide;
2-[2-(2-Fluoro-benzenesulfonylamino)-phenyl]-4,4-dimethyl-1,2,3,4-tetrahydro-quinoline-6-carboxylic acid;
2-[2-(4-Fluoro-benzenesulfonylamino)-phenyl]-4,4-dimethyl-1,2,3,4-tetrahydro-quinoline-6-carboxylic acid;
2-(2-Benzenesulfonylamino-phenyl)-4,4-dimethyl-1,2,3,4-tetrahydro-quinoline-6-carboxylic acid;
2-[2-(3-Fluoro-benzenesulfonylamino)-phenyl]-4,4-dimethyl-1,2,3,4-tetrahydro-quinoline-6-carboxylic acid;
N-[2-(4,4-Dimethyl-6-trifluoromethyl-1,2,3,4-tetrahydro-quinolin-2-yl)-phenyl]-3-fluoro-benzenesulfonamide;
N-[2-(4,4-Dimethyl-6-trifluoromethyl-1,2,3,4-tetrahydro-quinolin-2-yl)-phenyl]-2-fluoro-benzenesulfonamide;
N-[2-(4,4-Dimethyl-6-trifluoromethyl-1,2,3,4-tetrahydro-quinolin-2-yl)-phenyl]-4-fluoro-benzenesulfonamide;
Ethanesulfonic acid [2-(4,4-dimethyl-6-trifluoromethyl-1,2,3,4-tetrahydro-quinolin-2-yl)-phenyl]-amide;
N-[2-(4,4-Dimethyl-6-trifluoromethyl-1,2,3,4-tetrahydro-quinolin-2-yl)-phenyl]-benzenesulfonamide;
N-[2-(4,4-Dimethyl-6-trifluoromethyl-1,2,3,4-tetrahydro-quinolin-2-yl)-phenyl]-methanesulfonamide;
N-[2-(6-Cyano-4,4-dimethyl-1,2,3,4-tetrahydro-quinolin-2-yl)-phenyl]-benzenesulfonamide;
Propane-2-sulfonic acid [2-(6-cyano-4,4-dimethyl-1,2,3,4-tetrahydro-quinolin-2-yl)-phenyl]-amide;
N-[2-(4,4,6-Trimethyl-1,2,3,4-tetrahydro-quinolin-2-yl)-phenyl]-benzene sulfonamide;

3-Fluoro-N-[2-(4,4,6-trimethyl-1,2,3,4-tetrahydro-quinolin-2-yl)-phenyl]-benzenesulfonamide;
N-[2-(4,4,6-Trimethyl-1,2,3,4-tetrahydro-quinolin-2-yl)-phenyl]-methanesulfonamide;
Pyridine-3-sulfonic acid [2-(6-cyano-4,4-dimethyl-1,2,3,4-tetrahydro-quinolin-2-yl)-phenyl]-amide;
Pyridine-3-sulfonic acid [2-(4,4-dimethyl-6-trifluoromethyl-1,2,3,4-tetrahydro-quinolin-2-yl)-phenyl]-amide;
Ethanesulfonic acid [3-(4,4-dimethyl-6-trifluoromethyl-1,2,3,4-tetrahydro-quinolin-2-yl)-phenyl]-amide;
N-[3-(4,4-Dimethyl-6-trifluoromethyl-1,2,3,4-tetrahydro-quinolin-2-yl)-phenyl]-benzenesulfonamide;
N-[3-(4,4-Dimethyl-6-trifluoromethyl-1,2,3,4-tetrahydro-quinolin-2-yl)-phenyl]-4-fluoro-benzenesulfonamide;
N-[3-(4,4-Dimethyl-6-trifluoromethyl-1,2,3,4-tetrahydro-quinolin-2-yl)-phenyl]-methanesulfonamide;
N-[3-(4,4-Dimethyl-6-trifluoromethyl-1,2,3,4-tetrahydro-quinolin-2-yl)-phenyl]-2-fluoro-benzenesulfonamide;
N-[3-(4,4-Dimethyl-6-trifluoromethyl-1,2,3,4-tetrahydro-quinolin-2-yl)-phenyl]-3-fluoro-benzenesulfonamide;
Propane-2-sulfonic acid [3-(4,4-dimethyl-6-trifluoromethyl-1,2,3,4-tetrahydro-quinolin-2-yl)-phenyl]-amide;
N-[3-(4,4-Dimethyl-6-trifluoromethyl-1,2,3,4-tetrahydro-quinolin-2-yl)-phenyl]-4-methyl-benzenesulfonamide;
Pyridine-3-sulfonic acid [3-(4,4-dimethyl-6-trifluoromethyl-1,2,3,4-tetrahydro-quinolin-2-yl)-phenyl]-amide;
4-Fluoro-N-[3-(4,4,6-trimethyl-1,2,3,4-tetrahydro-quinolin-2-yl)-phenyl]-benzenesulfonamide;
2-Fluoro-N-[3-(4,4,6-trimethyl-1,2,3,4-tetrahydro-quinolin-2-yl)-phenyl]-benzenesulfonamide;
3-Fluoro-N-[3-(4,4,6-trimethyl-1,2,3,4-tetrahydro-quinolin-2-yl)-phenyl]-benzenesulfonamide;
N-[3-(4,4,6-Trimethyl-1,2,3,4-tetrahydro-quinolin-2-yl)-phenyl]-benzenesulfonamide;
4-Methyl-N-[3-(4,4,6-trimethyl-1,2,3,4-tetrahydro-quinolin-2-yl)-phenyl]-benzenesulfonamide;
N-[3-(4,4,6-Trimethyl-1,2,3,4-tetrahydro-quinolin-2-yl)-phenyl]-methanesulfonamide;
Ethanesulfonic acid [3-(4,4,6-trimethyl-1,2,3,4-tetrahydro-quinolin-2-yl)-phenyl]-amide;
Pyridine-3-sulfonic acid [3-(4,4,6-trimethyl-1,2,3,4-tetrahydro-quinolin-2-yl)-phenyl]-amide;
N-[3-(6-Cyano-4,4-dimethyl-1,2,3,4-tetrahydro-quinolin-2-yl)-phenyl]-2-fluoro-benzenesulfonamide;
N-[3-(6-Cyano-4,4-dimethyl-1,2,3,4-tetrahydro-quinolin-2-yl)-phenyl]-3-fluoro-benzenesulfonamide;
N-[3-(6-Cyano-4,4-dimethyl-1,2,3,4-tetrahydro-quinolin-2-yl)-phenyl]-4-fluoro-benzenesulfonamide;
N-[3-(6-Cyano-4,4-dimethyl-1,2,3,4-tetrahydro-quinolin-2-yl)-phenyl]-benzenesulfonamide;
N-[3-(6-Cyano-4,4-dimethyl-1,2,3,4-tetrahydro-quinolin-2-yl)-phenyl]-methanesulfonamide;
Ethanesulfonic acid [3-(6-cyano-4,4-dimethyl-1,2,3,4-tetrahydro-quinolin-2-yl)-phenyl]-amide;
Propane-2-sulfonic acid [3-(6-cyano-4,4-dimethyl-1,2,3,4-tetrahydro-quinolin-2-yl)-phenyl]-amide;
N-[3-(6-Cyano-4,4-dimethyl-1,2,3,4-tetrahydro-quinolin-2-yl)-phenyl]-4-methyl-benzenesulfonamide;
Pyridine-3-sulfonic acid [3-(6-cyano-4,4-dimethyl-1,2,3,4-tetrahydro-quinolin-2-yl)-phenyl]-amide;
N-[3-(6-Chloro-4,4-dimethyl-1,2,3,4-tetrahydro-quinolin-2-yl)-phenyl]-4-fluoro-benzenesulfonamide;
N-[3-(6-Chloro-4,4-dimethyl-1,2,3,4-tetrahydro-quinolin-2-yl)-phenyl]-2-fluoro-benzenesulfonamide;
N-[3-(6-Chloro-4,4-dimethyl-1,2,3,4-tetrahydro-quinolin-2-yl)-phenyl]-4-methyl-benzenesulfonamide;
N-[3-(6-Chloro-4,4-dimethyl-1,2,3,4-tetrahydro-quinolin-2-yl)-phenyl]-benzenesulfonamide;
N-[3-(6-Chloro-4,4-dimethyl-1,2,3,4-tetrahydro-quinolin-2-yl)-phenyl]-3-fluoro-benzenesulfonamide;
N-[3-(6-Chloro-4,4-dimethyl-1,2,3,4-tetrahydro-quinolin-2-yl)-phenyl]-methane sulfonamide;
3-(6-Chloro-4,4-dimethyl-1,2,3,4-tetrahydro-quinolin-2-yl)-N-methyl-benzenesulfonamide;
Ethanesulfonic acid [3-(6-chloro-4,4-dimethyl-1,2,3,4-tetrahydro-quinolin-2-yl)-phenyl]-amide;
3-(6-Chloro-4,4-dimethyl-1,2,3,4-tetrahydro-quinolin-2-yl)-N-(4-fluoro-phenyl)-benzenesulfonamide; and
Pyridine-3-sulfonic acid [3-(6-chloro-4,4-dimethyl-1,2,3,4-tetrahydro-quinolin-2-yl)-phenyl]-amide.

Further particular compounds of formula (I) can be selected from the group consisting of
2-[3-(6-Chloro-4,4-dimethyl-1,2,3,4-tetrahydro-quinolin-2-yl)-phenylamino]-2-methyl-propionic acid;
1-[3-(6-Chloro-4,4-dimethyl-1,2,3,4-tetrahydro-quinolin-2-yl)-phenylamino]-cyclopropanecarboxylic acid;
2-[3-(6-Cyano-4,4-dimethyl-1,2,3,4-tetrahydro-quinolin-2-yl)-phenylamino]-2-methyl-propionic acid;
2-Methyl-2-[3-(1,4,4-trimethyl-6-trifluoromethyl-1,2,3,4-tetrahydro-quinolin-2-yl)-phenylamino]-propionic acid;
2-[3-(6-Cyano-4,4,8-trimethyl-1,2,3,4-tetrahydro-quinolin-2-yl)-phenylamino]-2-methyl-propionic acid;
2-[2-(6-Cyano-4,4-dimethyl-1,2,3,4-tetrahydro-quinolin-2-yl)-phenylamino]-2-methyl-propionic acid;
N-[2-(6-Chloro-4,4-dimethyl-1,2,3,4-tetrahydro-quinolin-2-yl)-phenyl]-2-fluoro-benzenesulfonamide;
2-[3-(6-Cyano-1,4,4-trimethyl-1,2,3,4-tetrahydro-quinolin-2-yl)-phenylamino]-2-methyl-propionic acid;
1-[3-(6-Cyano-1,4,4-trimethyl-1,2,3,4-tetrahydro-quinolin-2-yl)-phenylamino]-cyclopropanecarboxylic acid;
2-[3-(8-Chloro-6-cyano-4,4-dimethyl-1,2,3,4-tetrahydro-quinolin-2-yl)-phenylamino]-2-methyl-propionic acid;
4,4-Dimethyl-2-[2-(pyridine-3-sulfonylamino)-phenyl]-1,2,3,4-tetrahydro-quinoline-6-carboxylic acid;
2-[2-(2-Fluoro-benzenesulfonylamino)-phenyl]-4,4-dimethyl-1,2,3,4-tetrahydro-quinoline-6-carboxylic acid;
2-[2-(4-Fluoro-benzenesulfonylamino)-phenyl]-4,4-dimethyl-1,2,3,4-tetrahydro-quinoline-6-carboxylic acid;
2-(2-Benzenesulfonylamino-phenyl)-4,4-dimethyl-1,2,3,4-tetrahydro-quinoline-6-carboxylic acid; and
2-[2-(3-Fluoro-benzenesulfonylamino)-phenyl]-4,4-dimethyl-1,2,3,4-tetrahydro-quinoline-6-carboxylic acid.

The compounds of the present invention can be prepared by any conventional means. Suitable processes for synthesizing these compounds are provided in the schemes below and in the examples. In the following schemes, $R^1$ to $R^7$ are as defined above unless otherwise indicated.

Abbreviations:
d: day or days
g: gram
h: hour or hours
HPLC: high performance liquid chromatography
Hz: hertz
mg: milligram
min: minute or minutes
mL: milliliter
mmol: millimole
mM: millimole per liter
LC/MS: liquid chromatography mass spectroscopy
MS: mass spectroscopy
ESI: electron spray ionization
APCI: Atmospheric pressure chemical ionization

Scheme 1

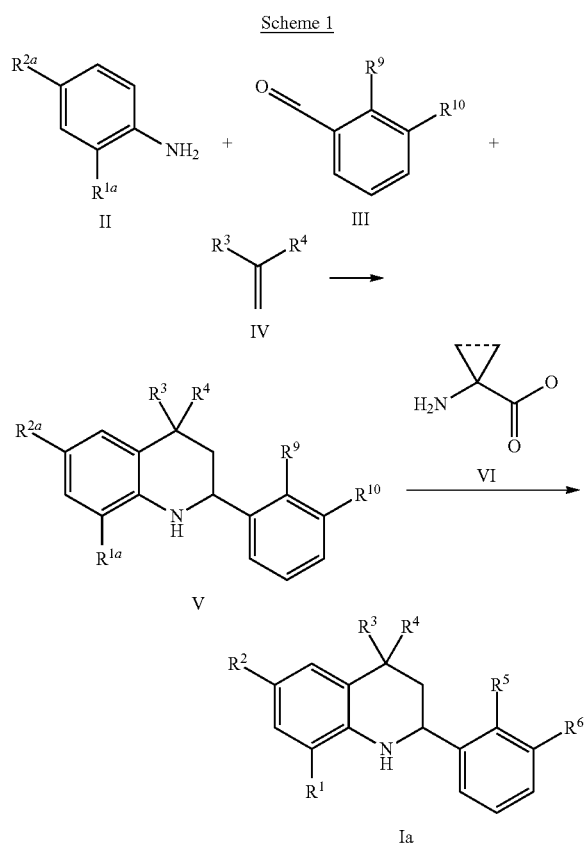

$R^{1a}$ is hydrogen, alkyl, halogen or alkoxycarbonyl; $R^{2a}$ is hydrogen, alkyl, haloalkyl, halogen, cyano or alkoxycarbonyl; $R^1$ is hydrogen, alkyl, halogen, or carboxy; $R^2$ is hydrogen, alkyl, haloalkyl, halogen, canyo or carboxy; $R^3$ and $R^4$ are independently selected from alkyl; one of $R^5$ and $R^6$ is carboxyalkylamino or carboxycycloalkylamino and the other is hydrogen; one of $R^9$ and $R^{10}$ is bromo and the other one is hydrogen.

The compound of formula Ia can be prepared according to Scheme 1. The tetrahydroquinoline V can be synthesized via the three components aza Diels-Alder reaction of the aniline II, the aldehyde III and methylene-alkene IV. Ullmann coupling reaction between tetrahydroquinoline V and amino acid VI affords the resulting compound Ia.

The compound V can be prepared by the three components aza Diels-Alder reaction of the aniline II the aldehyde III and the methylene-alkene IV. This Diels-Alder reaction can be carried out in the presence of a Lewis acid such as ytterbium (III) trifluoromethanesulfonate ($Yb(OTf)_3$), scandium(III) trifluoromethanesulfonate ($Sc(OTf)_3$), lanthanum(III) trifluoromethanesulfonate ($La(OTf)_3$), indium(III) trifluoromethanesulfonate ($In(OTf)_3$), indium trichloride ($InCl_3$), or boron trifluoride diethyl etherate ($BF_3.Et_2O$), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

The Ullmann coupling reaction as outlined in the Scheme 1 can be carried out in the presence of a copper source such as copper(I) iodide (CuI) or copper(II)trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

Scheme 2

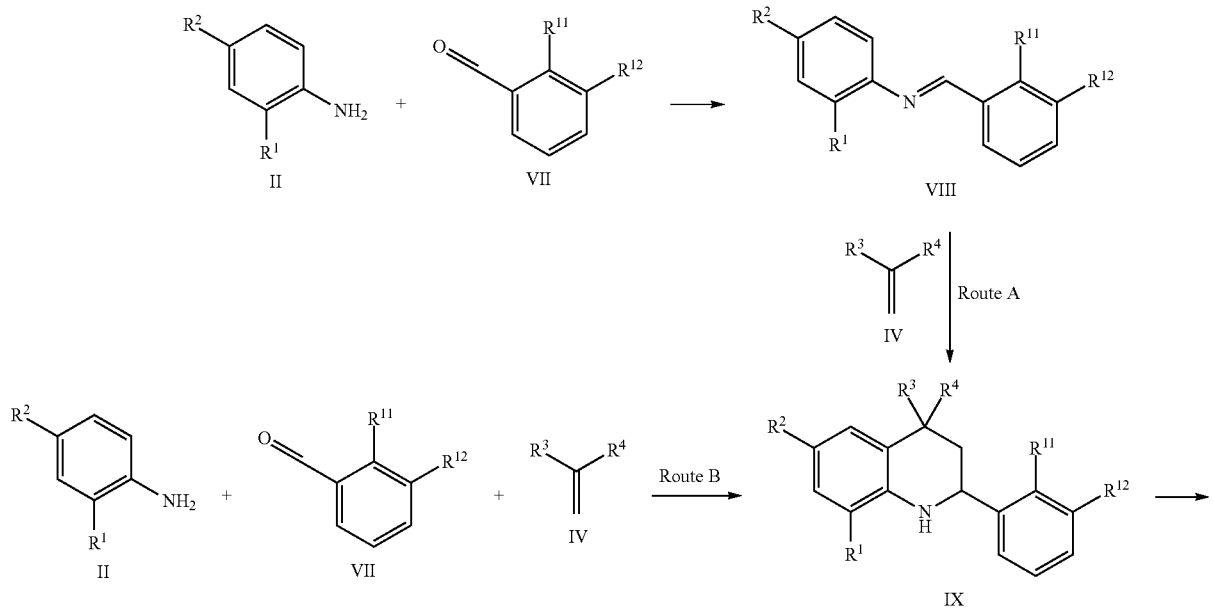

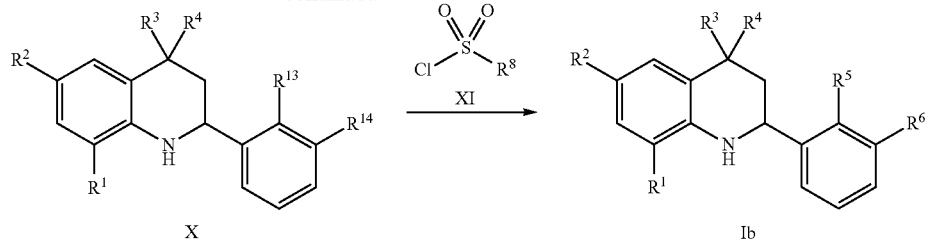

$R^1$ is hydrogen, alkyl, halogen; $R^2$ is hydrogen, alkyl, haloalkyl, halogen, or cyano; $R^3$ and $R^4$ are independently selected from alkyl; one of $R^5$ and $R^6$ is alkylsulfonylamino, phenylsulfonylamino, halophenylsulfonylamino, alkylphenylsulfonylamino or pyridinylsulfonylamino and the other is hydrogen; $R^8$ is alkyl, phenyl, halophenyl, alkylphenyl or pyridinyl; one of $R^{11}$ and $R^{12}$ is $NO_2$ and the other one is hydrogen; one of $R^{13}$ and $R^{14}$ is $NH_2$ and the other one is hydrogen.

The compound of formula Ib can be prepared according to Scheme 2. The aniline II reacts with the aldehyde VII to generate the imine VIII. The imine VII reacts with the methylene-alkene IV to afford the tetrahydroquinoline IX. Alternatively, the tetrahydroquinoline IX can be synthesized via the three component aza Diels-Alder reaction of the aniline II, the aldehyde VII and methylene-alkene IV. Reduction of the tetrahydroquinoline IX followed by coupling with sulfonyl chloride XI affords the resulting compound Ib.

In the method outlined in Scheme 2, the imine VIII can be prepared by a condensation reaction of the substituted aniline II and the substituted aldehyde VII in an organic solvent such as toluene, methanol or ethanol and a mixture thereof, at a temperature between 80 and 140° C. for 2 to 16 hours.

The compound IX can be prepared either by the aza Diels-Alder reaction between the imine VIII and the methylene-alkene IV or by the three component aza Diels-Alder reaction of the aniline II the aldehyde VII and the methylene-alkene IV. This Diels-Alder reaction can be carried out in the presence of a Lewis acid such as ytterbium(III) trifluoromethanesulfonate $(Yb(OTf)_3)$, scandium(III) trifluoromethanesulfonate $(Sc(OTf)_3)$, lanthanum(III) trifluoromethanesulfonate $(La(OTf)_3)$, indium(III) trifluoromethanesulfonate $(In(OTf)_3)$, indium trichloride $(InCl_3)$, or boron trifluoride diethyl etherate $(BF_3.Et_2O)$, or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

Reduction of the nitro compound Ix to the corresponding amine derivative X can be accomplished using methods well known to someone skilled in the art. The reaction is typically carried out under acidic conditions by using hydrochloric acid or ammonium chloride in a mixture of ethanol and water at reflux for several hours.

Conversion of the amine X to the corresponding sulfonamide Ib with suitable sulfonyl chloride XI can be easily accomplished using methods well known to someone skilled in the art. The reaction is typically carried out in the presence of a base such as triethylamine, N,N-diisopropylethylamine pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or a mixture thereof, at room temperature for several hours.

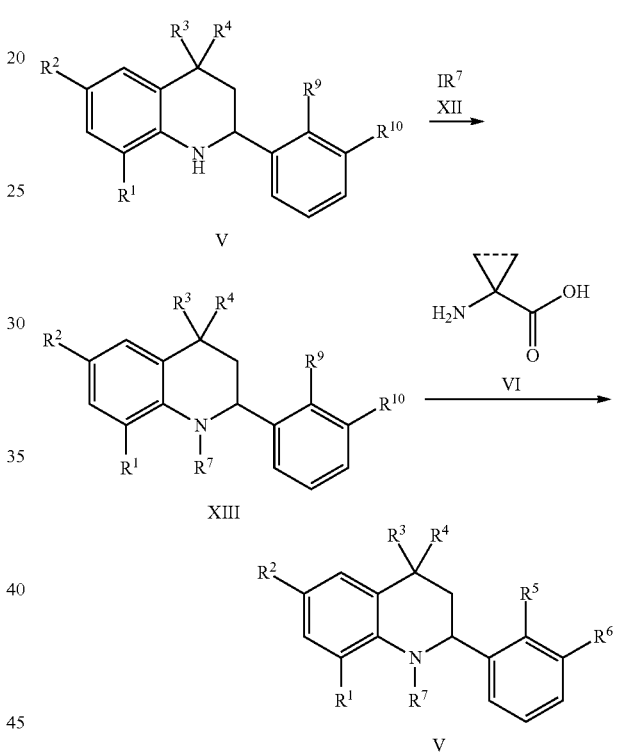

Scheme 3

$R^1$ is hydrogen, alkyl, halogen; $R^2$ is hydrogen, alkyl, haloalkyl, halogen or cyano; $R^3$ and $R^4$ are independently selected from alkyl; one of $R^5$ and $R^6$ is carboxyalkylamino or carboxycycloalkylamino and the other is hydrogen; $R^7$ is alkyl; one of $R^9$ and $R^{10}$ is Br and the other one is hydrogen.

The compound of formula Ic can be prepared according to Scheme 3. In this process, the compound of formula V can be synthesized as illustrated in Scheme 1. Alkylation of compound V followed by Ullmann coupling reaction with amino acid VI affords the resulting compound Ic.

Alkylation of compound of formula V can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or mixtures thereof, at room temperature for several hours.

The Ullmann coupling reaction as outlined in the Scheme 3 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

Scheme 4

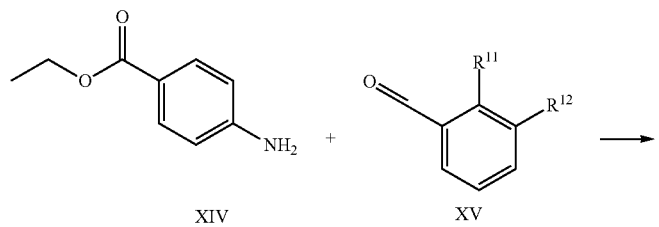

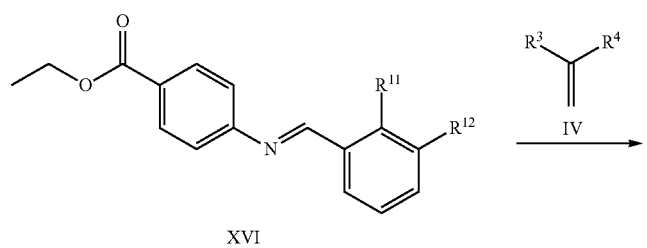

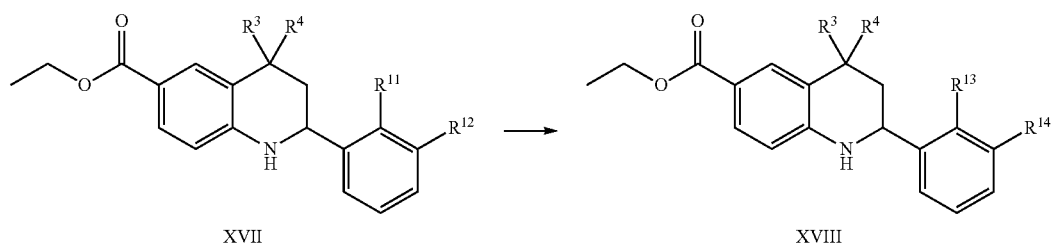

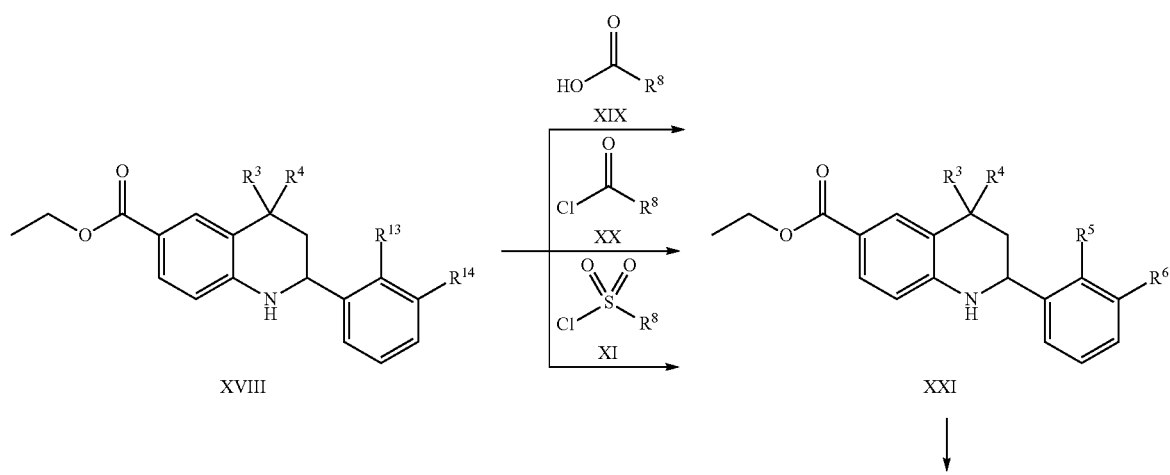

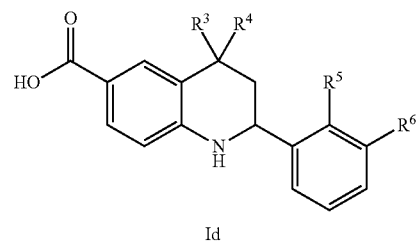

Id

R³ and R⁴ are independently selected from alkyl; one of R⁵ and R⁶ alkylsulfonylamino, phenylsulfonylamino, halophenylsulfonylamino, alkylphenylsulfonylamino, pyridinylsulfonylamino, phenylcarbonylamino or halophenylcarbonylamino; and the other is hydrogen; R⁸ is alkyl, phenyl, halophenyl, alkylphenyl or pyridinyl; one of R¹¹ and R¹² is NO₂ and the other one is hydrogen; one of R¹³ and R¹⁴ NH₂ and the other one is hydrogen.

The compound of formula Id can be prepared according to Scheme 4. The aniline XIV reacts with the aldehyde XV to generate the imine XVI. The imine XVI reacts with the methylene-alkene IV to afford the tetrahydroquinoline XVII. Reduction of the tetrahydroquinoline XVII followed by coupling with carboxylic acid XIX, carbonyl chloride XX or sulfonyl chloride XI affords the resulting compound XXI. Hydrolysis of the ethyl ester XXI affords the resulting product Id.

In the method outlined in Scheme 4, the imine XVI can be prepared by a condensation reaction of the substituted aniline XIV and the substituted aldehyde XV in an organic solvent such as toluene, methanol or ethanol and a mixture thereof, at a temperature between 80 and 140° C. for 2 to 16 hours.

The compound XVII can be prepared by the aza Diels-Alder reaction between the imine XVI and the methylene-alkene IV. This Diels-Alder reaction can be carried out in the presence of a Lewis acid such as ytterbium(III) trifluoromethanesulfonate (Yb(OTf)₃), scandium(III) trifluoromethanesulfonate (Sc(OTf)₃), lanthanum(III) trifluoromethanesulfonate (La(OTf)₃), indium(III) trifluoromethanesulfonate (In(OTf)₃), indium trichloride (InCl₃), or boron trifluoride diethyl etherate (BF₃.Et₂O), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., Tetrahedron 54 (1998) 5089).

Reduction of the nitro compound XVII to the corresponding amine derivative XVIII can be accomplished using methods well known to someone skilled in the art. The reaction is typically carried out under acidic conditions by using hydrochloric acid or ammonium chloride in a mixture of ethanol and water at reflux for several hours.

Conversion of the amine XVIII to the corresponding amide XXI with suitable carboxylic acid XIX can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., Tetrahedron 61 (2005) 10827).

Alternatively, conversion of the amine XVIII to the corresponding amide XXI can be easily accomplished by coupling amine XVIII with suitable carbonyl chloride XX in the presence of a base such as triethylamine, N,N-diisopropylethylamine pyridine or dimethyl-pyridin-4-yl-amine in a suitable inert solvent such as dichloromethane, acetonitrile, 1,4-dioxane, tetrahydrofuran or a mixture thereof, at room temperature for several hours. Carbonyl chloride is commercially available or generated in situ by treating carboxylic acid with phosphorus oxychloride.

Conversion of the amine XVIII to the corresponding sulfonamide XXI with suitable sulfonyl chloride XI can be easily accomplished using methods well known to someone skilled in the art. The reaction is typically carried out in the presence of a base such as triethylamine, N,N-diisopropylethylamine pyridine, sodium methoxide, sodium tert-butoxide, potassium tert-butoxide, sodium hydride or dimethylpyridin-4-yl-amine in a suitable inert solvent such as dichloromethane, acetonitrile, 1,4-dioxane, tetrahydrofuran or a mixture thereof, at room temperature for several hours.

Hydrolysis of the ethyl esters XXI to the resulting products Id can be carried out in the presence of an aqueous inorganic base such as lithium hydroxide, sodium hydroxide, or potassium hydroxide in a solvent such as methanol, 1,4-dioxane, tetrahydrofuran or a mixtures thereof at room temperature or refluxed for several hours.

Scheme 5

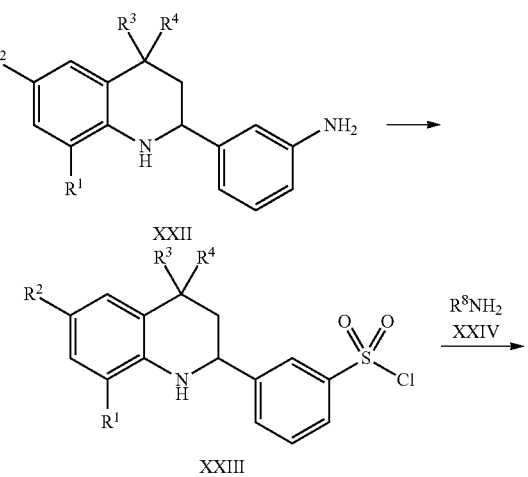

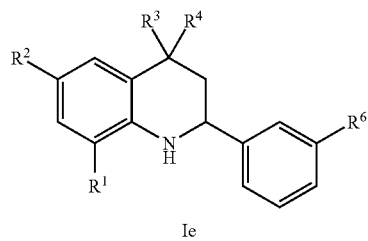

Ie

R$^1$ is hydrogen, alkyl, halogen; R$^2$ is hydrogen, alkyl, haloalkyl, halogen or cyano; R$^3$ and R$^4$ are independently selected from alkyl; R$^6$ is alkylaminosulfonyl, phenylaminosulfonyl or halophenylaminosulfonyl; R$^8$ is alkyl, phenyl or halophenyl.

The compound of formulas Ie can be prepared according to Scheme 5. The starting amine XXII can be prepared according to Scheme 2. Conversion of amine XXII to sulfonyl chloride followed by sulfonamide formation affords the resulting compound If.

Conversion of amine XXII to sulfonyl chloride XXIII can be easily accomplished by treating the diazonium salt solution in acetic acid and hydrochloric acid with sulphur dioxide solution in acetic acid in the presence of cupric chloride. The diazonium salt solution can be generated by treating amine XXII with sodium nitrite in acetic acid and hydrochloric acid solution.

Conversion of the sulfonyl chloride XXIII to the resulting sulfonamide Ie with suitable amine XXIV can be easily accomplished using methods well known to someone skilled in the art. The reaction is typically carried out in the presence of a base such as triethylamine, N,N-diisopropylethylamine pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or a mixture thereof, at room temperature for several hours.

Scheme 6

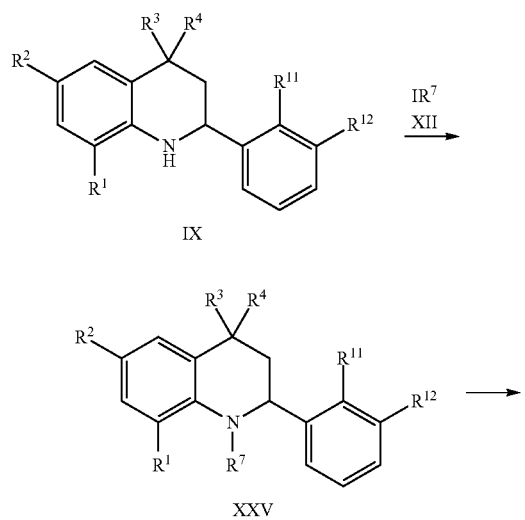

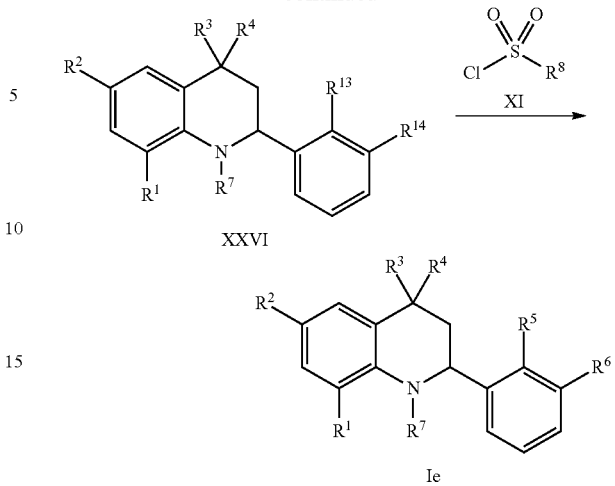

Ie

R$^1$ is hydrogen, alkyl or halogen; R$^2$ is hydrogen, alkyl, haloalkyl, halogen or cyano; R$^3$ and R$^4$ are independently selected from alkyl; one of R$^5$ and R$^6$ is alkylsulfonylamino, phenylsulfonylamino, halophenylsulfonylamino, alkylphenylsulfonylamino or pyridinylsulfonylamino. R$^7$ is alkyl; R$^8$ is alkyl, phenyl, halophenyl, alkylphenyl or pyridinyl. one of R$^{11}$ and R$^{12}$ is NO$_2$ and the other one is hydrogen; one of R$^{13}$ and R$^{14}$ is NH$_2$ and the other one is hydrogen.

The compound of formula Ie can be prepared according to Scheme 6. In this process, the compound of formula IX can be synthesized as illustrated in Scheme 2. Alkylation of compound IX affords XXV. Reduction of the tetrahydroquinoline XXV followed by coupling with sulfonyl chloride XI affords the resulting compound Ie.

Alkylation of compound of formula IX can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or mixtures thereof, at room temperature for several hours.

Reduction of the nitro compound XXV to the corresponding amine derivative XXVI can be accomplished using methods well known to someone skilled in the art. The reaction is typically carried out under acidic conditions by using hydrochloric acid or ammonium chloride in a mixture of ethanol and water at reflux for several hours.

Conversion of the amine XXVI to the corresponding sulfonamide Ie with suitable sulfonyl chloride XI can be easily accomplished using methods well known to someone skilled in the art. The reaction is typically carried out in the presence of a base such as triethylamine, N,N-diisopropylethylamine pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or a mixture thereof, at room temperature for several hours.

This invention also relates to a process for the preparation of a compound of formula (I) comprising one of the following steps:

The invention also relates to a process for the preparation of a compound of formula (I) comprising one of the following steps:

(a) the reaction of a compound of formula (A)

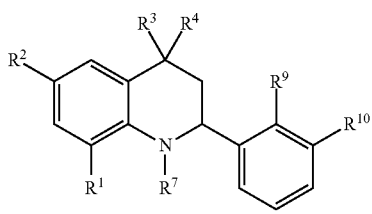

in the presence of 1-amino-cyclopropanecarboxylic acid or 2-amino-2-methyl-propionic acid and in the presence of a copper source, a ligand and a base;
(b) the reaction of a compound of formula (B)

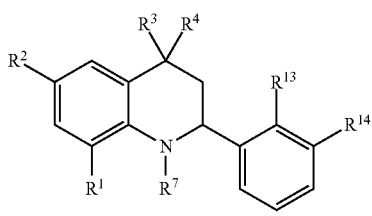

in the presence of $ClSO_2R^8$ and a base;
(c) the reaction of a compound of formula (C)

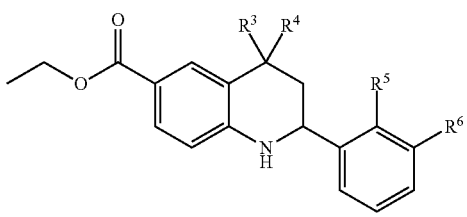

in the presence of a base;
(d) the reaction of a compound of formula (D)

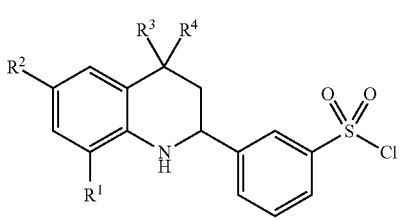

in the presence of $R^8NH_2$ and a base;
wherein $R^1$, $R^2$, $R^3$, $R^4$, $R^5$, $R^6$ and $R^7$ are defined as in any one of claims 1 to 13; $R^8$ is alkyl, phenyl, halophenyl, alkylphenyl or pyridinyl; one of $R^9$ and $R^{10}$ is bromo and the other one is hydrogen; one of $R^{13}$ and $R^{14}$ is —$NH_2$ and the other one is hydrogen.

In step (a), the copper source can be for example copper(I) iodide (CuI) or copper(II)trifluoromethanesulfonate; the ligand can be for example 2, 2'-bipyridine, proline, N,N'-dimethyl glycine or ethylene glycol; and the base can be for example triethylamine, sodium carbonate, potassium carbonate, cesium carbonate, sodium methoxide, sodium tert-butoxide or potassium tert-butoxide.

In step (b), the base can be for example triethylamine, N,N-diisopropylethylamine pyridine, sodium methoxide, sodium tert-butoxide, potassium tert-butoxide, sodium hydride or dimethyl-pyridin-4-yl-amine.

In step (c), the base can be for example lithium hydroxide, sodium hydroxide or potassium hydroxide.

In step (d), the base can be for example triethylamine, N,N-diisopropylethylamine pyridine, sodium methoxide, sodium tert-butoxide, potassium tert-butoxide, sodium hydride or dimethyl-pyridin-4-yl-amine.

The invention also relates to a compound of formula (I) for use as therapeutically active substance.

The invention also relates to a pharmaceutical composition comprising a compound of formula (I) and a therapeutically inert carrier.

The use of a compound of formula (I) for the preparation of medicaments useful in the treatment or prophylaxis diseases that are related to AMPK regulation is an object of the invention.

The invention relates in particular to the use of a compound of formula (I) for the preparation of a medicament for the treatment or prophylaxis of obesity, dyslipidemia, hyperglycemia, type 1 or type 2 diabetes, in particular type 2 diabetes.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts can be used, for example, as such carriers (or excipients) for tablets, coated tablets, dragées and hard gelatine capsules. Suitable carriers for soft gelatine capsules are, for example, vegetable oils, waxes, fats, semi-solid and liquid polyols. Depending on the nature of the active substance no carriers are, however, usually required in the case of soft gelatine capsules. Suitable carriers for the production of solutions and syrups are, for example, water, polyols, glycerol, vegetable oil. Suitable carriers for suppositories are, for example, natural or hardened oils, waxes, fats, semi-liquid or liquid polyols.

The pharmaceutical composition can contain preservatives, solubilizers, stabilizers, wetting agents, emulsifiers, sweeteners, colorants, flavorants, salts for varying the osmotic pressure, buffers, masking agents or antioxidants. They can also contain other therapeutically valuable substances.

The dosage depends on various factors such as the manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I).

The invention further relates to a method for the treatment or prophylaxis of obesity, dyslipidemia, hyperglycemia, type 1 or type 2 diabetes, in particular type 2 diabetes, which method comprises administering an effective amount of a compound of formula (I).

Furthermore, the invention also relates to the use of a compound of formula (I) for the preparation of medicaments useful in the treatment of cancer, in particular of cancers that are related to AMPK regulation. The invention provides a method for the treatment of cancers, in particular cancers that are related to AMPK regulation, which method comprises administering an effective amount of a compound of formula (I).

The invention will be illustrated by the following examples which have no limiting character. Unless explicitly otherwise stated, all reactions, reaction conditions, abbreviations and symbols have the meanings well known to a person of ordinary skill in organic chemistry.

EXAMPLES

Materials and Instrumentation

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C18 (5 μm, OBD™ 30×100 mm) column or SunFire™ Perp C18 (5 μm, OBD™ 30×100 mm) column.

LC/MS spectra were obtained using a MicroMass Plateform LC (Waters™ alliance 2795-ZQ2000). Standard LC/MS conditions were as follows (running time 6 min):
Acidic condition: A: 0.1% formic acid in $H_2O$; B: 0.1% formic acid in acetonitrile;
Basic condition: A: 0.01% $NH_3.H_2O$ in $H_2O$; B: acetonitrile;
Neutral condition: A: $H_2O$; B: acetonitrile.

Mass spectra (MS): generally only ions which indicate the parent mass are reported, and unless otherwise stated the mass ion quoted is the positive mass ion-$(M+H)^+$.

The microwave assisted reactions were carried out in a Biotage Initiator Sixty.

NMR Spectra were obtained using Bruke Avance 400 MHz.

All reactions involving air-sensitive reagents were performed under an argon atmosphere. Reagents were used as received from commercial suppliers without further purification unless otherwise noted.

Example 1

2-[3-(6-Chloro-4,4-dimethyl-1,2,3,4-tetrahydro-quinolin-2-yl)-phenylamino]-2-methyl-propionic acid

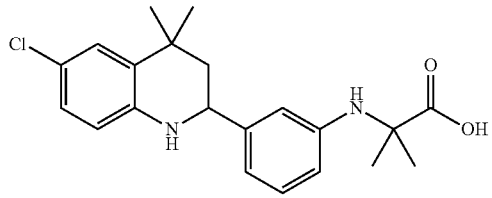 [SMILES: CC(C)(Nc1cccc(C2CC(C)(C)c3cc(Cl)ccc3N2)c1)C(=O)O]

To a stirred solution of 4-chlorophenylamine (10.0 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb $(OTf)_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 0-10% ethyl acetate in petroleum ether) to afford 2-(3-bromo-phenyl)-6-chloro-4,4-dimethyl-1,2,3,4-tetrahydro-quinoline (11.0 g, 40.0%) as a light yellow solid: LC/MS m/e obsd. ($ESI^+$) [$(M+H)^+$] 350.0 & 352.0.

A solution of 2-(3-bromo-phenyl)-6-chloro-4,4-dimethyl-1,2,3,4-tetrahydro-quinoline (200 mg, 0.57 mmol), copper(I) iodide (33 mg, 0.17 mmol), 2-amino-2-methyl-propionic acid (235 mg, 2.29 mmol) and potassium carbonate (240 mg, 1.7 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-chloro-4,4-dimethyl-1,2,3,4-tetrahydro-quinolin-2-yl)-phenylamino]-2-methyl-propionic acid (127 mg, 60.0%) as a white solid: LC/MS m/e obsd. ($ESI^+$) [$(M+H)^+$] 373.0.

Example 2

1-[3-(6-Chloro-4,4-dimethyl-1,2,3,4-tetrahydro-quinolin-2-yl)-phenylamino]-cyclopropanecarboxylic acid

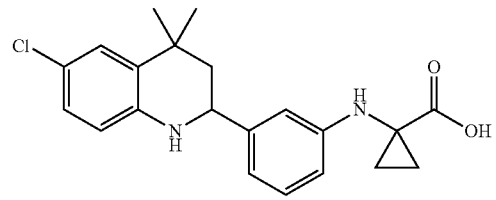 [SMILES: CC1(C)CC(c2cccc(NC3(C(=O)O)CC3)c2)Nc2ccc(Cl)cc21]

A solution of 2-(3-bromo-phenyl)-6-chloro-4,4-dimethyl-1,2,3,4-tetrahydro-quinoline (200 mg, 0.57 mmol), copper(I) iodide (33 mg, 0.17 mmol), 1-amino-cyclopropanecarboxylic acid (235 mg, 2.29 mmol) and potassium carbonate (240 mg, 1.7 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-chloro-4,4-dimethyl-1,2,3,4-tetrahydro-quinolin-2-yl)-phenylamino]-cyclopropanecarboxylic acid (84.3 mg, 40.0%) as a white solid: LC/MS m/e obsd. ($ESI^+$) [$(M+H)^+$] 371.1.

Example 3

2-[3-(6-Cyano-4,4-dimethyl-1,2,3,4-tetrahydro-quinolin-2-yl)-phenylamino]-2-methyl-propionic acid

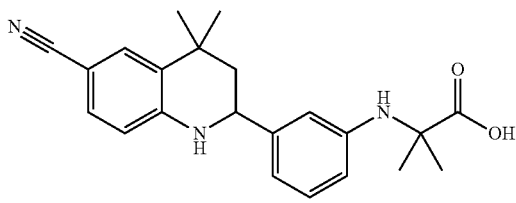 [SMILES: CC(C)(Nc1cccc(C2CC(C)(C)c3cc(C#N)ccc3N2)c1)C(=O)O]

To a stirred solution of 4-aminobenzonitrile (10.0 g, 84.7 mmol) and 3-bromobenzaldehyde (10 mL, 84.7 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 0-10% ethyl acetate in petroleum ether) to afford 2-(3-bromo-phenyl)-4,4-dimethyl-1,2,3,4-tetrahydro-quinoline-6-carbonitrile (11.6 g, 40.0%) as a light yellow solid: LC/MS m/e obsd. (ESI$^+$) [(M+H)$^+$] 341.0 & 343.0.

A solution of 2-(3-bromo-phenyl)-4,4-dimethyl-1,2,3,4-tetrahydro-quinoline-6-carbonitrile (341 mg, 1.0 mmol), copper(I) iodide (57.0 mg, 0.3 mmol), 2-amino-2-methyl-propionic acid (235 mg, 4.0 mmol) and potassium carbonate (420 mg, 3.0 mmol) in dimethyl sulfoxide (4.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyano-4,4-dimethyl-1,2,3,4-tetrahydro-quinolin-2-yl)-phenylamino]-2-methyl-propionic acid (120.1 mg, 33.1%) as a white solid: LC/MS m/e obsd. (ESI$^+$) [(M+H)$^+$] 364.1.

Example 4

1-[3-(6-Cyano-4,4-dimethyl-1,2,3,4-tetrahydro-quinolin-2-yl)-phenylamino]-cyclopropanecarboxylic acid

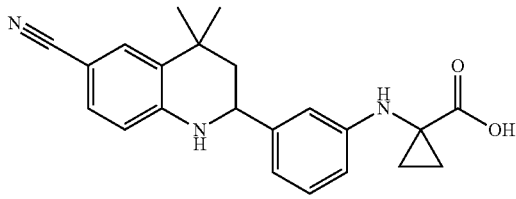 [SMILES: CC1(C)CC(c2cccc(NC3(C(=O)O)CC3)c2)Nc2ccc(C#N)cc21]

A solution of 2-(3-bromo-phenyl)-4,4-dimethyl-1,2,3,4-tetrahydro-quinoline-6-carbonitrile (341 mg, 1.0 mmol), copper(I) iodide (57.0 mg, 0.3 mmol), 1-amino-cyclopropanecarboxylic acid (235 mg, 4.0 mmol) and potassium carbonate (420 mg, 3.0 mmol) in dimethyl sulfoxide (4.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-cyano-4,4-dimethyl-1,2,3,4-tetrahydro-quinolin-2-yl)-phenylamino]-cyclopropanecarboxylic acid (101.4 mg, 28.1%) as a white solid: LC/MS m/e obsd. (ESI$^+$) [(M+H)$^+$] 362.2.

Example 5

2-[3-(1-Carboxy-cyclopropylamino)-phenyl]-4,4-dimethyl-1,2,3,4-tetrahydro-quinoline-8-carboxylic

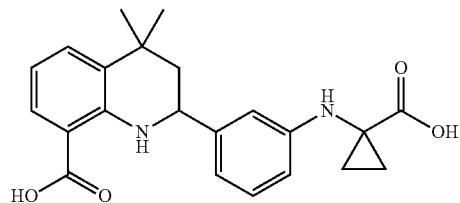 [SMILES: CC1(C)CC(c2cccc(NC3(C(=O)O)CC3)c2)Nc2c(C(=O)O)cccc21]

To a stirred solution of 2-amino-benzoic acid methyl ester (11.3 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4-dimethyl-1,2,3,4-tetrahydro-quinoline-8-carboxylic acid methyl ester (11.7 g, 40.0%) as a light yellow solid: LC/MS m/e obsd. (ESI$^+$) [(M+H)$^+$] 374.0 & 376.0.

A solution of 2-(3-bromo-phenyl)-4,4-dimethyl-1,2,3,4-tetrahydro-quinoline-8-carboxylic acid methyl ester (374 mg, 1.0 mmol), copper(I) iodide (57 mg, 0.3 mmol), 1-amino-cyclopropanecarboxylic acid (309 mg, 3.0 mmol) and potassium carbonate (415 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(1-carboxy-cyclopropylamino)-phenyl]-4,4-dimethyl-1,2,3,4-tetrahydro-quinoline-8-carboxylic acid (228 mg, 60.0%) as a white solid: LC/MS m/e obsd. (ESI+) [(M+H)+] 381.0.

Example 6

2-[3-(1-Carboxy-cyclopropylamino)-phenyl]-6-chloro-4,4-dimethyl-1,2,3,4-tetrahydro-quinoline-8-carboxylic acid

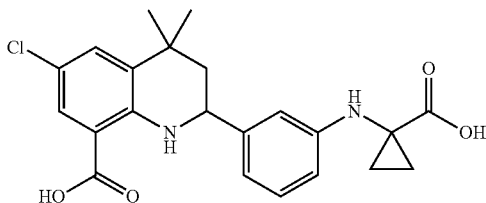 [SMILES: CC1(C)CC(c2cccc(NC3(C(=O)O)CC3)c2)Nc2c(C(=O)O)cc(Cl)cc21]

To a stirred solution of 2-amino-5-chloro-benzoic acid methyl ester (14.5 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)₃) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-30% ethyl acetate in petroleum ether) to afford 2-(3-bromo-phenyl)-6-chloro-4,4-dimethyl-1,2,3,4-tetrahydro-quinoline-8-carboxylic acid methyl ester (6.7 g, 21.2%) as a light yellow oil: LC/MS m/e obsd. (ESI+) [(M+H)+] 408.0 & 410.0.

A solution of 2-(3-bromo-phenyl)-6-chloro-4,4-dimethyl-1,2,3,4-tetrahydro-quinoline-8-carboxylic acid methyl ester (408.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(1-carboxy-cyclopropylamino)-phenyl]-6-chloro-4,4-dimethyl-1,2,3,4-tetrahydro-quinoline-8-carboxylic acid (130.4 mg, 31.5%) as a white solid: LC/MS m/e obsd. (ESI+) [(M+H)+] 415.1.

Example 7

2-[3-(1-Carboxy-1-methyl-ethylamino)-phenyl]-6-chloro-4,4-dimethyl-1,2,3,4-tetrahydro-quinoline-8-carboxylic acid

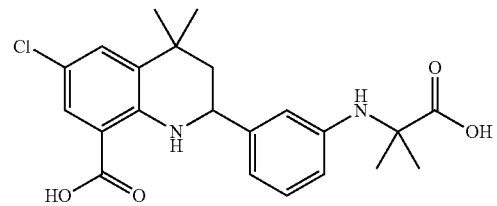 [SMILES: CC(C)(Nc1cccc(C2CC(C)(C)c3cc(Cl)cc(C(=O)O)c3N2)c1)C(=O)O]

A solution of 2-(3-bromo-phenyl)-6-chloro-4,4-dimethyl-1,2,3,4-tetrahydro-quinoline-8-carboxylic acid methyl ester (408.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(1-carboxy-cyclopropylamino)-phenyl]-6-chloro-4,4-dimethyl-1,2,3,4-tetrahydro-quinoline-8-carboxylic acid (78.6 mg, 18.9%) as a white solid: LC/MS m/e obsd. (ESI+) [(M+H)+] 417.1.

Example 8

1-[3-(6-Cyano-4,4,8-trimethyl-1,2,3,4-tetrahydro-quinolin-2-yl)-phenylamino]-cyclopropanecarboxylic acid

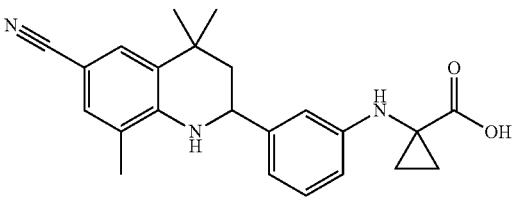

To a stirred solution of 4-amino-3-methyl-benzonitrile (10.3 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)₃) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-30% ethyl acetate in petroleum ether) to afford 2-(3-bromo-phenyl)-4,4,8-trimethyl-1,2,3,4-tetrahydro-quinoline-6-carbonitrile (7.3 g, 26.1%) as a light yellow oil: LC/MS m/e obsd. (ESI⁺) [(M+H)⁺] 355.0 & 357.0.

A solution of 2-(3-bromo-phenyl)-4,4,8-trimethyl-1,2,3,4-tetrahydro-quinoline-6-carbonitrile (355.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-cyano-4,4,8-trimethyl-1,2,3,4-tetrahydro-quinolin-2-yl)-phenylamino]-cyclopropanecarboxylic acid (79.8 mg, 21.3%) as a white solid: LC/MS m/e obsd. (ESI⁺) [(M+H)⁺] 376.2.

Example 9

2-[3-(4,4-Dimethyl-6-trifluoromethyl-1,2,3,4-tetrahydro-quinolin-2-yl)-phenylamino]-2-methyl-propionic acid

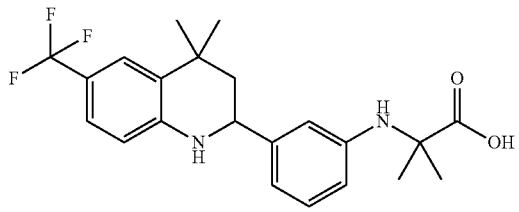 [SMILES: CC(C)(Nc1cccc(C2CC(C)(C)c3cc(C(F)(F)F)ccc3N2)c1)C(=O)O]

To a stirred solution of 4-trifluoromethyl-phenylamine (12.6 g, 78.4 mmol) and 3-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)₃) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 20-40% ethyl acetate in petroleum ether) to afford 2-(3-bromo-phenyl)-4,4-dimethyl-6-trifluoromethyl-1,2,3,4-tetrahydro-quinoline (12.1 g, 40%) as a light yellow oil: LC/MS m/e obsd. (ESI⁺) [(M+H)⁺] 383.9 & 385.9.

A solution of 2-(3-bromo-phenyl)-4,4-dimethyl-6-trifluoromethyl-1,2,3,4-tetrahydro-quinoline (384.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(4,4-dimethyl-6-trifluoromethyl-1,2,3,4-tetrahydro-quinolin-2-yl)-phenylamino]-2-methyl-propionic acid (85.6 mg, 21.1%) as a white solid: LC/MS m/e obsd. (ESI⁺) [(M+H)⁺] 407.1.

Example 10

N-[2-(6-Chloro-4,4-dimethyl-1,2,3,4-tetrahydro-quinolin-2-yl)-phenyl]-methanesulfonamide

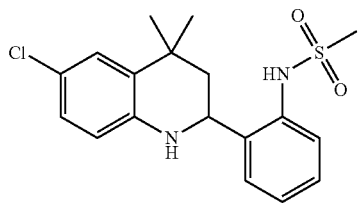 [SMILES: CC1(C)CC(c2ccccc2NS(C)(=O)=O)Nc2ccc(Cl)cc21]

To a stirred suspension of 4-chloro-phenylamine (10.2 g, 80 mmol), 2-nitrobenzaldehyde (12.1 g, 80 mmol), and 2-methylpropene (25 ml, pre-cooled to −78° C.) in acetonitrile was added ytterbium trifluoromethanesulfonate (1.3 g, 2.1 mmol) at ice-bath. The resulting mixture was stirred at 80° C. for 16 h in sealed tube. The reaction mixture was cooled to 0° C. The mixture was concentrated in vacuum. The residue was diluted with water, extracted with diethyl ether. The extracts were washed with brine and then dried over anhydrous sodium sulfate, concentrated in vacuo. The residue was purified by column chromatography to give 6-chloro-4,4-dimethyl-2-(2-nitrophenyl)-1,2,3,4-tetrahydroquinoline (7.8 g, 30.8%). LC/MS m/e obsd. (ESI⁺) [(M+H)⁺] 317.1.

To a stirred solution of 6-chloro-4,4-dimethyl-2-(2-nitrophenyl)-1,2,3,4-tetrahydroquinoline (7.7 g, 24.3 mmol) in ethanol and 10% hydrochloric acid was added iron powder (7.0 g, 125.4 mmol). The resulting mixture was stirred at 90° C. for 3 h. Then the insoluble solid was filtered off and the filtrate was concentrated in vacuum. The residue was extracted with ethyl acetate, washed with saturated sodium carbonate, dried over anhydrous sodium sulfate and concentrated in vacuo. The residue was purified by column chromatography to give 2-(6-chloro-4,4-dimethyl-1,2,3,4-tetrahydroquinolin-2-yl)aniline (2.5 g, yield 35.7%) LC/MS m/e obsd. (ESI⁺) [(M+H)⁺] 287.2.

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and methanesulfonyl chloride (40 mg, 0.35 mL) at ice-bath. The reaction mixture was stirred at room temperature for 4 h. The reaction mixture was washed with water. The aqueous layer was extracted with dichloromethane. The combined organic layer was washed by brine, dried over anhydrous sodium sulfate, concentrated in vacuo. The residue was purified by HPLC to give N-[2-(6-chloro-4,4-dimethyl-1,2,3,4-tetrahydro-quinolin-2-yl)-phenyl]-methanesulfonamide. LC/MS m/e obsd. (ESI⁺) [(M+H)⁺] 365.2.

Example 11

2-Methyl-2-[3-(1,4,4-trimethyl-6-trifluoromethyl-1,2,3,4-tetrahydro-quinolin-2-yl)-phenylamino]-propionic acid

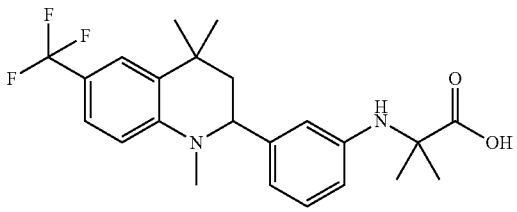 [SMILES: CN1c2ccc(C(F)(F)F)cc2C(C)(C)CC1c1cccc(NC(C)(C)C(=O)O)c1]

To a stirred solution of 2-(3-bromo-phenyl)-4,4-dimethyl-6-trifluoromethyl-1,2,3,4-tetrahydro-quinoline (5.0 g, 13.06 mmol) in N,N-dimethylformamide (15 mL) was added a 60% dispersion of sodium hydride in mineral oil (1.1 g, 26.1 mmol) portionwise at 0° C. The mixture was stirred at 0° C. for 30 min and then iodomethane (2.5 mL, 39.2 mmol) was added to the above mixture dropwise at 0° C. The solution was stirred at 0° C. for 2 h and then extracted with ethyl acetate, washed with brine, dried over anhydrous sodium sulfate and concentrated in vacuo. The yellowish residue was purified by ISCO combi-flash chromatography (gradient elution, 10% ethyl acetate/hexane) to afford 2-(3-bromo-phenyl)-1,4,4-trimethyl-6-trifluoromethyl-1,2,3,4-tetrahydroquinoline (3.6 g, 70%) as a yellow oil: MS obsd. (ESI$^+$) [(M+H)$^+$] 397.9 & 399.9.

A solution of 2-(3-bromo-phenyl)-1,4,4-trimethyl-6-trifluoromethyl-1,2,3,4-tetrahydro-quinoline (398.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-methyl-2-[3-(1,4,4-trimethyl-6-trifluoromethyl-1,2,3,4-tetrahydro-quinolin-2-yl)-phenylamino]-propionicacid (126.4 mg, 30.1%) as a white solid: LC/MS m/e obsd. (ESI$^+$) [(M+H)$^+$] 421.3.

Example 12

1 2-[3-(6-Cyano-4,4,8-trimethyl-1,2,3,4-tetrahydro-quinolin-2-yl)-phenylamino]-2-methyl-propionic acid

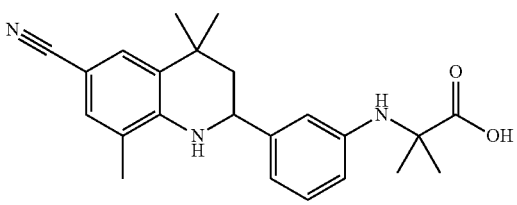 [SMILES: Cc1cc(C#N)cc2c1NC(c1cccc(NC(C)(C)C(=O)O)c1)CC2(C)C]

A solution of 2-(3-bromo-phenyl)-4,4,8-trimethyl-1,2,3,4-tetrahydro-quinoline-6-carbonitrile (355.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyano-4,4,8-trimethyl-1,2,3,4-tetrahydro-quinolin-2-yl)-phenylamino]-2-methyl-propionic acid (86.7 mg, 23%) as a white solid: LC/MS m/e obsd. (ESI$^+$) [(M+H)$^+$] 378.1.

Example 13

1-[3-(1,4,4-Trimethyl-6-trifluoromethyl-1,2,3,4-tetrahydro-quinolin-2-yl)-phenylamino]-cyclopropanecarboxylic acid

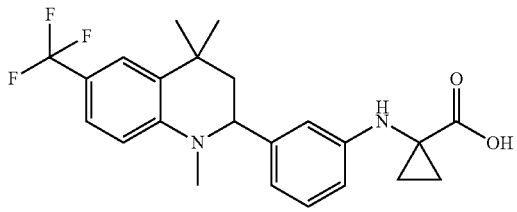 [SMILES: CN1c2ccc(C(F)(F)F)cc2C(C)(C)CC1c1cccc(NC2(C(=O)O)CC2)c1]

A solution of 2-(3-bromo-phenyl)-1,4,4-trimethyl-6-trifluoromethyl-1,2,3,4-tetrahydro-quinoline (398.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(1,4,4-trimethyl-6-trifluoromethyl-1,2,3,4-tetrahydro-quinolin-2-yl)-phenylamino]-cyclopropanecarboxylic acid (167.6 mg, 40%) as a white solid: LC/MS m/e obsd. (ESI$^+$) [(M+H)$^+$] 419.2.

Example 14

N-[2-(6-Chloro-4,4-dimethyl-1,2,3,4-tetrahydro-quinolin-2-yl)-phenyl]-3-fluoro-benzenesulfonamide

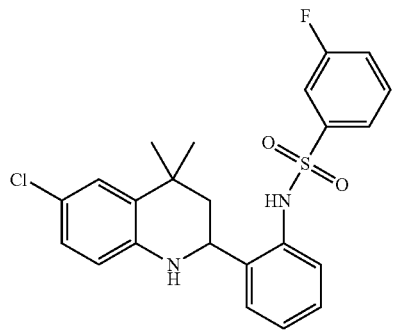 [SMILES: CC1(C)CC(c2ccccc2NS(=O)(=O)c2cccc(F)c2)Nc2ccc(Cl)cc21]

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and 3-fluorobenzenesulfonyl chloride (68 mg, 0.35 mmol) at ice-bath. The reaction mixture was stirred at room temperature overnight. The reaction mixture was washed with water. The aqueous layer was extracted with dichloromethane. The combined organic layer was washed by brine, dried over anhydrous sodium sulfate, concentrated in vacuo. The residue was purified by HPLC to give N-[2-(6-chloro-4,4-dimethyl-1,2,3,4-tetrahydro-quinolin-2-yl)-phenyl]-3-fluoro-benzenesulfonamide. LC/MS m/e obsd. (ESI$^-$) [(M–H)$^-$] 443.2.

Example 15

2-[3-(1-Carboxy-1-methyl-ethylamino)-phenyl]-4,4-dimethyl-1,2,3,4-tetrahydro-quinoline-8-carboxylic acid

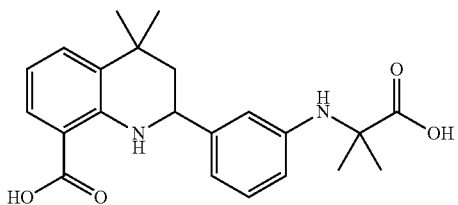

A solution of 2-(3-bromo-phenyl)-4,4-dimethyl-1,2,3,4-tetrahydro-quinoline-8-carboxylic acid methyl ester (374 mg, 1.0 mmol), copper(I) iodide (57 mg, 0.3 mmol), 2-amino-2-methyl-propionic acid (309 mg, 3.0 mmol) and potassium carbonate (415 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(1-carboxy-1-methyl-ethylamino)-phenyl]-4,4-dimethyl-1,2,3,4-tetrahydro-quinoline-8-carboxylic acid (95.3 mg, 25.1%) as a white solid: LC/MS m/e obsd. (ESI$^+$) [(M+H)$^+$] 383.1.

Example 16

Ethanesulfonic acid [2-(6-chloro-4,4-dimethyl-1,2,3,4-tetrahydro-quinolin-2-yl)-phenyl]-amide

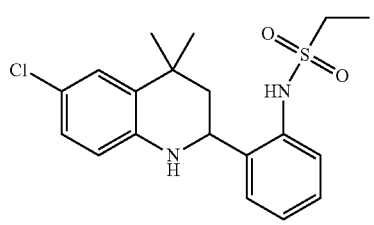 [SMILES: CCS(=O)(=O)Nc1ccccc1C1CC(C)(C)c2cc(Cl)ccc2N1]

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and ethanesulfonyl chloride (45 mg, 0.35 mmol) at ice-bath. The reaction mixture was stirred at room temperature overnight. The reaction mixture was washed with water. The aqueous layer was extracted with dichloromethane. The combined organic layer was washed by brine, dried over anhydrous sodium sulfate, concentrated in vacuo. The residue was purified by HPLC to give ethanesulfonic acid [2-(6-chloro-4,4-dimethyl-1,2,3,4-tetrahydro-quinolin-2-yl)-phenyl]-amide LC/MS m/e obsd. (ESI$^+$) [(M+H)$^+$] 379.20.

Example 17

1-[3-(4,4-Dimethyl-6-trifluoromethyl-1,2,3,4-tetrahydro-quinolin-2-yl)-phenylamino]-cyclopropanecarboxylic acid

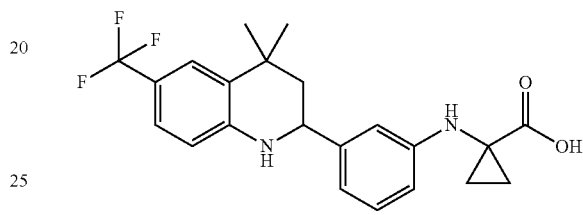

A solution of 2-(3-bromo-phenyl)-4,4-dimethyl-6-trifluoromethyl-1,2,3,4-tetrahydro-quinoline (384.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(4,4-dimethyl-6-trifluoromethyl-1,2,3,4-tetrahydro-quinolin-2-yl)-phenylamino]-cyclopropanecarboxylic acid (85.6 mg, 23.1%) as a white solid: LC/MS m/e obsd. (ESI$^+$) [(M+H)$^+$] 405.2.

Example 18

1-[3-(8-Chloro-6-cyano-4,4-dimethyl-1,2,3,4-tetrahydro-quinolin-2-yl)-phenylamino]-cyclopropanecarboxylic acid

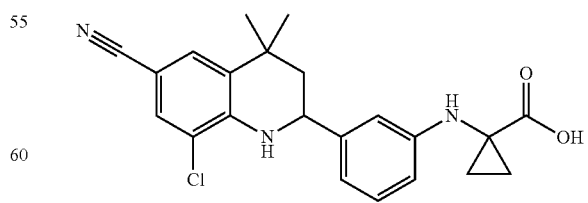

To a stirred solution of 4-amino-3-chloro-benzonitrile (8.0 g, 52.4 mmol) and 3-bromobenzaldehyde (6.2 mL, 52.4 mmol) in acetonitrile (150 mL) were added isobutene (14.7 mL, 209.7 mmol) and ytterbium(III) trifluoromethanesulfonate (Yb(OTf)$_3$) (4.0 g, 6.3 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-8-chloro-4,4-dimethyl-1,2,3,4-tetrahydro-quinoline-6-carbonitrile (7.8 g, 40.0%) as a light yellow solid: LC/MS m/e obsd. (ESI$^+$) [(M+H)$^+$] 374.9 & 376.9.

A solution of 2-(3-bromo-phenyl)-8-chloro-4,4-dimethyl-1,2,3,4-tetrahydro-quinoline-6-carbonitrile (374.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(8-chloro-6-cyano-4,4-dimethyl-1,2,3,4-tetrahydro-quinolin-2-yl)-phenylamino]-cyclopropanecarboxylic acid (118.8 mg, 30.1%) as a white solid: LC/MS m/e obsd. (ESI$^+$) [(M+H)$^+$] 396.1.

Example 19

N-[2-(6-Chloro-4,4-dimethyl-1,2,3,4-tetrahydro-quinolin-2-yl)-phenyl]-4-fluoro-benzenesulfonamide

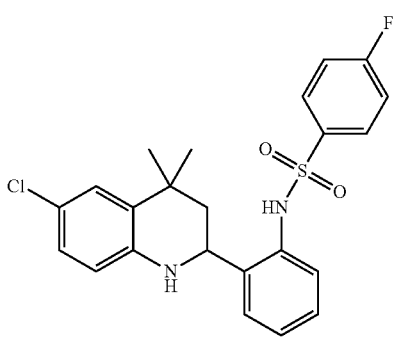 [SMILES: CC1(C)CC(c2ccccc2NS(=O)(=O)c2ccc(F)cc2)Nc2ccc(Cl)cc21]

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and 4-fluorobenzenesulfonyl chloride (68 mg, 0.35 mmol) at ice-bath. The reaction mixture was stirred at room temperature overnight. The reaction mixture was washed with water. The aqueous layer was extracted with dichloromethane. The combined organic layer was washed by brine, dried over anhydrous sodium sulfate, concentrated in vacuo. The residue was purified by HPLC to give N-[2-(6-chloro-4,4-dimethyl-1,2,3,4-tetrahydro-quinolin-2-yl)-phenyl]-4-fluoro-benzenesulfonamide LC/MS m/e obsd. (ESI$^+$) [(M+H)$^+$] 445.2.

Example 20

2-[2-(6-Cyano-4,4-dimethyl-1,2,3,4-tetrahydro-quinolin-2-yl)-phenylamino]-2-methyl-propionic acid

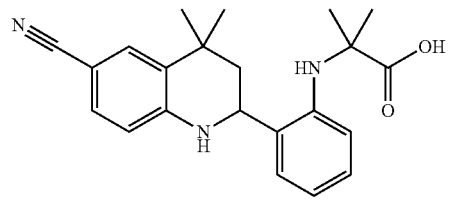 [SMILES: CC(C)(Nc1ccccc1C1CC(C)(C)c2cc(C#N)ccc2N1)C(=O)O]

To a stirred solution of 4-aminobenzonitrile (10.0 g, 84.7 mmol) and 2-bromobenzaldehyde (10 mL, 84.7 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 0-10% ethyl acetate in petroleum ether) to afford 2-(2-bromo-phenyl)-4,4-dimethyl-1,2,3,4-tetrahydro-quinoline-6-carbonitrile (11.6 g, 40.0%) as a light yellow solid: LC/MS m/e obsd. (ESI$^+$) [(M+H)$^+$] 341.0 & 343.0.

A solution of 2-(2-bromo-phenyl)-4,4-dimethyl-1,2,3,4-tetrahydro-quinoline-6-carbonitrile (341 mg, 1.0 mmol), copper(I) iodide (57.0 mg, 0.3 mmol), 2-amino-2-methyl-propionic acid (235 mg, 4.0 mmol) and potassium carbonate (420 mg, 3.0 mmol) in dimethyl sulfoxide (4.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(6-cyano-4,4-dimethyl-1,2,3,4-tetrahydro-quinolin-2-yl)-phenylamino]-2-methyl-propionic acid (120.1 mg, 33.1%) as a white solid: LC/MS m/e obsd. (ESI$^+$) [(M+H)$^+$] 364.2.

Example 21

N-[2-(6-Chloro-4,4-dimethyl-1,2,3,4-tetrahydro-quinolin-2-yl)-phenyl]-2-fluoro-benzenesulfonamide

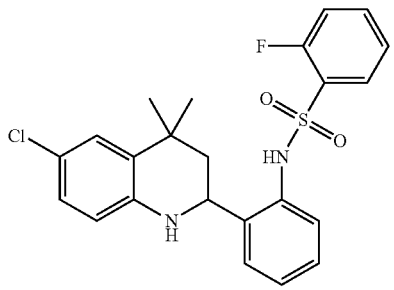 [SMILES: CC1(C)CC(c2ccccc2NS(=O)(=O)c2ccccc2F)Nc2ccc(Cl)cc21]

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and 2-fluorobenzenesulfonyl chloride (68 mg, 0.35 mmol) at ice-bath. The reaction mixture was stirred at room temperature overnight. The reaction mixture was washed with water. The aqueous layer was extracted with dichloromethane. The combined organic layer was washed by brine, dried over anhydrous sodium sulfate, concentrated in vacuo. The residue was purified by HPLC to give N-[2-(6-chloro-4,4-dimethyl-1,2,3,4-tetrahydro-quinolin-2-yl)-phenyl]-2-fluoro-benzenesulfonamide. LC/MS m/e obsd. (ESI$^+$) [(M+H)$^+$] 445.1.

Example 22

1-[2-(6-Chloro-4,4-dimethyl-1,2,3,4-tetrahydro-quinolin-2-yl)-phenylamino]-cyclopropanecarboxylic acid

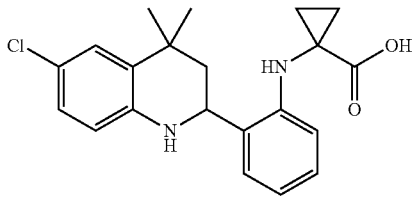 [SMILES: CC1(C)CC(c2ccccc2NC2(C(=O)O)CC2)Nc2ccc(Cl)cc21]

To a stirred solution of 4-chlorophenylamine (10.0 g, 78.4 mmol) and 2-bromobenzaldehyde (9.2 mL, 78.4 mmol) in acetonitrile (150 mL) were added isobutene (21.0 mL, 313.5 mmol) and ytterbium(III) trifluoromethanesulfonate (Yb(OTf)$_3$) (5.8 g, 9.5 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 0-10% ethyl acetate in petroleum ether) to afford 2-(2-bromo-phenyl)-6-chloro-4,4-dimethyl-1,2,3,4-tetrahydro-quinoline (11.0 g, 40.0%) as a light yellow solid: LC/MS m/e obsd. (ESI$^+$) [(M+H)$^+$] 350.0 & 352.0.

A solution of 2-(2-bromo-phenyl)-6-chloro-4,4-dimethyl-1,2,3,4-tetrahydro-quinoline (200 mg, 0.57 mmol), copper(I) iodide (33 mg, 0.17 mmol), 1-amino-cyclopropanecarboxylic acid (235 mg, 2.29 mmol) and potassium carbonate (240 mg, 1.7 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(6-chloro-4,4-dimethyl-1,2,3,4-tetrahydro-quinolin-2-yl)-phenylamino]-2-methyl-propionic acid (127 mg, 60.0%) as a white solid: LC/MS m/e obsd. (ESI$^+$) [(M+H)$^+$] 371.1.

Example 23

N-[2-(6-Cyano-4,4-dimethyl-1,2,3,4-tetrahydro-quinolin-2-yl)-phenyl]-methanesulfonamide

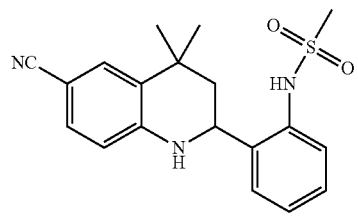 [SMILES: CC1(C)CC(c2ccccc2NS(C)(=O)=O)Nc2ccc(C#N)cc21]

The mixture of 4-aminobenzonitrile (20 g, 0.17 mol) and 2-nitrobenzaldehyde (28.2 g, 0.17 mol) in anhydrous ethanol was heated to reflux for 3 h. The reaction mixture was cooled to room temperature. The solvent was removed under reduced pressure. The residue was washed with diethyl ether to give 4-(2-nitrobenzylideneamino)benzonitrile as yellow solid (33.7 g, yield 79.3%) LC/MS m/e obsd. (ESI$^+$) [(M+H)$^+$] 252.10.

To a suspension of 4-(2-nitrobenzylideneamino)benzonitrile (20 g) and boron trifluoride etherate at 90° C. in sealed tube overnight. The solvent was removed under reduced pressure. The residue was purified by silica gel column chromatography to give 4,4-dimethyl-2-(2-nitrophenyl)-1,2,3,4-tetrahydroquinoline-6-carbonitrile as white solid (12 g, yield 48.9%) LC/MS m/e obsd. (ESI$^+$) [(M+H)$^+$] 308.2.

To a suspension of 4,4-dimethyl-2-(2-nitrophenyl)-1,2,3,4-tetrahydroquinoline-6-carbonitrile (2 g, 6.54 mmol) in saturated aqueous ammonium chloride and ethanol was added iron powder at room temperature. After addition, the resulting mixture was stirred at reflux under nitrogen for 3 h. The reaction mixture was cooled to room temperature and filtered through a pad of celite. The solvent of ethanol in filtrate was removed under reduced pressure and the water phase was extracted with ethyl acetate. The combined organic phase was dried, concentrated to give 2-(2-aminophenyl)-4,4-dimethyl-1,2,3,4-tetrahydroquinoline-6-carbonitrile as white solid (1 g, yield 56%). The product was used for the next step without further purification. LC/MS m/e obsd. (ESI$^+$) [(M+H)$^+$] 228.2.

To a solution of 2-(2-aminophenyl)-4,4-dimethyl-1,2,3,4-tetrahydroquinoline-6-carbonitrile (100 mg, 0.36 mmol) and pyridine (0.12 mL, 1.44 mmol) in anhydrous dichloromethane was added methanesulfonyl chloride (41.3 mg, 0.36 mmol) at ice-bath. After addition, the resulting mixture was stirred at room temperature for 3 h. The reaction mixture was diluted with water, and extracted with dichloromethane. The combined organic layer was dried over anhydrous sodium sulfate, concentrated. The residue was purified by prepared HPLC to give N-[2-(6-cyano-4,4-dimethyl-1,2,3,4-tetrahydro-quinolin-2-yl)-phenyl]-methanesulfonamide as white solid. LC/MS m/e obsd. (ESI$^+$) [(M+H)$^+$] 356.20.

Example 24

2-[3-(6-Cyano-1,4,4-trimethyl-1,2,3,4-tetrahydro-quinolin-2-yl)-phenylamino]-2-methyl-propionic acid

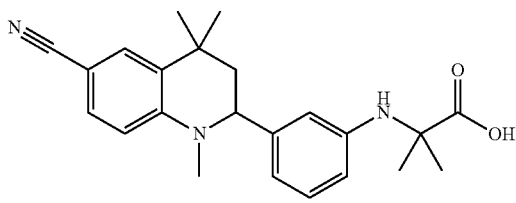 [SMILES: CN1c2ccc(C#N)cc2C(C)(C)CC1c1cccc(NC(C)(C)C(=O)O)c1]

To a stirred solution of 2-(3-bromo-phenyl)-4,4-dimethyl-1,2,3,4-tetrahydro-quinoline-6-carbonitrile (4.2 g, 12.4 mmol) in N,N-dimethylformamide (15 mL) was added a 60% dispersion of sodium hydride in mineral oil (1.5 g, 37.2 mmol) portionwise at 0° C. The mixture was stirred at 0° C. for 30 min and then iodomethane (2.4 mL, 37.2 mmol) was added to above mixture dropwise at 0° C. The solution was stirred at 0° C. for 2 h and then extracted with ethyl acetate, washed with brine, dried over anhydrous sodium sulfate and concentrated in vacuo. The yellowish residue was purified by ISCO combi-flash chromatography (gradient elution, 10% ethyl acetate/hexane) to afford 2-(3-bromo-phenyl)-1,4,4-trimethyl-1,2,3,4-tetrahydro-quinoline-6-carbonitrile (1.1 g, 70%) as a yellow oil: MS obsd. (ESI+) [(M+H)+] 355.0 & 357.0.

A solution of 2-(3-bromo-phenyl)-1,4,4-trimethyl-1,2,3,4-tetrahydro-quinoline-6-carbonitrile (354.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-cyano-1,4,4-trimethyl-1,2,3,4-tetrahydro-quinolin-2-yl)-phenylamino]-2-methyl-propionic acid (113.4 mg, 30.1%) as a white solid: LC/MS m/e obsd. (ESI+) [(M+H)+] 378.2.

Example 25

1-[2-(6-Cyano-4,4-dimethyl-1,2,3,4-tetrahydro-quinolin-2-yl)-phenylamino]-cyclopropanecarboxylic acid

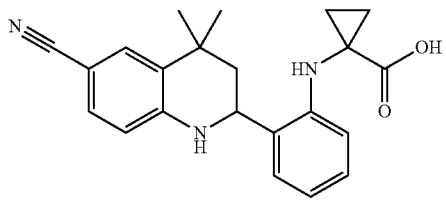 [SMILES: CC1(C)CC(c2ccccc2NC2(C(=O)O)CC2)Nc2ccc(C#N)cc21]

A solution of 2-(2-bromo-phenyl)-4,4-dimethyl-1,2,3,4-tetrahydro-quinoline-6-carbonitrile (341 mg, 1.0 mmol), copper(I) iodide (57.0 mg, 0.3 mmol), 1-amino-cyclopropanecarboxylic acid (235 mg, 4.0 mmol) and potassium carbonate (420 mg, 3.0 mmol) in dimethyl sulfoxide (4.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[2-(6-cyano-4,4-dimethyl-1,2,3,4-tetrahydro-quinolin-2-yl)-phenylamino]-cyclopropanecarboxylic acid (101.4 mg, 28.1%) as a white solid: LC/MS m/e obsd. (ESI+) [(M+H)+] 362.2.

Example 26

2-[2-(6-Chloro-4,4-dimethyl-1,2,3,4-tetrahydro-quinolin-2-yl)-phenylamino]-2-methyl-propionic acid

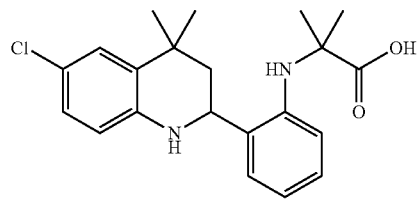 [SMILES: CC(C)(Nc1ccccc1C1CC(C)(C)c2cc(Cl)ccc2N1)C(=O)O]

A solution of 2-(2-bromo-phenyl)-6-chloro-4,4-dimethyl-1,2,3,4-tetrahydro-quinoline (200 mg, 0.57 mmol), copper(I) iodide (33 mg, 0.17 mmol), 2-amino-2-methyl-propionic acid (235 mg, 2.29 mmol) and potassium carbonate (240 mg, 1.7 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(6-chloro-4,4-dimethyl-1,2,3,4-tetrahydro-quinolin-2-yl)-phenylamino]-2-methyl-propionic acid (127 mg, 60.0%) as a white solid: LC/MS m/e obsd. (ESI+) [(M+H)+] 373.1.

Example 27

1-[3-(6-Fluoro-4,4,8-trimethyl-1,2,3,4-tetrahydro-quinolin-2-yl)-phenylamino]-cyclopropanecarboxylic acid

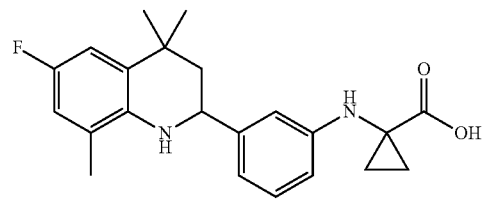 [SMILES: Cc1cc(F)cc2c1NC(c1cccc(NC3(C(=O)O)CC3)c1)CC2(C)C]

To a stirred solution of 4-fluoro-2-methyl-phenylamine (8.0 g, 64.0 mmol) and 3-bromobenzaldehyde (7.5 mL, 64.0 mmol) in acetonitrile (150 mL) were added isobutene (18.7 mL, 256.7 mmol) and ytterbium(III) trifluoromethanesulfonate (Yb(OTf)$_3$) (4.7 g, 7.7 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-6-fluoro-4,4,8-trimethyl-1,2,3,4-tetrahydro-quinoline (8.8 g, 40.0%) as a light yellow solid: LC/MS m/e obsd. (ESI$^+$) [(M+H)$^+$] 348.0 & 350.0.

A solution of 2-(3-bromo-phenyl)-6-fluoro-4,4,8-trimethyl-1,2,3,4-tetrahydro-quinoline (348.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-fluoro-4,4,8-trimethyl-1,2,3,4-tetrahydro-quinolin-2-yl)-phenylamino]-cyclopropanecarboxylic acid (104.8 mg, 30.1%) as a white solid: LC/MS m/e obsd. (ESI$^+$) [(M+H)$^+$] 369.2.

Example 28

1-[3-(6-Cyano-1,4,4-trimethyl-1,2,3,4-tetrahydro-quinolin-2-yl)-phenylamino]-cyclopropanecarboxylic acid

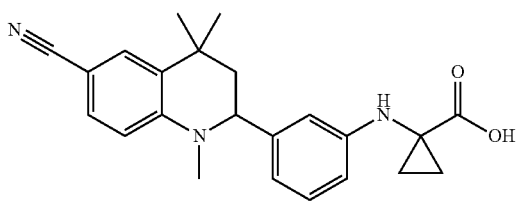 [SMILES: CN1c2ccc(C#N)cc2C(C)(C)CC1c1cccc(NC2(C(=O)O)CC2)c1]

A solution of 2-(3-bromo-phenyl)-1,4,4-trimethyl-1,2,3,4-tetrahydro-quinoline-6-carbonitrile (354.0 mg, 1.0 mmol), copper(I) iodide (57.0 mg, 0.3 mmol), 1-amino-cyclopropanecarboxylic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-[3-(6-cyano-1,4,4-trimethyl-1,2,3,4-tetrahydro-quinolin-2-yl)-phenylamino]-cyclopropanecarboxylic acid (113.4 mg, 30.1%) as a white solid: LC/MS m/e obsd. (ESI$^+$) [(M+H)$^+$] 376.3.

Example 29

2-[3-(8-Chloro-6-cyano-4,4-dimethyl-1,2,3,4-tetrahydro-quinolin-2-yl)-phenylamino]-2-methyl-propionic acid

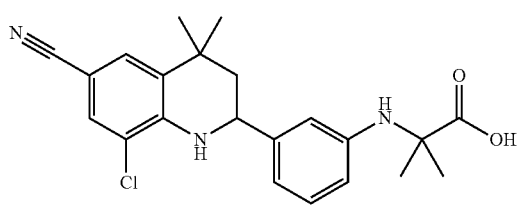 [SMILES: CC(C)(Nc1cccc(C2CC(C)(C)c3cc(C#N)cc(Cl)c3N2)c1)C(=O)O]

A solution of 2-(3-bromo-phenyl)-8-chloro-4,4-dimethyl-1,2,3,4-tetrahydro-quinoline-6-carbonitrile (374.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(8-chloro-6-cyano-4,4-dimethyl-1,2,3,4-tetrahydro-quinolin-2-yl)-phenylamino]-2-methylpropionic acid (118.8 mg, 30%) as a white solid: LC/MS m/e obsd. (ESI$^+$) [(M+H)$^+$] 398.2.

Example 30

2-Methyl-2-[3-(4,4,6-trimethyl-1,2,3,4-tetrahydro-quinolin-2-yl)-phenylamino]-propionic acid

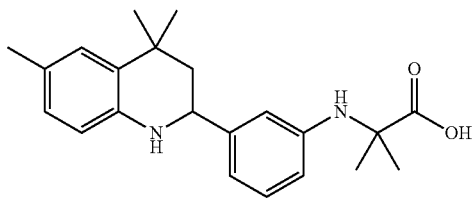 [SMILES: Cc1ccc2c(c1)C(C)(C)CC(c1cccc(NC(C)(C)C(=O)O)c1)N2]

To a stirred solution of 4-methyl-phenylamine (6.8 g, 64.0 mmol) and 3-bromobenzaldehyde (7.5 mL, 64.0 mmol) in acetonitrile (150 mL) were added isobutene (18.7 mmol) and ytterbium(III) trifluoromethanesulfonate (Yb(OTf)$_3$) (4.7 g, 7.7 mmol). The resulting mixture was stirred at 85° C. for 18 h in sealed tube. The mixture was diluted with ethyl acetate (300 mL) and washed with water (100 mL×2) and brine (100 mL×2) and then dried over anhydrous sodium sulfate. The solvent was removed in vacuo and the residue was purified by ISCO combi-flash chromatography (gradient elution, 10-50% ethyl acetate in petroleum ether) to afford 2-(3-bromo-phenyl)-4,4,6-trimethyl-1,2,3,4-tetrahydro-quinoline (8.5 g, 40.0%) as a light yellow solid: LC/MS m/e obsd. (ESI$^+$) [(M+H)$^+$] 330.0 & 332.0.

A solution of 2-(3-bromo-phenyl)-4,4,6-trimethyl-1,2,3,4-tetrahydro-quinoline (329.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) 2-methyl-2-[3-(4,4,6-trimethyl-1,2,3,4-tetrahydro-quinolin-2-yl)-phenylamino]-propionic acid (104.8 mg, 29%) as a white solid: LC/MS m/e obsd. (ESI$^+$) [(M+H)$^+$] 353.1.

Example 31

2-[3-(6-Fluoro-4,4,8-trimethyl-1,2,3,4-tetrahydro-quinolin-2-yl)-phenylamino]-2-methyl-propionic acid

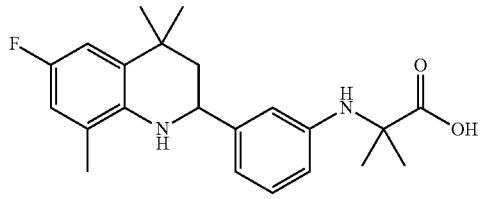 [SMILES: Cc1cc(F)cc2c1NC(c1cccc(NC(C)(C)C(=O)O)c1)CC2(C)C]

A solution of 2-(3-bromo-phenyl)-6-fluoro-4,4,8-trimethyl-1,2,3,4-tetrahydro-quinoline (348.0 mg, 1.0 mmol), copper(I) iodide (57.0 mg, 0.3 mmol), 2-amino-2-methyl-propionic acid (309.0 mg, 3.0 mmol) and potassium carbonate (415.0 mg, 3.0 mmol) in dimethyl sulfoxide (2.0 mL) was stirred at 120° C. for 16 h. Then the reaction mixture was cooled to room temperature and extracted with ethyl acetate (150 mL×2), washed with water (50 mL×2) and saturated aqueous ammonium chloride solution (50 mL×2), dried over anhydrous sodium sulfate and then concentrated in vacuo. Purification by Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[3-(6-fluoro-4,4,8-trimethyl-1,2,3,4-tetrahydro-quinolin-2-yl)-phenylamino]-2-methyl-propionic acid (104.8 mg, 30.1%) as a white solid: LC/MS m/e obsd. (ESI$^+$) [(M+H)$^+$] 371.2.

Example 32

2-[2-(4-Fluoro-benzoylamino)-phenyl]-4,4-dimethyl-1,2,3,4-tetrahydro-quinoline-6-carboxylic acid

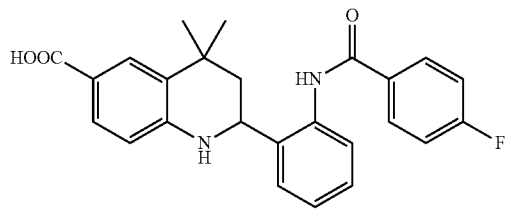 [SMILES: CC1(C)CC(c2ccccc2NC(=O)c2ccc(F)cc2)Nc2ccc(C(=O)O)cc21]

To a solution of ethyl-4-aminobenzoate (5.0 g, 30.3 mmol) in ethanol was added 2-nitrobenzaldehyde (5.03, 33.3 mmol) at room temperature. The reaction mixture was stirred at reflux for 3 h LC-MS showed ester was consumed nearly. The reaction mixture was concentrated in vacuo. The residue was washed by diethyl ether to give ethyl 4-(2-nitrobenzylidene-amino)benzoate as yellow solid (7.8 g, yield 86.4%). LC/MS m/e obsd. (ESI$^+$) [(M+H)$^+$] 299.2.

To a solution of ethyl 4-(2-nitrobenzylideneamino)benzoate (18.67 g, 62.6 mmol) in acetonitrile was added 2-methylpropene (80 mL, pre-cooled to −78° C.) and boron trifluoride etherate (1 mL) at ice-bath. The reaction mixture was stirred at 90° C. for 18 h in sealed tube. The reaction mixture was concentrated in vacuo. The residue was purified by flash column chromatography to give ethyl 4,4-dimethyl-2-(2-nitrophenyl)-1,2,3,4-tetrahydroquinoline-6-carboxylate as yellow solid (13.4 g, yield 60.4%). %). LC/MS m/e obsd. (ESI$^+$) [(M+H)$^+$] 355.1.

To a stirred suspension of ethyl 4,4-dimethyl-2-(2-nitrophenyl)-1,2,3,4-tetrahydroquinoline-6-carboxylate (13.0 g, 36.7 mmol) in ethanol was added iron powder (8.2 g, 146.7 mmol) and saturated aqueous ammonium chloride sat room temperature, the reaction mixture was stirred at 90° C. for 3 h. The insoluble solid was filtered off and filtrated was concentrated in vacuum and the residue was extracted with ethyl acetate, dried over anhydrous sodium sulfate and concentrated in vacuum. The residue was purified by column chromatography to give ethyl 2-(2-aminophenyl)-4,4-dimethyl-1,2,3,4-tetrahydroquinoline-6-carboxylate as yellow solid (5.4 g, yield 45.4%). LC/MS m/e obsd. (ESI$^+$) [(M+H)$^+$] 325.1.

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 4-fluorobenzoyl chloride (120 mg, 0.62 mmol) at ice-bath. The reaction mixture was washed with water. The aqueous layer was extracted with dichloromethane. The combined organic layer was washed brine, dried over anhydrous sodium sulfate, concentrated in vacuo. The residue was used in next step. LC/MS m/e obsd. (ESI$^+$) [(M+H)$^+$] 447.2.

To a stirred solution of ethyl 2-(2-(4-fluorobenzamido)phenyl)-4,4-dimethyl-1,2,3,4-tetrahydroquinoline-6-carboxylate (about 0.62 mmol) in ethanol was added a solution of lithium hydroxide monohydrate (129 mg, 3.08 mmol) and sodium hydroxide (50 mg, 1.23 mmol) in water at room temperature. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous sodium sulfate, concentrated in vacuo. The residue was purified by HPLC to give 2-[2-(4-fluoro-benzoylamino)-phenyl]-4,4-dimethyl-1,2,3,4-tetrahydro-quinoline-6-carboxylic acid LC/MS m/e obsd. (ESI+) [(M+H)+] 419.10.

Example 33

2-(2-Ethanesulfonylamino-phenyl)-4,4-dimethyl-1,2,3,4-tetrahydro-quinoline-6-carboxylic acid

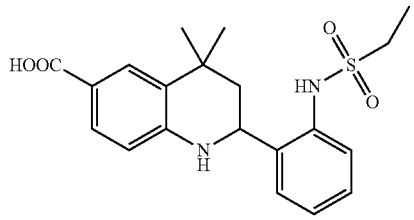 [SMILES: CCS(=O)(=O)Nc1ccccc1C1CC(C)(C)c2cc(C(=O)O)ccc2N1]

To a stirred solution of ethyl 2-(2-aminophenyl)-4,4-dimethyl-1,2,3,4-tetrahydroquinoline-6-carboxylate (200 mg, 0.62 mmol) in dichloromethane was added pyridine (0.6 mL) and ethanesulfonyl chloride (80 mg, 0.62 mmol) at ice-bath. The reaction mixture was stirred at room temperature for 6 h. The reaction mixture was washed with water. The aqueous layer was extracted with dichloromethane. The combined organic layer was washed with brine, dried over anhydrous Sodium sulfate, concentrated under vacuo. The residue was used in next step. LC/MS m/e obsd. (ESI+) [(M+H)+] 417.1.

To a stirred solution of ethyl 2-(2-(ethylsulfonamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous sodium sulfate, concentrated in vacuo. The residue was purified by HPLC to give 2-(2-ethanesulfonylamino-phenyl)-4,4-dimethyl-1,2,3,4-tetrahydro-quinoline-6-carboxylic acid. LC/MS m/e obsd. (ESI+) [(M+H)+] 389.0.

Example 34

4,4-Dimethyl-2-[2-(pyridine-3-sulfonylamino)-phenyl]-1,2,3,4-tetrahydro-quinoline-6-carboxylic acid

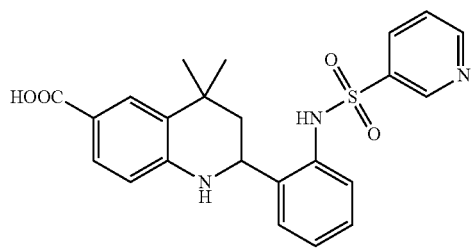 [SMILES: CC1(C)CC(c2ccccc2NS(=O)(=O)c2cccnc2)Nc2ccc(C(=O)O)cc21]

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and pyridine-3-sulfonyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuum. The residue was used in next step. LC/MS m/e obsd. (ESI+) [(M+H)+] 466.2.

To a stirred solution of ethyl 4,4-dimethyl-2-(2-(pyridine-3-sulfonamido)phenyl)-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous Sodium sulfate, concentrated in vacuo. The residue was purified by HPLC to give 4,4-dimethyl-2-[2-(pyridine-3-sulfonylamino)-phenyl]-1,2,3,4-tetrahydro-quinoline-6-carboxylic acid. LC/MS m/e obsd. (ESI+) [(M+H)+] 438.20.

Example 35

2-[2-(2-Fluoro-benzoylamino)-phenyl]-4,4-dimethyl-1,2,3,4-tetrahydro-quinoline-6-carboxylic acid

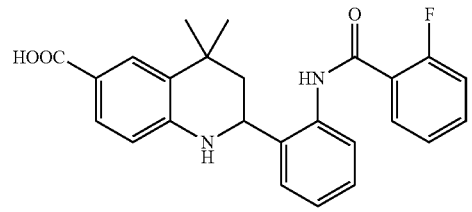 [SMILES: CC1(C)CC(c2ccccc2NC(=O)c2ccccc2F)Nc2ccc(C(=O)O)cc21]

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 2-fluorobenzoyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuum. The residue was used for the next step without further purification. LC/MS m/e obsd. (ESI+) [(M+H)+] 447.2.

To a stirred solution of ethyl 2-(2-(2-fluorobenzamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous sodium sulfate, concentrated in vacuo. The residue was purified by HPLC to give 2-[2-(2-fluoro-benzoylamino)- phenyl]-4,4-dimethyl-1,2,3,4-tetrahydro-quinoline-6-carboxylic acid. LC/MS m/e obsd. (ESI⁺) [(M+H)⁺] 419.30.

Example 36

Pyridine-3-sulfonic acid [2-(6-chloro-4,4-dimethyl-1,2,3,4-tetrahydro-quinolin-2-yl)-phenyl]-amide

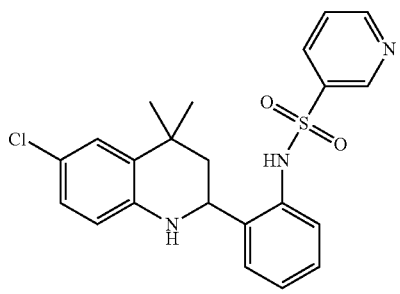 [SMILES: CC1(C)CC(c2ccccc2NS(=O)(=O)c2cccnc2)Nc2ccc(Cl)cc21]

To a stirred solution of 2-(6-chloro-4,4-dimethyl-1,2,3,4-tetrahydroquinolin-2-yl)aniline (100 mg, 0.35 mmol) in dichloromethane (5 mL) was added pyridine (0.6 mL) and pyridine-3-sulfonyl chloride (112 mg, 0.35 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuum. The residue was purified by HPLC to give pyridine-3-sulfonic acid [2-(6-chloro-4,4-dimethyl-1,2,3,4-tetrahydro-quinolin-2-yl)-phenyl]-amide. LC/MS m/e obsd. (ESI⁺) [(M+H)⁺] 427.90.

Example 37

2-[2-(3-Fluoro-benzoylamino)-phenyl]-4,4-dimethyl-1,2,3,4-tetrahydro-quinoline-6-carboxylic acid

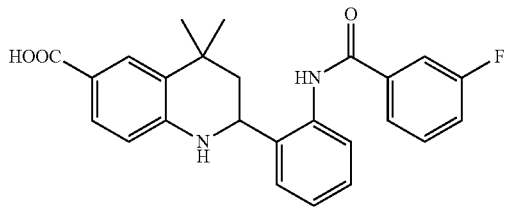 [SMILES: CC1(C)CC(c2ccccc2NC(=O)c2cccc(F)c2)Nc2ccc(C(=O)O)cc21]

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 3-fluorobenzoyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuum. The residue was used for the next step. LC/MS m/e obsd. (ESI⁺) [(M+H)⁺] 447.1.

To a stirred solution of ethyl 2-(2-(3-fluorobenzamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous Sodium sulfate, concentrated in vacuo. The residue was purified by HPLC to give 2-[2-(3-fluoro-benzoylamino)-phenyl]-4,4-dimethyl-1,2,3,4-tetrahydro-quinoline-6-carboxylic acid. LC/MS m/e obsd. (ESI⁻) [(M–H)⁻] 417.30.

Example 38

N-[2-(6-Chloro-4,4-dimethyl-1,2,3,4-tetrahydro-quinolin-2-yl)-phenyl]-benzenesulfonamide

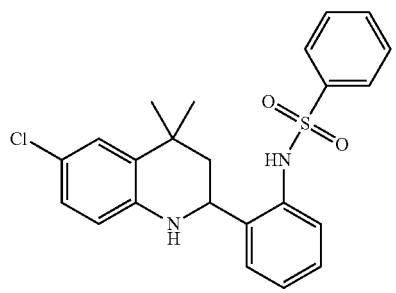 [SMILES: CC1(C)CC(c2ccccc2NS(=O)(=O)c2ccccc2)Nc2ccc(Cl)cc21]

To a stirred solution of 2-(6-chloro-4,4-dimethyl-1,2,3,4-tetrahydroquinolin-2-yl)aniline (100 mg, 0.35 mmol) in dichloromethane (5 mL) was added triethylamine (100 mg) and benzenesulfonyl chloride (60.2 mg, 0.35 mmol) at ice-bath. The reaction mixture was stirred at room temperature for 4 h. The reaction mixture was washed with water. The aqueous layer was extracted with dichloromethane. The combined organic layer was washed by brine, dried over anhydrous sodium sulfate, concentrated in vacuo. The residue was purified by HPLC to give N-[2-(6-chloro-4,4-dimethyl-1,2,3,4-tetrahydro-quinolin-2-yl)-phenyl]-benzenesulfonamide LC/MS m/e obsd. (ESI⁺) [(M+H)⁺] 427.20.

Example 39

2-[2-(2-Fluoro-benzenesulfonylamino)-phenyl]-4,4-dimethyl-1,2,3,4-tetrahydro-quinoline-6-carboxylic acid

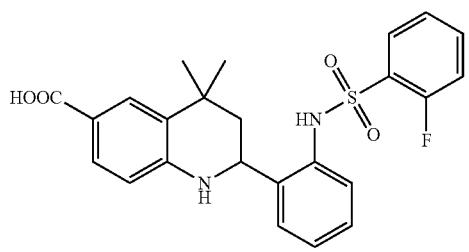 [SMILES: CC1(C)CC(c2ccccc2NS(=O)(=O)c2ccccc2F)Nc2ccc(C(=O)O)cc21]

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 2-fluorobenzene-1-sulfonyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuo. The residue was used in next step. LC/MS m/e obsd. (ESI$^+$) [(M+H)$^+$] 483.2.

To a stirred solution of ethyl 2-(2-(2-fluorophenylsulfonamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous Sodium sulfate, concentrated in vacuo. The residue was purified by HPLC to give 2-[2-(2-fluoro-benzenesulfonylamino)-phenyl]-4,4-dimethyl-1,2,3,4-tetrahydro-quinoline-6-carboxylic acid LC/MS m/e obsd. (ESI$^+$) [(M+H)$^+$] 455.20.

Example 40

2-[2-(4-Fluoro-benzenesulfonylamino)-phenyl]-4,4-dimethyl-1,2,3,4-tetrahydro-quinoline-6carboxylic acid

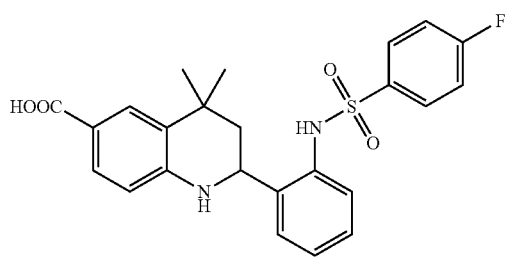 [SMILES: CC1(C)CC(c2ccccc2NS(=O)(=O)c2ccc(F)cc2)Nc2ccc(C(=O)O)cc21]

To a stirred solution of ethyl 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 4-fluorobenzene-1-sulfonyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuo. The residue was used in next step. LC/MS m/e obsd. (ESI$^+$) [(M+H)$^+$] 483.2.

To a stirred solution of ethyl 2-(2-(4-fluorophenylsulfonamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous Sodium sulfate, concentrated in vacuo. The residue was purified by HPLC to give 2-[2-(4-fluoro-benzenesulfonylamino)-phenyl]-4,4-dimethyl-1,2,3,4-tetrahydro-quinoline-6-carboxylic acid. LC/MS m/e obsd. (ESI$^+$) [(M+H)$^+$] 455.20.

Example 41

2-(2-Benzenesulfonylamino-phenyl)-4,4-dimethyl-1,2,3,4-tetrahydro-quinoline-6-carboxylic acid

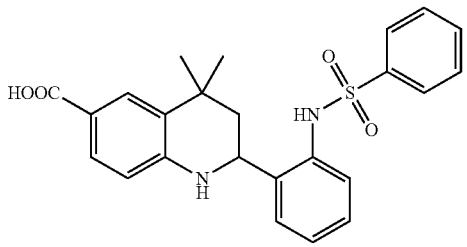 [SMILES: CC1(C)CC(c2ccccc2NS(=O)(=O)c2ccccc2)Nc2ccc(C(=O)O)cc21]

To a stirred solution of 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and benzenesulfonyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous Sodium sulfate, concentrated in vacuo. The residue was used in next step. LC/MS m/e obsd. (ESI$^+$) [(M+H)$^+$] 465.2.

To a stirred solution of ethyl 4,4-dimethyl-2-(2-(phenylsulfonamido)phenyl)-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature. The reaction mixture was stirred at 85° C. overnight. The reaction mixture was concentrated in vacuo. The residue was diluted with water, adjusted pH=3~4 by 1M aqueous hydrochloric acid, extracted with ethyl acetate. The combined organic layer was washed by brine, dried over anhydrous sodium sulfate, concentrated in vacuo. The residue was purified by HPLC to give 2-(2-benzenesulfonylamino-phenyl)-4,4-dimethyl-1,2,3,4-tetrahydro-quinoline-6-carboxylic acid. LC/MS m/e obsd. (ESI$^+$) [(M+H)$^+$] 437.30.

Example 42

2-[2-(3-Fluoro-benzenesulfonylamino)-phenyl]-4,4-dimethyl-1,2,3,4-tetrahydro-quinoline-6-carboxylic acid

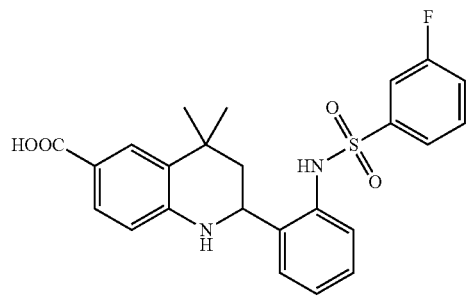 [SMILES: CC1(C)CC(c2ccccc2NS(=O)(=O)c2cccc(F)c2)Nc2ccc(C(=O)O)cc21]

To a stirred solution of 2-(2-aminophenyl)-4,4-dimethyl-1,2,3,4-tetrahydroquinoline-6-carboxylate (200 mg, 0.62 mmol) in dichloromethane (5 mL) was added pyridine (0.6 mL) and 3-fluorobenzene-1-sulfonyl chloride (120 mg, 0.62 mmol) at ice-bath. The reaction mixture was stirred at room temperature for 6 h. The reaction mixture was washed with water. The aqueous layer was extracted with dichloromethane. The combined organic layer was washed by brine, dried over anhydrous sodium sulfate, concentrated in vacuo. The residue was used for next step without further purification. LC/MS m/e obsd. (ESI$^+$) [(M+H)$^+$] 483.2.

To a stirred solution of ethyl 2-(2-(3-fluorophenylsulfonamido)phenyl)-4,4-dimethyl-1,2,3,4-tetrahydroquinoline-6-carboxylate (crude 0.62 mmol) in ethanol was added a solution of lithium hydroxide monohydrate (129 mg, 3.08 mmol) and sodium hydroxide (50 mg, 1.23 mmol) in water (1.5 mL) at room temperature, the reaction mixture was stirred at 85° C. overnight. The residue was diluted with water, adjusted pH=3~4 by 1M aqueous hydrochloric acid, extracted with ethyl acetate. The combined organic layer was washed by brine, dried over anhydrous sodium sulfate, concentrated in vacuo. The residue was purified by HPLC to give 2-[2-(3-fluoro-benzenesulfonylamino)-phenyl]-4,4-dimethyl-1,2,3,4-tetrahydro-quinoline-6-carboxylic acid. LC/MS m/e obsd. (ESI$^+$) [(M+H)$^+$] 455.20.

Example 43

N-[2-(4,4-Dimethyl-6-trifluoromethyl-1,2,3,4-tetrahydro-quinolin-2-yl)-phenyl]-3-fluoro-benzenesulfonamide

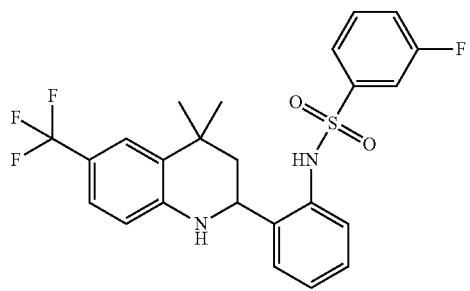 [SMILES: CC1(C)CC(c2ccccc2NS(=O)(=O)c2cccc(F)c2)Nc2ccc(C(F)(F)F)cc21]

A mixture of 4-(trifluoromethyl)aniline (5 g) and 2-nitrobenzaldehyde (5.2 g) in anhydrous ethanol was heated to reflux for 3 h; the reaction mixture was cooled to room temperature. The solvent was removed under reduced pressure. The residue was washed with diethyl ether and petro-ether to give N-(2-nitrobenzylidene)-4-(trifluoromethyl)aniline as yellow solid (6.6 g, yield 72.3%). LC/MS m/e obsd. (ESI$^+$) [(M+H)$^+$] 295.1.

To a suspension of N-(2-nitrobenzylidene)-4-(trifluoromethyl)aniline (2.7 g, 9.18 mmol) and Borontrifluoride etherate (289 µL) in anhydrous acetonitrile was added isobutene (16 mL, pre-cooled to −78° C.) at ice-bath. After addition, the resulting mixture was stirred at 90° C. in sealed tube overnight. The solvent was removed under reduced pressure. The residue was purified by silica gel column chromatography to give 4,4-dimethyl-2-(2-nitrophenyl)-6-(trifluoromethyl)-1,2,3,4-tetrahydroquinoline (2.56 g, yield 80%). LC/MS m/e obsd. (ESI$^+$) [(M+H)$^+$] 351.1.

To a suspension of 4,4-dimethyl-2-(2-nitrophenyl)-6-(trifluoromethyl)-1,2,3,4-tetrahydroquinoline (2.56 g, 7.3 mmol) in saturated aqueous ammonium chloride (20 mL) and ethanol (30 mL) was added iron powder (1.2 g, 21.0 mmol) at room temperature After addition, the resulting mixture was stirred at reflux under Nitrogen for 3 h. The reaction mixture was cooled to room temperature and filtered through a pad of celite. The solvent of ethanol in filtrate was removed under reduced pressure and the water phase was extracted with ethyl acetate. The combined organic phase was dried, concentrated to give 2-(4,4-dimethyl-6-(trifluoromethyl)-1,2,3,4-tetrahydroquinolin-2-yl)aniline. The product was used in the next step without further purification. LC/MS m/e obsd. (ESI$^+$) [(M+H)$^+$] 321.1.

To a solution of 2-(4,4-dimethyl-6-(trifluoromethyl)-1,2,3,4-tetrahydroquinolin-2-yl)aniline (150 mg, 0.47 mmol) and pyridine (148 mg, 1.44 mmol) in anhydrous dichloromethane (5 mL) was added a solution of 3-fluorobenzene-1-sulfonyl chloride (92 mg, 0.36 mmol) at ice-bath. After addition, the resulting mixture was stirred at room temperature for 3 h. The reaction mixture was diluted with water, and extracted with dichloromethane. The combined organic layer was dried over anhydrous Sodium sulfate, concentrated. The residue was purified by HPLC to give N-[2-(4,4-dimethyl-6-trifluoromethyl-1,2,3,4-tetrahydro-quinolin-2-yl)-phenyl]-3-fluoro-benzenesulfonamide LC/MS m/e obsd. (ESI$^+$) [(M+H)$^+$] 478.90.

Example 44

N-[2-(4,4-Dimethyl-6-trifluoromethyl-1,2,3,4-tetrahydro-quinolin-2-yl)-phenyl]-2-fluoro-benzenesulfonamide

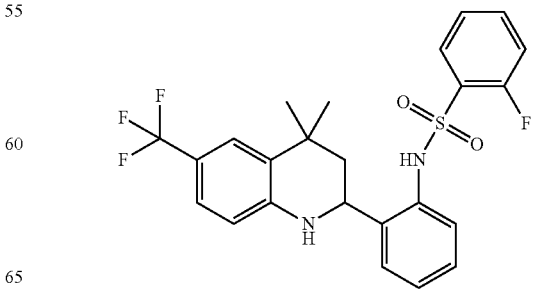

To a solution of 2-(4,4-dimethyl-6-(trifluoromethyl)-1,2,3,4-tetrahydroquinolin-2-yl)aniline (100 mg, 0.36 mmol) and pyridine (114 mg, 1.44 mmol) in anhydrous dichloromethane (5 mL) was added 2-fluorobenzene-1-sulfonyl chloride (70.1 mg, 0.36 mmol) at ice-bath. After addition, the resulting mixture was stirred at room temperature for 3 h. The reaction mixture was diluted with water, and extracted with dichloromethane. The combined organic layer was dried over anhydrous sodium sulfate, concentrated. The residue was purified by HPLC to give N-(2-(4,4-dimethyl-6-(trifluoromethyl)-1,2,3,4-tetrahydroquinolin-2-yl)phenyl)-2-fluorobenzenesulfonamide. LC/MS m/e obsd. (ESI$^+$) [(M+H)$^+$] 478.90.

Example 45

N-[2-(4,4-Dimethyl-6-trifluoromethyl-1,2,3,4-tetrahydro-quinolin-2-yl)-phenyl]-4-fluoro-benzenesulfonamide

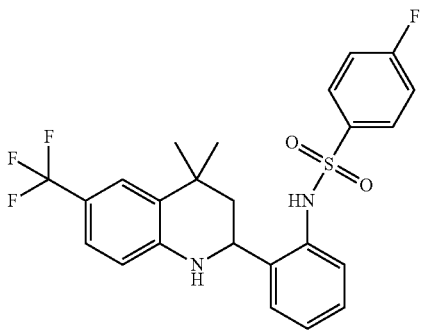 [SMILES: CC1(C)CC(c2ccccc2NS(=O)(=O)c2ccc(F)cc2)Nc2ccc(C(F)(F)F)cc21]

To a solution of 2-(4,4-dimethyl-6-(trifluoromethyl)-1,2,3,4-tetrahydroquinolin-2-yl)aniline (100 mg, 0.36 mmol) and pyridine (114 mg, 1.44 mmol) in anhydrous dichloromethane (5 mL) was added 4-fluorobenzene-1-sulfonyl chloride (70.1 mg, 0.36 mmol) at ice-bath. After addition, the resulting mixture was stirred at room temperature for 3 h. The reaction mixture was diluted with water, and extracted with dichloromethane. The combined organic layer was dried over anhydrous Sodium sulfate, concentrated. The residue was purified by HPLC to give N-[2-(4,4-dimethyl-6-trifluoromethyl-1,2,3,4-tetrahydro-quinolin-2-yl)-phenyl]-4-fluoro-benzenesulfonamide LC/MS m/e obsd. (ESI$^+$) [(M+H)$^+$] 478.9.

Example 46

Ethanesulfonic acid [2-(4,4-dimethyl-6-trifluoromethyl-1,2,3,4-tetrahydro-quinolin-2-yl)-phenyl]-amide

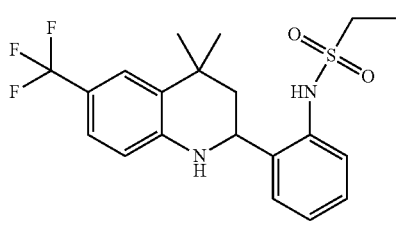 [SMILES: CCS(=O)(=O)Nc1ccccc1C1CC(C)(C)c2cc(C(F)(F)F)ccc2N1]

To a solution of 2-(4,4-dimethyl-6-(trifluoromethyl)-1,2,3,4-tetrahydroquinolin-2-yl)aniline (150 mg) and pyridine (200 μL) in dichloromethane (3 mL) was added ethanesulfonylchloride (44 μL) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, concentrated. The residue was purified by HPLC to give ethanesulfonic acid [2-(4,4-dimethyl-6-trifluoromethyl-1,2,3,4-tetrahydro-quinolin-2-yl)-phenyl]-amide. LC/MS m/e obsd. (ESI$^+$) [(M+H)$^+$] 412.9.

Example 47

N-[2-(4,4-Dimethyl-6-trifluoromethyl-1,2,3,4-tetrahydro-quinolin-2-yl)-phenyl]-benzenesulfonamide

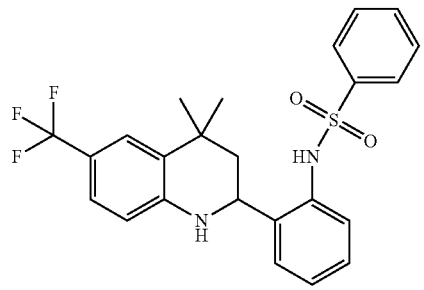 [SMILES: CC1(C)CC(c2ccccc2NS(=O)(=O)c2ccccc2)Nc2ccc(C(F)(F)F)cc21]

To a solution of 2-(4,4-dimethyl-6-(trifluoromethyl)-1,2,3,4-tetrahydroquinolin-2-yl)aniline (150 mg) and pyridine (3 mL) was added benzenesulfonyl chloride (60 μL) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, concentrated. The residue was purified by HPLC to give N-[2-(4,4-dimethyl-6-trifluoromethyl-1,2,3,4-tetrahydro-quinolin-2-yl)-phenyl]-benzenesulfonamide. LC/MS m/e obsd. (ESI$^-$) [(M−H)$^-$] 459.3.

Example 48

N-[2-(4,4-Dimethyl-6-trifluoromethyl-1,2,3,4-tetrahydro-quinolin-2-yl)-phenyl]-methanesulfonamide

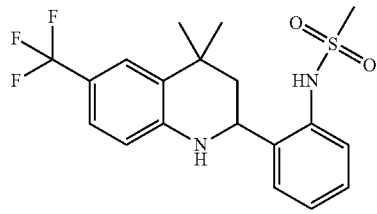 [SMILES: CC1(C)CC(c2ccccc2NS(C)(=O)=O)Nc2ccc(C(F)(F)F)cc21]

To a solution of 2-(4,4-dimethyl-6-(trifluoromethyl)-1,2,3,4-tetrahydroquinolin-2-yl)aniline (150 mg) and pyridine (1 mL) in anhydrous dichloromethane (3 mL) was added methanesulfonyl chloride (36 μL) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, concentrated. The residue was purified by HPLC to give N-[2-(4,4-dimethyl-6- trifluoromethyl-1,2,3,4-tetrahydro-quinolin-2-yl)-phenyl]-methanesulfonamide LC/MS m/e obsd. (ESI$^+$) [(M+H)$^+$] 399.6.

Example 49

N-[2-(6-Cyano-4,4-dimethyl-1,2,3,4-tetrahydro-quinolin-2-yl)-phenyl]-benzenesulfonamide

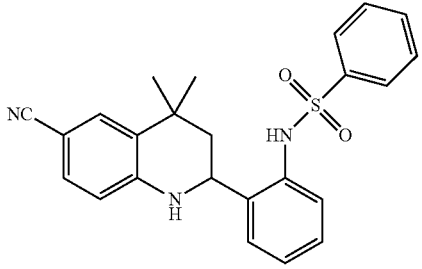 [SMILES: CC1(C)CC(c2ccccc2NS(=O)(=O)c2ccccc2)Nc2ccc(C#N)cc21]

To a solution of 2-(2-aminophenyl)-4,4-dimethyl-1,2,3,4-tetrahydroquinoline-6-carbonitrile (500 mg, 1.8 mmol) in pyridine (3 mL) was added benzenesulfonyl chloride (230 μL, 1.8 mmol) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, concentrated. The residue was purified by HPLC to give N-[2-(6-cyano-4,4-dimethyl-1,2,3,4-tetrahydro-quinolin-2-yl)-phenyl]-benzenesulfonamide. LC/MS m/e obsd. (ESI$^+$) [(M+H)$^+$] 418.2.

Example 50

Propane-2-sulfonic acid [2-(6-cyano-4,4-dimethyl-1,2,3,4-tetrahydro-quinolin-2-yl)-phenyl]-amide

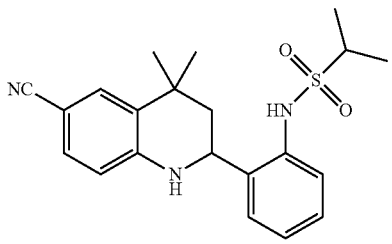 [SMILES: CC(C)S(=O)(=O)Nc1ccccc1C1CC(C)(C)c2cc(C#N)ccc2N1]

To a solution of 2-(2-aminophenyl)-4,4-dimethyl-1,2,3,4-tetrahydroquinoline-6-carbonitrile (500 mg, 1.8 mmol) in pyridine (3 mL) was added propane-2-sulfonyl chloride (201 μL, 1.8 mmol) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, concentrated. The residue was purified by HPLC to give propane-2-sulfonic acid [2-(6-cyano-4,4-dimethyl-1,2,3,4-tetrahydro-quinolin-2-yl)-phenyl]-amide LC/MS m/e obsd. (ESI$^+$) [(M+H)$^+$] 384.3.

Example 51

N-[2-(4,4,6-Trimethyl-1,2,3,4-tetrahydro-quinolin-2-yl)-phenyl]-benzensulfonamide

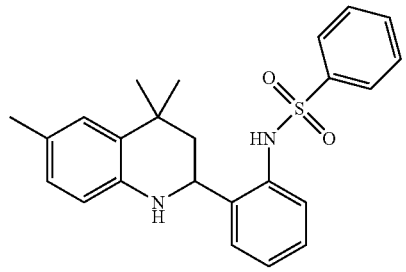 [SMILES: Cc1ccc2c(c1)C(C)(C)CC(c1ccccc1NS(=O)(=O)c1ccccc1)N2]

The mixture of p-toluidine (10 g) and 2-nitrobenzaldehyde (14.1 g) in anhydrous ethanol was heated to reflux for 3 h. The reaction mixture was cooled to room temperature. The solvent was removed under reduced pressure. The residue was washed with diethyl ether and petro ether to give 4-methyl-N-(2-nitrobenzylidene)aniline as yellow solid (17.3 g, yield 77.2%). LC/MS m/e obsd. (ESI$^+$) [(M+H)$^+$] 241.2.

To a suspension of 4-methyl-N-(2-nitrobenzylidene)aniline (10 g) and boron trifluoride etherate (3 mL) in anhydrous acetonitrile was added isobutene (70 mL, pre-cooled to −78° C.) at ice-bath. After addition, the resulting mixture was stirred at 90° C. in sealed tube overnight. The solvent was removed under reduced pressure. The residue was purified by silica gel column chromatography to give 4,4,6-trimethyl-2-(2-nitrophenyl)-1,2,3,4-tetrahydroquinoline (10.5 g, yield 85.4%). LC/MS m/e obsd. (ESI$^+$) [(M+H)$^+$] 297.2.

To a suspension of 4,4,6-trimethyl-2-(2-nitrophenyl)-1,2,3,4-tetrahydroquinoline (12.3 g, 40 mmol) in saturated aqueous ammonium chloride and ethanol (100 mL) was added powder iron (9.3 g, 160 mmol) at room temperature. After addition, the resulting mixture was stirred at reflux under nitrogen for 3 h. The reaction mixture was cooled to room temperature; and filtered through a pad of celite. The solvent of ethanol in filtrate was removed under reduced pressure and the water phase was extracted with ethyl acetate. The combined organic phase was dried, concentrated to give 2-(4,4,6-trimethyl-1,2,3,4-tetrahydroquinolin-2-yl)aniline (9.7 g). The product was used in the next step without further purification. LC/MS m/e obsd. (ESI$^+$) [(M+H)$^+$] 267.1.

To a solution of 2-(4,4,6-trimethyl-1,2,3,4-tetrahydro-quinolin-2-yl)aniline (150 mg, 0.56 mmol) and pyridine (0.5 mL) in dichloromethane (2 mL) was added benzenesulfonyl chloride (72 μL) at ice-bath under nitrogen. After addition, the resulting mixture was stirred at room temperature for 3 h. The reaction mixture was diluted with water, and extracted with ethyl acetate. The combined organic layer was dried over anhydrous Sodium sulfate, removed the solvent under reduced pressure, the residue was purified by HPLC to give N-[2-(4,4,6-trimethyl-1,2,3,4-tetrahydro-quinolin-2-yl)-phenyl]-benzensulfonamide LC/MS m/e obsd. (ESI$^+$) [(M+H)$^+$] 407.3.

Example 52

3-Fluoro-N-[2-(4,4,6-trimethyl-1,2,3,4-tetrahydro-quinolin-2-yl)-phenyl]-benzenesulfonamide

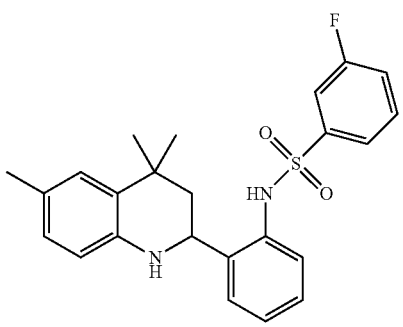 [SMILES: Cc1ccc2c(c1)C(C)(C)CC(c1ccccc1NS(=O)(=O)c1cccc(F)c1)N2]

To a solution of 2-(4,4,6-trimethyl-1,2,3,4-tetrahydro-quinolin-2-yl)aniline (150 mg, 0.56 mmol) and pyridine (0.5 mL) in anhydrous dichloromethane (2 mL) was added 3-fluorobenzene-1-sulfonyl chloride (70.1 mg, 0.36 mmol) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, and then concentrated. The residue was purified by HPLC to give 3-fluoro-N-[2-(4,4,6-trimethyl-1,2 3,4-tetrahydro-quinolin-2-yl)-phenyl]-benzenesulfonamide LC/MS m/e obsd. (ESI$^+$) [(M+H)$^+$] 425.3.

Example 53

N-[2-(4,4,6-Trimethyl-1,2,3,4-tetrahydro-quinolin-2-yl)-phenyl]-methanesulfonamide

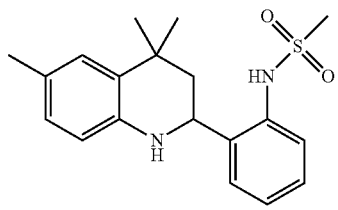 [SMILES: Cc1ccc2c(c1)C(C)(C)CC(c1ccccc1NS(C)(=O)=O)N2]

To a solution of 2-(4,4,6-trimethyl-1,2,3,4-tetrahydro-quinolin-2-yl)aniline (150 mg, 0.56 mmol) and pyridine (0.5 mL) in anhydrous dichloromethane (2 mL) was added methanesulfonyl chloride (44 µL) at ice-bath under nitrogen. After addition, the resulting mixture was stirred at room temperature for 3 h. The reaction mixture was diluted with water, and extracted with ethyl acetate. The combined organic layer was dried over anhydrous Sodium sulfate, and then concentrated. The residue was purified by HPLC to give N-[2-(4,4,6-trimethyl-1,2,3,4-tetrahydro-quinolin-2-yl)-phenyl]methanesulfonamide LC/MS m/e obsd. (ESI$^+$) [(M+H)$^+$] 345.2.

Example 54

Pyridine-3-sulfonic acid [2-(6-cyano-4,4-dimethyl-1,2,3,4-tetrahydro-quinolin-2-yl)-phenyl]-amide

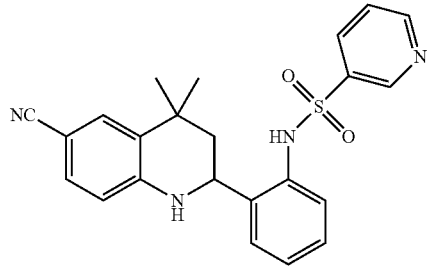 [SMILES: CC1(C)CC(c2ccccc2NS(=O)(=O)c2cccnc2)Nc2ccc(C#N)cc21]

To a solution of 2-(2-aminophenyl)-4,4-dimethyl-1,2,3,4-tetrahydroquinoline-6-carbonitrile (500 mg, 1.8 mmol) in pyridine (3 mL) was added pyridine-3-sulfonyl chloride (385 mg) at ice-bath under nitrogen. After addition, the resulting mixture was stirred at room temperature for 3 h. The reaction mixture was diluted with water, and extracted with ethyl acetate. The combined organic layer was dried over anhydrous Sodium sulfate, and then concentrated. The residue was purified by HPLC to give pyridine-3-sulfonic acid [2-(6-cyano-4,4-dimethyl-1,2,3,4-tetrahydro-quinolin-2-yl)-phenyl]-amide LC/MS m/e obsd. (ESI$^+$) [(M+H)$^+$] 419.3.

Example 55

Pyridine-3-sulfonic acid [2-(4,4-dimethyl-6-trifluoromethyl-1,2,3,4-tetrahydro-quinolin-2-yl)-phenyl]-amide

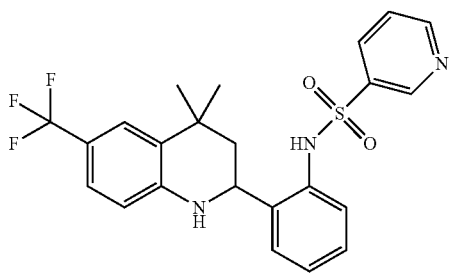 [SMILES: CC1(C)CC(c2ccccc2NS(=O)(=O)c2cccnc2)Nc2ccc(C(F)(F)F)cc21]

To a solution of 2-(4,4-dimethyl-6-(trifluoromethyl)-1,2,3,4-tetrahydroquinolin-2-yl)aniline (150 mg, 0.47 mmol) in pyridine (2 mL) was added pyridine-3-sulfonyl chloride (100 mg) at ice-bath under nitrogen. After addition, the resulting mixture was stirred at room temperature for 3 h. The reaction mixture was diluted with water, and extracted with ethyl acetate. The combined organic layer was dried over anhydrous sodium sulfate, and then concentrated. The residue was purified by HPLC to give pyridine-3-sulfonic acid [2-(4,4-dimethyl-6-trifluoromethyl-1,2,3,4-tetrahydro-quinolin-2-yl)-phenyl]-amide LC/MS m/e obsd. (ESI$^+$) [(M+H)$^+$] 462.3.

Example 56

Ethanesulfonic acid [3-(4,4-dimethyl-6-trifluoromethyl-1,2,3,4-tetrahydro-quinolin-2-yl)-phenyl]-amide

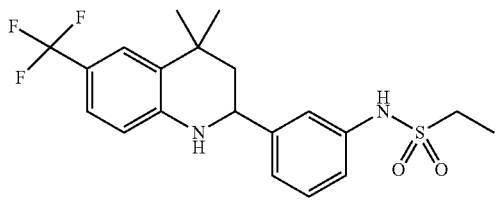 [SMILES: CCS(=O)(=O)Nc1cccc(C2CC(C)(C)c3cc(C(F)(F)F)ccc3N2)c1]

A mixture of 4-trifluoromethyl-phenylamine (10.0 g, 62.06 mmol) and 3-Nitro-benzaldehyde (9.3 g, 62.06 mmol) in toluene was heated to reflux for 5 h with a Dean-stark trap. After evaporation of the toluene, the reaction mixture was heated for another 1 h at this temperature to afford 18.3 g of [1-(3-nitro-phenyl)-meth-(E)-ylidene]-(4-trifluoromethyl-phenyl)-amine. The mixture was used in next step without further purification.

A mixture of [1-(3-nitro-phenyl)-meth-(E)-ylidene]-(4-trifluoromethyl-phenyl)-amine (18.2 g of crude, 62.1 mmol), isobutene (52 mL, 620.6 mmol) and boron trifluoride etherate (1.6 mL, 12.4 mmol) in acetonitrile in a hydrogenated kettle was stirred for two days at room temperature. The solution was evaporated in vacuo and the residue was crystallized by treating with ethyl acetate to give 5.9 g of 4,4-Dimethyl-2-(3-nitro-phenyl)-6-trifluoromethyl-1,2,3,4-tetrahydro-quinoline (yield: 27.1%).

A mixture of 4,4-dimethyl-2-(3-nitro-phenyl)-6-trifluoromethyl-1,2,3,4-tetrahydro-quinoline (2.99 g, 8.53 mmol) and iron powder (11.95 g, 0.21 mol) in ethanol/water/concentrated hydrogen chloride (24 mL/6 mL/0.08 mL) was kept at reflux for 2 h. The mixture was filtered and the mother liquor was concentrated in vacuo to give 2.6 g of 3-(4,4-dimethyl-6-trifluoromethyl-1,2,3,4-tetrahydro-quinolin-2-yl)-phenylamine as off-yellow solid (2.6 g, yield: 95.6%).

To a stirred solution of 3-(4,4-dimethyl-6-trifluoromethyl-1,2,3,4-tetrahydro-quinolin-2-yl)-phenylamine (150 mg, 0.47 mmol) in pyridine (74 mg, 0.94 mmol) and dichloromethane (2 mL) at 0° C. was added dropwise a solution of ethanesulfonyl chloride (90 mg, 0.70 mol) in dichloromethane (1 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford ethanesulfonic acid [3-(4,4-dimethyl-6-trifluoromethyl-1,2,3,4-tetrahydro-quinolin-2-yl)-phenyl]-amide (143 mg, 74.1%) as a white solid. MS (ESI+APCI) M+1=413.1.

Example 57

N-[3-(4,4-Dimethyl-6-trifluoromethyl-1,2,3,4-tetrahydro-quinolin-2-yl)-phenyl]-benzenesulfonamide

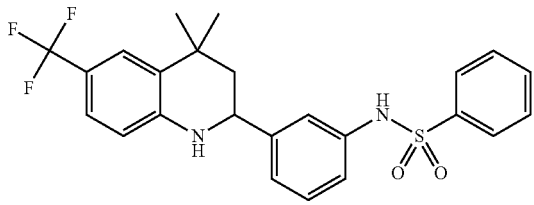 [SMILES: CC1(C)CC(c2cccc(NS(=O)(=O)c3ccccc3)c2)Nc2ccc(C(F)(F)F)cc21]

To a stirred solution of 3-(4,4-dimethyl-6-trifluoromethyl-1,2,3,4-tetrahydro-quinolin-2-yl)-phenylamine (100 mg, 0.31 mmol) in pyridine (49 mg, 0.62 mmol) and dichloromethane (1.5 mL) at 0° C. was added dropwise a solution of benzenesulfonyl chloride (66 mg, 0.37 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-benzenesulfonamide (113 mg, 79.3%) as a white solid. MS (ESI+APCI) M+1=461.1.

Example 58

N-[3-(4,4-Dimethyl-6-trifluoromethyl-1,2,3,4-tetrahydro-quinolin-2-yl)-phenyl]-4-fluoro-benzenesulfonamide

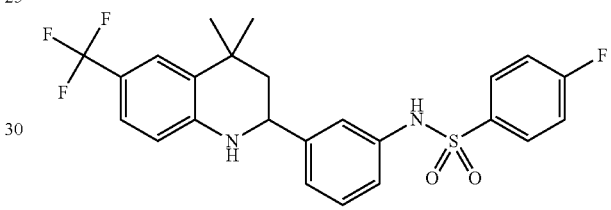

To a stirred solution of 3-(4,4-dimethyl-6-trifluoromethyl-1,2,3,4-tetrahydro-quinolin-2-yl)-phenylamine (100 mg, 0.31 mmol) in pyridine (49 mg, 0.62 mmol) and dichloromethane (1.5 mL) at 0° C. was added dropwise a solution of 4-fluoro-benzenesulfonyl chloride (73 mg, 0.37 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-4-fluoro-benzenesulfonamide (121 mg, 81.3%) as a white solid. MS (ESI+APCI) M+1=479.1.

Example 59

N-[3-(4,4-Dimethyl-6-trifluoromethyl-1,2,3,4-tetrahydro-quinolin-2-yl)-phenyl]-methanesulfonamide

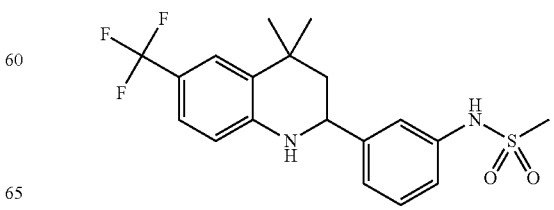

To a stirred solution of 3-(4,4-dimethyl-6-trifluoromethyl-1,2,3,4-tetrahydro-quinolin-2-yl)-phenylamine (150 mg, 0.49 mmol) in pyridine (74 mg, 0.94 mmol) and dichloromethane (1.5 mL) at 0° C. was added dropwise a solution of methanesulfonyl chloride (80 mg, 0.70 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-methanesulfonamide (120 mg, 64.5%) as a white solid. MS (ESI+APCI) M+1=399.1.

Example 60

N-[3-(4,4-Dimethyl-6-trifluoromethyl-1,2,3,4-tetrahydro-quinolin-2-yl)-phenyl]-2-fluoro-benzenesulfonamide

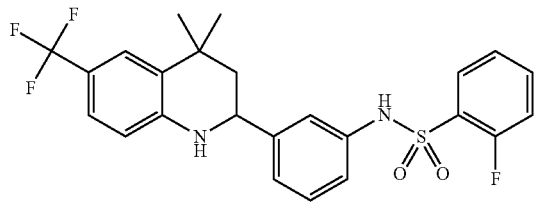 [SMILES: CC1(C)CC(c2cccc(NS(=O)(=O)c3ccccc3F)c2)Nc2ccc(C(F)(F)F)cc21]

To a stirred solution of 3-(4,4-dimethyl-6-trifluoromethyl-1,2,3,4-tetrahydro-quinolin-2-yl)-phenylamine (100 mg, 0.31 mmol) in pyridine (49 mg, 0.62 mmol) and dichloromethane (1.5 mL) at 0° C. was added dropwise a solution of 2-fluoro-benzenesulfonyl chloride (73 mg, 0.37 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-2-fluoro-benzenesulfonamide (97 mg, 65.1%) as a white solid. MS (ESI+APCI) M+1=479.1.

Example 61

N-[3-(4,4-Dimethyl-6-trifluoromethyl-1,2,3,4-tetrahydro-quinolin-2-yl)-phenyl]-3-fluoro-benzenesulfonamide

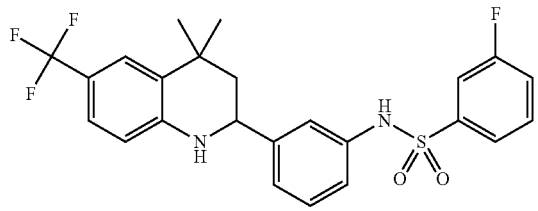 [SMILES: CC1(C)CC(c2cccc(NS(=O)(=O)c3cccc(F)c3)c2)Nc2ccc(C(F)(F)F)cc21]

To a stirred solution of 3-(4,4-dimethyl-6-trifluoromethyl-1,2,3,4-tetrahydro-quinolin-2-yl)-phenylamine (100 mg, 0.31 mmol) in pyridine (49 mg, 0.62 mmol) and dichloromethane (1.5 mL) at 0° C. was added dropwise a solution of 3-fluoro-benzenesulfonyl chloride (73 mg, 0.37 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-3-fluoro-benzenesulfonamide (141 mg, 94.6%) as a white solid. MS (ESI+APCI) M+1=479.1.

Example 62

Propane-2-sulfonic acid [3-(4,4-dimethyl-6-trifluoromethyl-1,2,3,4-tetrahydro-quinolin-2-yl)-phenyl]-amide

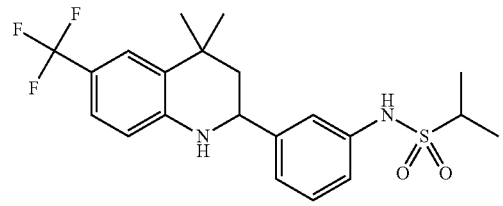 [SMILES: CC(C)S(=O)(=O)Nc1cccc(C2CC(C)(C)c3cc(C(F)(F)F)ccc3N2)c1]

To a stirred solution of 3-(4,4-dimethyl-6-trifluoromethyl-1,2,3,4-tetrahydro-quinolin-2-yl)-phenylamine (150 mg, 0.47 mmol) in pyridine (0.23 mL, 2.81 mmol) and dichloromethane (1.5 mL) at 0° C. was added dropwise a solution of propane-2-sulfonyl chloride (200 mg, 1.40 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford propane-2-sulfonic acid [3-(4,4-dimethyl-6-trifluoromethyl-1,2,3,4-tetrahydro-quinolin-2-yl)-phenyl]-amide (155 mg, 77.8%) as a white solid. MS (ESI+APCI) M+1=427.2.

Example 63

N-[3-(4,4-Dimethyl-6-trifluoromethyl-1,2,3,4-tetrahydro-quinolin-2-yl)-phenyl]-4-methyl-benzenesulfonamide

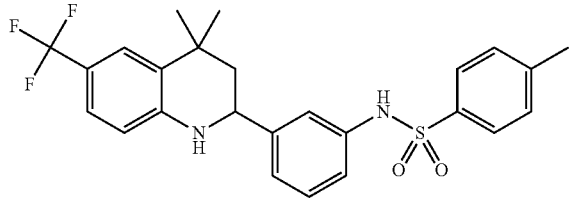 [SMILES: Cc1ccc(S(=O)(=O)Nc2cccc(C3CC(C)(C)c4cc(C(F)(F)F)ccc4N3)c2)cc1]

To a stirred solution of 3-(4,4-dimethyl-6-trifluoromethyl-1,2,3,4-tetrahydro-quinolin-2-yl)-phenylamine (100 mg, 0.31 mmol) in pyridine (49 mg, 0.62 mmol) and dichloromethane (1.5 mL) at 0° C. was added dropwise a solution of 4-Methyl-benzenesulfonyl chloride (71 mg, 0.37 mmol) in dichloromethane (0.5 mL). The mixture was stirred at room temperature overnight. The mixture was quenched with water (5 mL) and extracted with dichloromethane (5 mL×2). The combined organic layers were dried over anhydrous sodium sulfate and evaporated. The residue was purified by column chromatography on silica gel to afford N-[3-(4,4-dimethyl-6-trifluoromethyl-1,2,3,4-tetrahydro-quinolin-2-yl)-phenyl]-4-methyl-benzenesulfonamide (122 mg, 77.2%) as a white solid. MS (ESI+APCI) M+1=475.2.

Example 64

Pyridine-3-sulfonic acid [3-(4,4-dimethyl-6-trifluoromethyl-1,2,3,4-tetrahydro-quinolin-2-yl)-phenyl]-amide

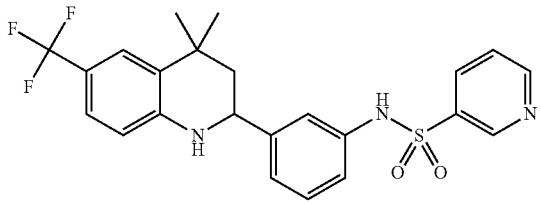 [SMILES: CC1(C)CC(c2cccc(NS(=O)(=O)c3cccnc3)c2)Nc2ccc(C(F)(F)F)cc21]

To a stirred solution of 3-(4,4-dimethyl-6-trifluoromethyl-1,2,3,4-tetrahydro-quinolin-2-yl)-phenylamine (150 mg, 0.47 mmol) in pyridine (0.74 mg, 0.94 mmol) and dichloromethane (3 mL) at 0° C. was added dropwise a solution of pyridine-3-sulfonyl chloride (100 mg, 0.56 mmol) in dichloromethane (1 mL). The mixture was stirred at room temperature overnight. Thin layer chromatography and LC-MS indicated that 3-(4,4,6-trimethyl-1,2,3,4-tetrahydro-quinolin-2-yl)-phenylamine was consumed completely. The mixture was quenched with water (5 mL) and extracted with dichloromethane (5 mL×2). The combined organic layers were dried over anhydrous sodium sulfate and evaporated. The residue was purified by column chromatography on silica gel to afford pyridine-3-sulfonic acid [3-(4,4-dimethyl-6-trifluoromethyl-1,2,3,4-tetrahydro-quinolin-2-yl)-phenyl]-amide (170 mg, 78.7%) as a white solid. MS (ESI+APCI) M+1=442.3.

Example 65

4-Fluoro-N-[3-(4,4,6-trimethyl-1,2,3,4-tetrahydro-quinolin-2-yl)-phenyl]-benzenesulfonamide

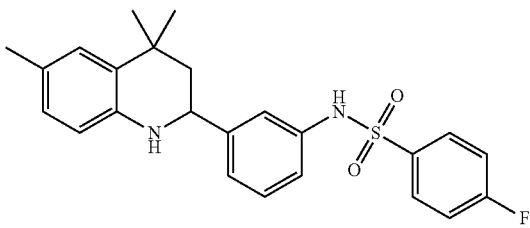 [SMILES: Cc1ccc2c(c1)C(C)(C)CC(c1cccc(NS(=O)(=O)c3ccc(F)cc3)c1)N2]

To a stirred solution of p-tolylamine (21.43 g, 0.2 mol) in ethanol (300 mL) was added 3-Nitro-benzaldehyde (30.22 g, 0.2 mol). The mixture was stirred overnight at room temperature. After filtration, the yellow solid was dried under infrared lamp, and the filtrate was concentrated, treated with ethanol again. The precipitated solid was filtered to afford 44.5 g of [1-(3-nitro-phenyl)-meth-(E)-ylidene]-p-tolyl-amine (Yield: 93%).

A 2000 mL of autoclave was charged with [1-(3-nitro-phenyl)-meth-(E)-ylidene]-p-tolyl-amine (44.5 g, 0.185 mmol), acetonitrile (500 mL), boron trifluoride etherate (30 mL). The mixture was cooled with liquid nitrogen, and then isobutene was added quickly. The resultant mixture was stirred at room temperature for 60 h. The reaction mixture was washed with brine, water, dried over magnesium sulfate, concentrated. The residue was washed with ethyl acetate and the desired 4,4,6-trimethyl-2-(3-nitro-phenyl)-1,2,3,4-tetrahydro-quinoline was obtained by filtration (53 g).

To a stirred solution of 4,4,6-Trimethyl-2-(3-nitro-phenyl)-1,2,3,4-tetrahydro-quinoline (10 g) in Ethanol/water (150 mL/30 mL) was added concentrated hydrochloric acid (2 mL) and Iron Powder (20 g, 356 mmol). The resultant mixture was heated to reflux for 2 h. Iron Powder was filtered, and washed with ethanol. The combined filtrate was concentrated, and diluted with water. The mixture was extracted with ethyl acetate (250 mL×3). The combined organic layers were washed with saturated brine, and the brine was extracted with ethyl acetate. The organic layers were dried over anhydrous sodium sulfate, concentrated. The residue was treated with ether and hexane to afford 4.5 g of 3-(4,4,6-trimethyl-1,2,3,4-tetrahydro-quinolin-2-yl)-phenylamine as brown solid (Yield: 50%).

To a stirred mixture of 3-(4,4,6-trimethyl-1,2,3,4-tetrahydro-quinolin-2-yl)-phenylamine (150 mg, 0.56 mmol) and pyridine (90 mg, 1.14 mmol) in dichloromethane (6 mL) was added 4-fluoro-benzenesulfonyl chloride (120 mg, 0.62 mmol) under nitrogen. The resultant mixture was stirred overnight. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether: ethyl acetate=10:1) to afford 100 mg of 4-fluoro-N-[3-(4,4,6-trimethyl-1,2,3,4-tetrahydro-quinolin-2-yl)-phenyl]-benzenesulfonamide as yellow solid (Yield: 42%). MS (ESI+APCI) M+1=425.2.

Example 66

2-Fluoro-N-[3-(4,4,6-trimethyl-1,2,3,4-tetrahydro-quinolin-2-yl)-phenyl]-benzenesulfonamide

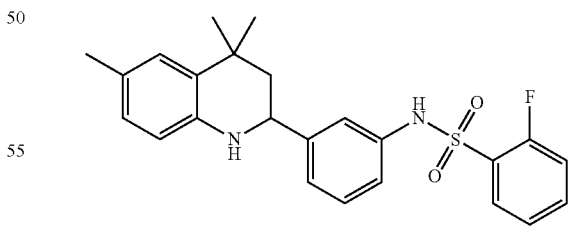

To a stirred mixture of 3-(4,4,6-trimethyl-1,2,3,4-tetrahydro-quinolin-2-yl)-phenylamine (135 mg, 0.5 mmol) in dichloromethane (3 mL) was added pyridine (60 mg, 0.75 mmol) in dichloromethane (2 mL) and 2-fluoro-benzenesulfonyl chloride (108 mg, 0.56 mmol) under nitrogen. The resultant mixture was stirred for 4 h. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether:ethyl acetate=15:1) to afford 100 mg of 2-fluoro-N-[3-(4,4,6-trimethyl-1,2,3,4-tetrahydro-quinolin-2-yl)-phenyl]-benzenesulfonamide yellow solid (Yield: 47%). MS (ESI+APCI) M+1=425.2.

Example 67

3-Fluoro-N-[3-(4,4,6-trimethyl-1,2,3,4-tetrahydro-quinolin-2-yl)-phenyl]-benzenesulfonamide

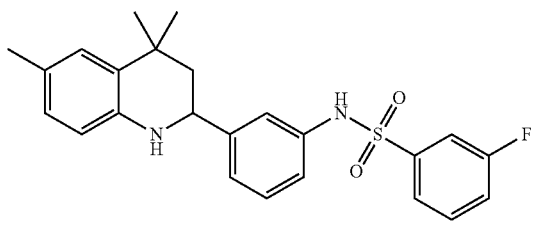 [SMILES: Cc1ccc2c(c1)C(C)(C)CC(c1cccc(NS(=O)(=O)c3cccc(F)c3)c1)N2]

To a stirred mixture of 3-(4,4,6-trimethyl-1,2,3,4-tetrahydro-quinolin-2-yl)-phenylamine (135 mg, 0.5 mmol) in dichloromethane (3 mL) was added pyridine (60 mg, 0.75 mmol) in dichloromethane (2 mL) and 3-fluoro-benzenesulfonyl chloride (108 mg, 0.56 mmol) under nitrogen. The resultant mixture was stirred for 4 h. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether: Ethyl acetate=12:1) to afford 80 mg of 3-fluoro-N-[3-(4,4,6-trimethyl-1,2,3,4-tetrahydro-quinolin-2-yl)-phenyl]-benzenesulfonamide as yellow solid (Yield: 38%). MS (ESI+APCI) M+1=425.2.

Example 68

N-[3-(4,4,6-Trimethyl-1,2,3,4-tetrahydro-quinolin-2-yl)-phenyl]-benzenesulfonamide

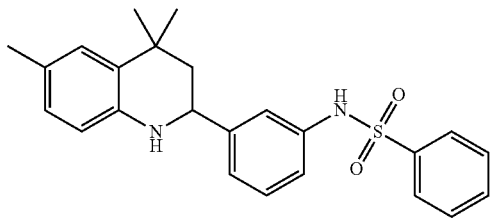 [SMILES: Cc1ccc2c(c1)C(C)(C)CC(c1cccc(NS(=O)(=O)c3ccccc3)c1)N2]

To a stirred mixture of 3-(4,4,6-trimethyl-1,2,3,4-tetrahydro-quinolin-2-yl)-phenylamine (135 mg, 0.5 mmol) in dichloromethane (3 mL) was added pyridine (60 mg, 0.75 mmol) in dichloromethane (2 mL) and benzenesulfonylchloride (108 mg, 0.56 mmol) under nitrogen. The resultant mixture was stirred for 20 h. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether:ethyl acetate=15:1) to afford 120 mg of N-[3-(4,4,6-trimethyl-1,2,3,4-tetrahydro-quinolin-2-yl)-phenyl]-benzenesulfonamide as yellow solid (Yield: 59%). MS (ESI+APCI) M+1=407.1.

Example 69

4-Methyl-N-[3-(4,4,6-trimethyl-1,2,3,4-tetrahydro-quinolin-2-yl)-phenyl]-benzenesulfonamide

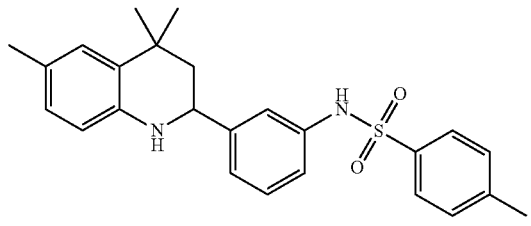

To a stirred mixture of 3-(4,4,6-trimethyl-1,2,3,4-tetrahydro-quinolin-2-yl)-phenylamine (135 mg, 0.5 mmol) in dichloromethane (3 mL) was added pyridine (60 mg, 0.75 mmol) in dichloromethane (2 mL) and 4-methyl-benzenesulfonyl chloride (108 mg, 0.56 mmol) under nitrogen. The resultant mixture was stirred for 16 h. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether:ethyl acetate=15:1) to afford 67 mg of 4-methyl-N-[3-(4,4,6-trimethyl-1,2,3,4-tetrahydro-quinolin-2-yl)-phenyl]-benzenesulfonamide as yellow solid (Yield: 32%). MS (ESI+APCI) M+1=421.2.

Example 70

N-[3-(4,4,6-Trimethyl-1,2,3,4-tetrahydro-quinolin-2-yl)-phenyl]-methanesulfonamide

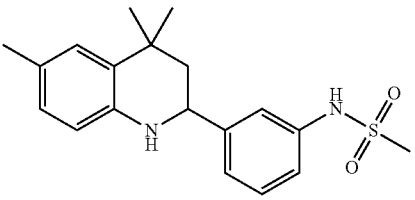

To a stirred mixture of 3-(4,4,6-trimethyl-1,2,3,4-tetrahydro-quinolin-2-yl)-phenylamine (150 mg, 0.56 mmol) in dichloromethane (3 mL) was added pyridine (79 mg, 1.01 mmol) in dichloromethane (2 mL) and methanesulfonyl chloride (96 mg, 0.84 mmol) under nitrogen. The resultant mixture was stirred for 16 h. The reaction mixture was diluted with dichloromethane, washed with water (twice), saturated brine, and dried over magnesium sulfate. Magnesium sulfate was removed by filtration, and after evaporation, the residue was purified on chromatography column (silica gel, petroleum ether: ethyl acetate=10:1) to afford 63 mg of N-[3-(4,4, 6-trimethyl-1,2,3,4-tetrahydro-quinolin-2-yl)-phenyl]-methanesulfonamide as yellow solid (Yield: 33%). MS (ESI+ APCI) M+1=345.2.

Example 71

Ethanesulfonic acid [3-(4,4,6-trimethyl-1,2,3,4-tetrahydro-quinolin-2-yl)-phenyl]-amide

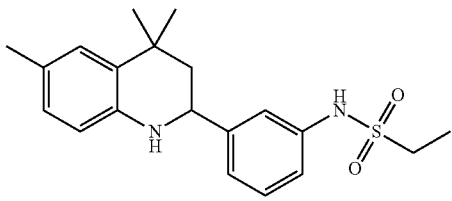 [SMILES: CCS(=O)(=O)Nc1cccc(C2CC(C)(C)c3cc(C)ccc3N2)c1]

To a stirred mixture of 3-(4,4,6-trimethyl-1,2,3,4-tetrahydro-quinolin-2-yl)-phenylamine (150 mg, 0.56 mmol) in dichloromethane (3 mL) was added pyridine (79 mg, 1.01 mmol) in dichloromethane (2 mL) and ethanesulfonyl chloride (108 mg, 0.84 mmol) under nitrogen. The resultant mixture was stirred for 18 h. The reaction mixture was diluted with dichloromethane, washed with water (twice), saturated brine, and dried over Magnesium sulfate. Magnesium sulfate was removed by filtration, and after evaporation, the residue was purified on chromatography column (silica gel, petroleum ether: ethyl acetate=10:1) to afford 75 mg of ethanesulfonic acid [3-(4,4,6-trimethyl-1,2,3,4-tetrahydro-quinolin-2-yl)-phenyl]-amide yellow solid (Yield: 37%). MS (ESI+APCI) M+1=359.2.

Example 72

Pyridine-3-sulfonic acid [3-(4,4,6-trimethyl-1,2,3,4-tetrahydro-quinolin-2-yl)-phenyl]-amide

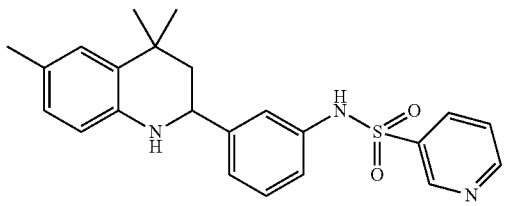 [SMILES: Cc1ccc2c(c1)C(C)(C)CC(c1cccc(NS(=O)(=O)c3cccnc3)c1)N2]

Pyridine-3-sulfonyl chloride (96 mg, 0.54 mmol) was added dropwise a mixture of 3-(4,4,6-trimethyl-1,2,3,4-tetrahydro-quinolin-2-yl)-phenylamine (120 mg, 0.45 mmol) and pyridine (60 mg, 0.76 mmol) in dichloromethane (5 mL). The resultant mixture was allowed to stir overnight. The reaction mixture was washed by water, dried over magnesium sulfate. The mixture was filtered and concentrated to provide the crude product. It was purified by column chromatography (silica gel, petroleum ether:ethyl acetate=4:1) to afford pyridine-3-sulfonic acid [3-(4,4,6-trimethyl-1,2,3,4-tetrahydro-quinolin-2-yl)-phenyl]-amide as off-white solid (25 mg, yield: 13.7%). MS (ESI+APCI) M+1=408.2.

Example 73

N-[3-(6-Cyano-4,4-dimethyl-1,2,3,4-tetrahydro-quinolin-2-yl)-phenyl]-2-fluoro-benzenesulfonamide

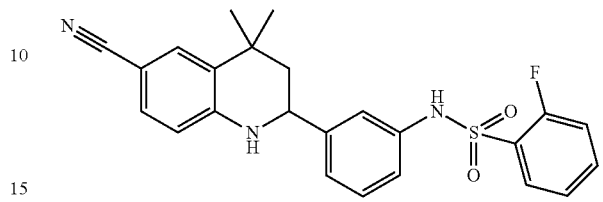

A mixture of 4-amino-benzonitrile (23.6 g, 0.2 mmol) in toluene (200 mL) was treated with a solution of 3-nitro-benzaldehyde (30.2 g, 0.2 mmol) in toluene (50 mL). The resultant mixture was allowed to reflux for 6 h. Toluene was removed under vacuum. The residue was purified by recrystallization from ethanol to afford 4-{[1-(3-nitro-phenyl)-meth-(E)-ylidene]-amino}-benzonitrile as yellow solid (50 g, yield %: 95.0%).

To a small reactor, isobutene (100 mL, 1.19 mol) was added to a mixture of boron trifluoride etherate (12 mL, 0.96 mmol) and 4-{[1-(3-nitro-phenyl)-meth-(E)-ylidene]-amino}-benzonitrile (30 g, 0.12 mol) in dry acetonitrile (300 mL), sealed. The resultant mixture was allowed to stir at 30° C. for 10 h. The reaction mixture was washed by brine and dried over anhydrous sodium sulfate. It was filtered and concentrated to provide the crude product (30 g). The residue was purified by column chromatography (silica gel, petroleum ether:ethyl acetate=5:1) to afford 4,4-dimethyl-2-(3-nitro-phenyl)-1,2,3,4-tetrahydro-quinoline-6-carbonitrile as yellow solid (10.2 g, yield: 27.8%).

To a round bottom flask, iron powder (9.13 g, 162.7 mmol) and concentrated hydrochloric acid (0.16 mL) were added to a mixture of 4,4-dimethyl-2-(3-nitro-phenyl)-1,2,3,4-tetrahydro-quinoline-6-carbonitrile (5 g, 16.3 mmol) in ethanol (50 mL) and water (12 mL). The resultant mixture was allowed to stir at reflux for 1.5 h. The mixture was filtrated and the filtered cake was washed by ethanol several times. The ethanol was removed under vacuum. The residue was dissolved in ethyl acetate (100 mL) and water (50 mL), separated the organic layer. The organic layer was washed by brine twice and dried over anhydrous sodium sulfate. Filtered and concentrated to provide 2-(3-amino-phenyl)-4,4-dimethyl-1,2,3,4-tetrahydro-quinoline-6-carbonitrile as yellow solid (4.2 g, yield: 85%). MS (ESI+APCI) 278.2.

To a round bottom flask, 2-fluoro-benzenesulfonyl chloride (116 mg, 0.59 mmol) was added dropwise a mixture of 2-(3-amino-phenyl)-4,4-dimethyl-1,2,3,4-tetrahydro-quinoline-6-carbonitrile (150 mg, 0.54 mmol) and pyridine (65 mg, 0.81 mmol) in dichloromethane (5 mL). The resultant mixture was allowed to stir overnight. The reaction mixture was washed by water, dried over magnesium sulfate. It was filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-2-fluoro-benzenesulfonamide as off-white solid (100 mg, yield: 42.4%). MS (ESI+APCI) M+1=436.1.

Example 74

N-[3-(6-Cyano-4,4-dimethyl-1,2,3,4-tetrahydro-quinolin-2-yl)-phenyl]-3-fluoro-benzenesulfonamide

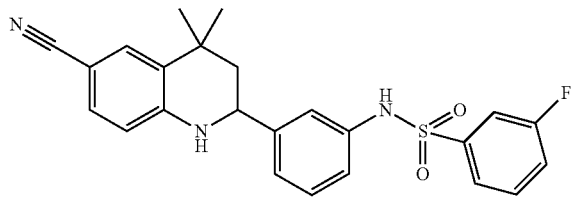 [SMILES: CC1(C)CC(c2cccc(NS(=O)(=O)c3cccc(F)c3)c2)Nc2ccc(C#N)cc21]

3-Fluoro-benzenesulfonyl chloride (116 mg, 0.59 mmol) was added dropwise to a mixture of 2-(3-amino-phenyl)-4,4-dimethyl-1,2,3,4-tetrahydro-quinoline-6-carbonitrile (150 mg, 0.54 mmol) and pyridine (65 mg, 0.81 mmol) in dichloromethane (5 mL). The resultant mixture was allowed to stir overnight. The reaction mixture was washed by water, dried over magnesium sulfate. It was filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-3-fluoro-benzenesulfonamide as off-white solid (102 mg, yield: 42.5%). MS (ESI+APCI) M+1=436.1.

Example 75

N-[3-(6-Cyano-4,4-dimethyl-1,2,3,4-tetrahydro-quinolin-2-yl)-phenyl]-4-fluoro-benzenesulfonamide

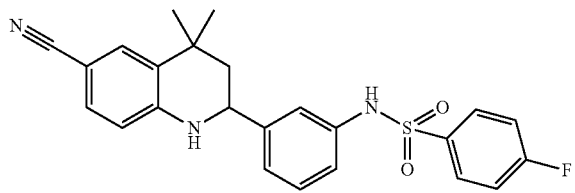 [SMILES: CC1(C)CC(c2cccc(NS(=O)(=O)c3ccc(F)cc3)c2)Nc2ccc(C#N)cc21]

3-Fluoro-benzenesulfonyl chloride (91 mg, 0.46 mmol) was added dropwise to a mixture of 2-(3-amino-phenyl)-4,4-dimethyl-1,2,3,4-tetrahydro-quinoline-6-carbonitrile (100 mg, 0.36 mmol) and pyridine (45 mg, 0.54 mmol) in dichloromethane (5 mL). The resultant mixture was allowed to stir overnight. The reaction mixture was washed by water, dried over magnesium sulfate. It was filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-4-fluoro-benzenesulfonamide as off-white solid (60 mg, Yield: 38.2%). MS (ESI+APCI) M+1=436.2.

Example 76

N-[3-(6-Cyano-4,4-dimethyl-1,2,3,4-tetrahydro-quinolin-2-yl)-phenyl]-benzenesulfonamide

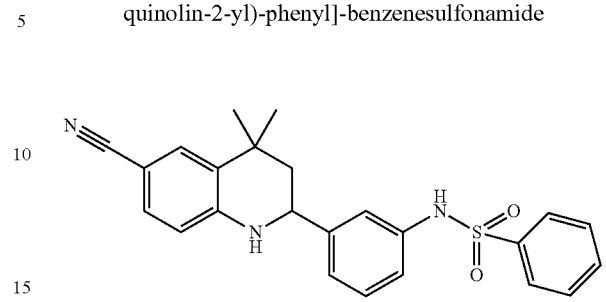

To a round bottom flask, benzenesulfonyl chloride (83 mg, 0.54 mmol) was added dropwise a mixture of 2-(3-amino-phenyl)-4,4-dimethyl-1,2,3,4-tetrahydro-quinoline-6-carbonitrile (100 mg, 0.36 mmol) and pyridine (45 mg, 0.54 mmol) in dichloromethane (5 mL). The resultant mixture was allowed to stir overnight. The reaction mixture was washed by water, dried over magnesium sulfate. Filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-benzenesulfonamide as off-white solid (70 mg, yield: 46.5%). MS (ESI+APCI) M+1=418.2.

Example 77

N-[3-(6-Cyano-4,4-dimethyl-1,2,3,4-tetrahydro-quinolin-2-yl)-phenyl]-methanesulfonamide

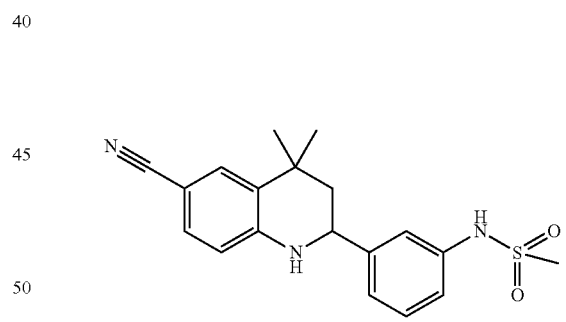

Methanesulfonyl chloride (93 mg, 0.81 mmol) was added dropwise to a mixture of 2-(3-amino-phenyl)-4,4-dimethyl-1,2,3,4-tetrahydro-quinoline-6-carbonitrile (150 mg, 0.54 mmol) and pyridine (77 mg, 0.97 mmol) in dichloromethane (5 mL). The resultant mixture was allowed to stir overnight. The reaction mixture was washed by water, dried over magnesium sulfate. It was filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-methanesulfonamide as off-white solid (100 mg, Yield: 52.1%). MS (ESI+APCI) M+1=356.2.

Example 78

Ethanesulfonic acid [3-(6-cyano-4,4-dimethyl-1,2,3,4-tetrahydro-quinolin-2-yl)-phenyl]-amide

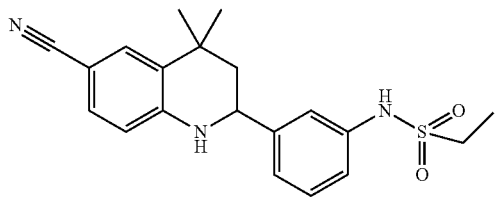 [SMILES: CCS(=O)(=O)Nc1cccc(C2CC(C)(C)c3cc(C#N)ccc3N2)c1]

Ethanesulfonyl chloride (104 mg, 0.81 mmol) was added dropwise to a mixture of 2-(3-amino-phenyl)-4,4-dimethyl-1,2,3,4-tetrahydro-quinoline-6-carbonitrile (150 mg, 0.54 mmol) and pyridine (77 mg, 0.97 mmol) in dichloromethane (5 mL). The resultant mixture was allowed to stir overnight. The reaction mixture was washed by water, dried over magnesium sulfate. It was filtered and concentrated to provide the crude product. It was purified by column chromatography (silica gel, petroleum ether:ethyl acetate=5:1) to afford ethanesulfonic acid [3-(6-cyano-4,4-dimethyl-1,2,3,4-tetrahydro-quinolin-2-yl)-phenyl]-amide as off-white solid (120 mg, yield: 60.0%). MS (ESI+APCI) M+1=370.2.

Example 79

Propane-2-sulfonic acid [3-(6-cyano-4,4-dimethyl-1,2,3,4-tetrahydro-quinolin-2-yl)-phenyl]-amide

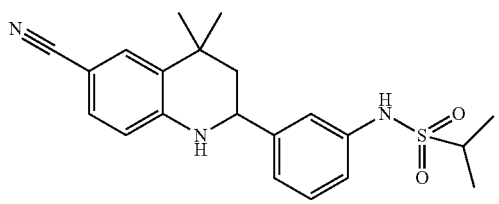 [SMILES: CC(C)S(=O)(=O)Nc1cccc(C2CC(C)(C)c3cc(C#N)ccc3N2)c1]

Propane-2-sulfonyl chloride (231 mg, 1.62 mmol) was added dropwise to a mixture of 2-(3-amino-phenyl)-4,4-dimethyl-1,2,3,4-tetrahydro-quinoline-6-carbonitrile (150 mg, 0.54 mmol) and pyridine (342 mg, 4.32 mmol) in dichloromethane (5 mL). The resultant mixture was allowed to stir for 7 days. The reaction mixture was washed by water, dried over magnesium sulfate. Filtered and concentrated to provide the crude product. It was purified by column chromatography (silica gel, petroleum ether:ethyl acetate=5:1) to afford propane-2-sulfonic acid [3-(6-cyano-4,4-dimethyl-1,2,3,4-tetrahydro-quinolin-2-yl)-phenyl]-amide as off-white solid (97 mg, yield: 46.8%). MS (ESI+APCI) M+1=384.2.

Example 80

N-[3-(6-Cyano-4,4-dimethyl-1,2,3,4-tetrahydro-quinolin-2-yl)-phenyl]-4-methyl-benzenesulfonamide

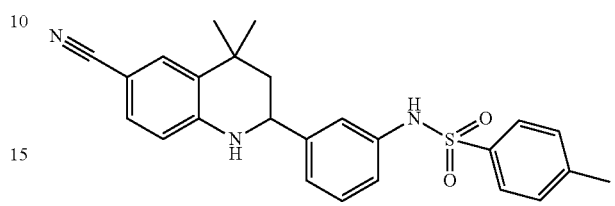

4-Methyl-benzenesulfonyl chloride (103 mg, 0.54 mmol) was added dropwise to a mixture of 2-(3-amino-phenyl)-4,4-dimethyl-1,2,3,4-tetrahydro-quinoline-6-carbonitrile (100 mg, 0.36 mmol) and pyridine (51 mg, 0.65 mmol) in dichloromethane (5 mL). The resultant mixture was allowed to stir overnight. The reaction mixture was washed by water, dried over magnesium sulfate. Filtered and concentrated to provide the crude product. It was purified by column chromatography (silica gel, petroleum ether:ethyl acetate=5:1) to afford N-[3-(6-cyano-4,4-dimethyl-1,2,3,4-tetrahydro-quinolin-2-yl)-phenyl]-4-methyl-benzenesulfonamide as off-white solid (60 mg, yield: 38.6%). MS (ESI+APCI) M+1=432.2.

Example 81

Pyridine-3-sulfonic acid [3-(6-cyano-4,4-dimethyl-1,2,3,4-tetrahydro-quinolin-2-yl)-phenyl]-amide

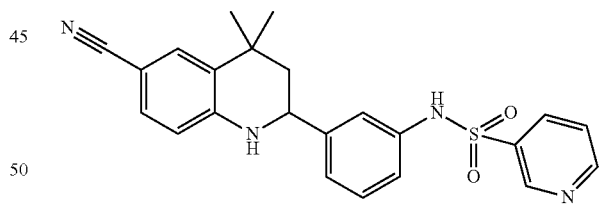

Pyridine-3-sulfonyl chloride (144 mg, 0.81 mmol) was added dropwise to a mixture of 2-(3-amino-phenyl)-4,4-dimethyl-1,2,3,4-tetrahydro-quinoline-6-carbonitrile (150 mg, 0.54 mmol) and pyridine (77 mg, 0.97 mmol) in dichloromethane (5 mL). The resultant mixture was allowed to stir overnight. The reaction mixture was washed by water, dried over magnesium sulfate. Filtered and concentrated to provide the crude product. It was purified by column chromatography (silica gel, petroleum ether:ethyl acetate=3:1) to afford pyridine-3-sulfonic acid [3-(6-cyano-4,4-dimethyl-1,2,3,4-tetrahydro-quinolin-2-yl)-phenyl]-amide as off-white solid (100 mg, yield: 44.2%). MS (ESI+APCI) M+1=419.1.

Example 82

N-[3-(6-Chloro-4,4-dimethyl-1,2,3,4-tetrahydro-quinolin-2-yl)-phenyl]-4-fluoro-benzenesulfonamide

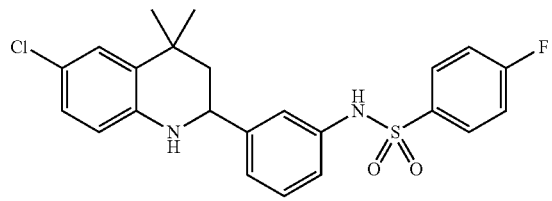 [SMILES: CC1(C)CC(c2cccc(NS(=O)(=O)c3ccc(F)cc3)c2)Nc2ccc(Cl)cc21]

To a mixture of 4-chloro-phenylamine (12.8 g 100 mmol) and 3-nitro-benzaldehyde (15.1 g, 100 mmol) was added 100 mL of toluene. The resulting solution was heated to reflux with a dean-stark trap for 3 h. The toluene was removed and the residue was collect to afford (4-chloro-phenyl)-[1-(3-nitro-phenyl)-meth-(E)-ylidene]-amine as yellow solid (26.5 g, yield: 95%). (4-Chloro-phenyl)-[1-(3-nitro-phenyl)-meth-(E)-ylidene]-amine (10.0 g, 36.5 mmol), isobutene (31 ml, 365.4 mmol, 10 g), boron trifluoride etherate (1.98 ml, 7.31 mmol) and acetonitrile (40 ml) were added into a autoclave and was stirred at room temperature for 72 h. Brine was added and the organic layer was separated, dried and concentrated to afford 6-chloro-4,4-dimethyl-2-(3-nitro-phenyl)-1,2,3,4-tetrahydro-quinoline as yellow solid (8.7 g, yield: 73%).

Iron powder (43.0 g, 762 mmol), ethanol/water (3:1, 720 ml) and 6-chloro-4,4-dimethyl-2-(3-nitro-phenyl)-1,2,3,4-tetrahydro-quinoline (24.1 g, 76 mmol) were heated to reflux for 2 h. iron powder was filtered and the solvent was removed to afford 3-(6-chloro-4,4-dimethyl-1,2,3,4-tetrahydro-quinolin-2-yl)-phenylamine as yellow solid (20.9 g, yield: 90%).

3-(6-Chloro-4,4-dimethyl-1,2,3,4-tetrahydro-quinolin-2-yl)-phenylamine (150 mg, 0.53 mmol) and 4-fluoro-benzenesulfonyl chloride (98 mg, 0.63 mmol) were dissolved in pyridine (5 ml). The mixture was stirred at room temperature overnight. The solvent was removed and the residue was purified on column chromatography using petroleum ether/ethyl acetate=5:1 as eluent to afford N-[3-(6-chloro-4,4-dimethyl-1,2,3,4-tetrahydro-quinolin-2-yl)-phenyl]-4-fluoro-benzenesulfonamide (135 mg, yield: 46%) as yellow solid. MS (ESI+APCI) M+1=445.1.

Example 83

N-[3-(6-Chloro-4,4-dimethyl-1,2,3,4-tetrahydro-quinolin-2-yl)-phenyl]-2-fluoro-benzenesulfonamide

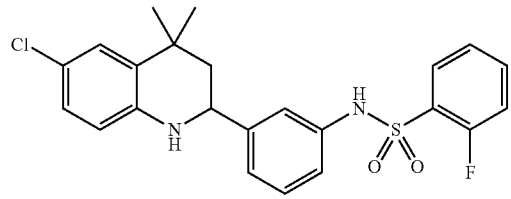 [SMILES: CC1(C)CC(c2cccc(NS(=O)(=O)c3ccccc3F)c2)Nc2ccc(Cl)cc21]

3-(6-Chloro-4,4-dimethyl-1,2,3,4-tetrahydro-quinolin-2-yl)-phenylamine (150 mg, 0.53 mmol) and the 2-fluoro-benzenesulfonyl chloride (92 mg, 0.63 mmol) was dissolved in pyridine (5 mL). The mixture was stirred at room temperature overnight. The solvent was removed and the residue was purified on column chromatography using petroleum ether/ethyl acetate=5:1 as eluent to afford N-[3-(6-chloro-4,4-dimethyl-1,2,3,4-tetrahydro-quinolin-2-yl)-phenyl]-2-fluoro-benzenesulfonamide (113 mg, yield: 44%) as yellow solid. MS (ESI+APCI) M+1=445.1.

Example 84

N-[3-(6-Chloro-4,4-dimethyl-1,2,3,4-tetrahydro-quinolin-2-yl)-phenyl]-4-methyl-benzenesulfonamide

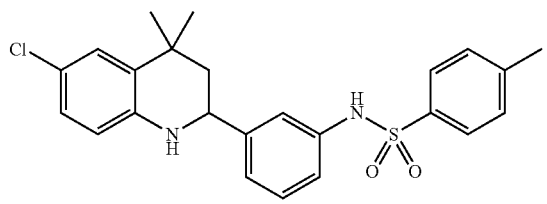 [SMILES: Cc1ccc(S(=O)(=O)Nc2cccc(C3CC(C)(C)c4cc(Cl)ccc4N3)c2)cc1]

3-(6-Chloro-4,4-dimethyl-1,2,3,4-tetrahydro-quinolin-2-yl)-phenylamine (150 mg, 0.53 mmol) and 4-methyl-benzenesulfonyl chloride (103 mg, 0.63 mmol) were dissolved in pyridine (5 ml). The mixture was stirred at room temperature overnight. The solvent was removed and the residue was purified on column chromatography using petroleum ether/Ethyl acetate=5:1 as eluent to afford N-[3-(6-chloro-4,4-dimethyl-1,2,3,4-tetrahydro-quinolin-2-yl)-phenyl]-4-methyl-benzenesulfonamide (133 mg, yield: 46%) as yellow solid. MS (ESI+APCI) M+1=441.1.

Example 85

N-[3-(6-Chloro-4,4-dimethyl-1,2,3,4-tetrahydro-quinolin-2-yl)-phenyl] benzenesulfonamide

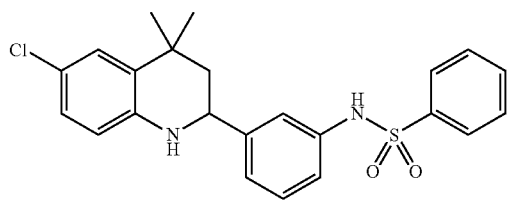 [SMILES: CC1(C)CC(c2cccc(NS(=O)(=O)c3ccccc3)c2)Nc2ccc(Cl)cc21]

3-(6-Chloro-4,4-dimethyl-1,2,3,4-tetrahydro-quinolin-2-yl)-phenylamine (150 mg, 0.53 mmol) and benzenesulfonyl chloride (92 mg, 0.63 mmol) were dissolved in pyridine (5 mL). The mixture was stirred at room temperature overnight. The solvent was removed and the residue was purified on column chromatography using petroleum ether/ethyl acetate=5:1 as eluent to afford N-[3-(6-chloro-4,4-dimethyl-1,2,3,4-tetrahydro-quinolin-2-yl)-phenyl]-benzenesulfonamide (110 mg, yield: 44%) as yellow solid. MS (ESI+APCI) M+1=427.1.

Example 86

N-[3-(6-Chloro-4,4-dimethyl-1,2,3,4-tetrahydro-quinolin-2-yl)-phenyl]-3-fluoro-benzenesulfonamide

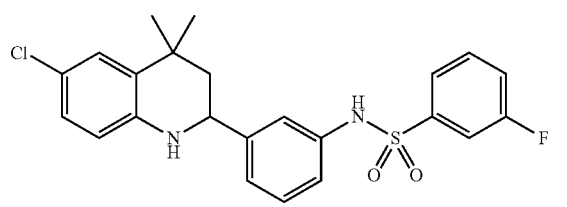 [SMILES: CC1(C)CC(c2cccc(NS(=O)(=O)c3cccc(F)c3)c2)Nc2ccc(Cl)cc21]

3-(6-Chloro-4,4-dimethyl-1,2,3,4-tetrahydro-quinolin-2-yl)-phenylamine (150 mg, 0.53 mmol) and 3-fluoro-benzenesulfonyl chloride (92 mg, 0.63 mmol) were dissolved in pyridine (5 ml). The mixture was stirred at room temperature overnight. The solvent was removed and the residue was purified on column chromatography using petroleum ether/ethyl acetate=5:1 as eluent to afford N-[3-(6-chloro-4,4-dimethyl-1,2,3,4-tetrahydro-quinolin-2-yl)-phenyl]-3-fluoro-benzenesulfonamide 122 mg (yield: 41%) as yellow solid. MS (ESI+APCI) M+1=445.1.

Example 87

N-[3-(6-Chloro-4,4-dimethyl-1,2,3,4-tetrahydro-quinolin-2-yl)-phenyl]-methanesulfonamide

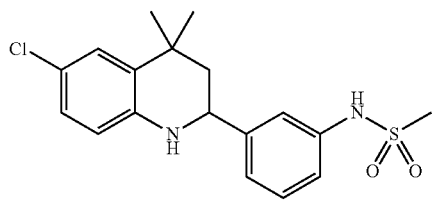 [SMILES: CC1(C)CC(c2cccc(NS(C)(=O)=O)c2)Nc2ccc(Cl)cc21]

3-(6-Chloro-4,4-dimethyl-1,2,3,4-tetrahydro-quinolin-2-yl)-phenylamine (150 mg, 0.53 mmol) and methanesulfonyl chloride (60 mg, 0.63 mmol) were dissolved in pyridine (5 ml). The mixture was stirred at room temperature overnight. The solvent was removed and the residue was purified on column chromatography using petroleum ether/ethyl acetate=5:1 as eluent to afford N-[3-(6-chloro-4,4-dimethyl-1,2,3,4-tetrahydro-quinolin-2-yl)-phenyl]-methanesulfonamide (149 mg, yield: 55%) as yellow solid. MS (ESI+APCI) M+1=445.

Example 88

3-(6-Chloro-4,4-dimethyl-1,2,3,4-tetrahydro-quinolin-2-yl)-N-methyl-benzenesulfonamide

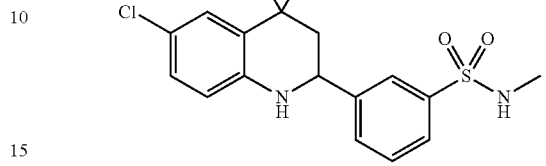

Sulphur dioxide was bubbled into a flask with acetic acid (10 mL) and cupric chloride (62 mg 0.63 mmol) until the green solution turned into blue. 3-(6-chloro-4,4-dimethyl-1,2,3,4-tetrahydro-quinolin-2-yl)-phenylamine (600 mg 2.09 mmol) was dissolved in a aceticacid (27 mL) and hydrochloric acid (3 mL) solution, and cooled to −10° C., sodium nitrite (213 mg, 3.09 mmol) in water (2 mL) solution was added and the mixture was stirred for 45 min. sulphur dioxide solution was added dropwise to the diazonium salt solution and stirred at −10° C. After the addition, the solution was warmed to room temperature and stirred for 24 h. The mixture was poured to 100 mL water and extracted with dichloromethane. The combined organic layers was washed with sodium bicarbonate and dried. Removal of the solvent afforded 3-(6-chloro-4,4-dimethyl-1,2,3,4-tetrahydro-quinolin-2-yl)-benzenesulfonyl chloride as yellow solid (crude 98 mg).

3-(6-Chloro-4,4-dimethyl-1,2,3,4-tetrahydro-quinolin-2-yl)-benzenesulfonyl chloride (234 mg, 0.63 mmol) was dissolved in dichloromethane (5 ml). Pyridine (5 ml) was added to the mixture. The resulting solution was cooled to 0° C., and methylamine hydrochloride (64 mg, 0.95 mmol) was added. The mixture was stirred at room temperature for 2 h. Solvent was removed and the residue was purified on Thin layer chromatography using petroleum ether/ethyl acetate=3:1 as eluent to afford 3-(6-chloro-4,4-dimethyl-1,2,3,4-tetrahydro-quinolin-2-yl)-N-methyl-benzenesulfonamide as white solid (100 mg, yield: 40%). MS (ESI+APCI) M+1=395.1.

Example 89

Ethanesulfonic acid [3-(6-chloro-4,4-dimethyl-1,2,3,4-tetrahydro-quinolin-2-yl)-phenyl]-amide

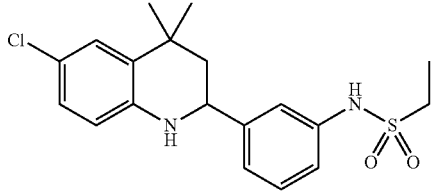 [SMILES: CCS(=O)(=O)Nc1cccc(C2CC(C)(C)c3cc(Cl)ccc3N2)c1]

3-(6-Chloro-4,4-dimethyl-1,2,3,4-tetrahydro-quinolin-2-yl)-phenylamine (150 mg, 0.53 mmol) and ethanesulfonyl chloride (67 mg, 0.63 mmol) were dissolved in pyridine (5 mL). The mixture was stirred at room temperature overnight. The solvent was removed and the residue was purified on column chromatography using petroleum ether/ethyl acetate=5:1 as eluent to afford ethanesulfonic acid [3-(6-chloro-4,4-dimethyl-1,2,3,4-tetrahydro-quinolin-2-yl)-phenyl]-amide (142 mg, yield: 54%) as yellow solid. MS (ESI+APCI) M+1=445.1.

Example 90

3-(6-Chloro-4,4-dimethyl-1,2,3,4-tetrahydro-quinolin-2-yl)-N-(4-fluoro-phenyl)-benzenesulfonamide

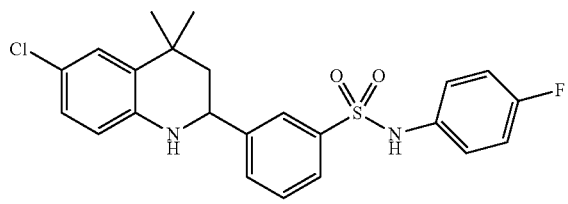 [SMILES: CC1(C)CC(c2cccc(S(=O)(=O)Nc3ccc(F)cc3)c2)Nc2ccc(Cl)cc21]

3-(6-Chloro-4,4-dimethyl-1,2,3,4-tetrahydro-quinolin-2-yl)-benzenesulfonyl chloride (204 mg 0.55 mmol) was dissolved in dichloromethane (5 mL). Pyridine (5 mL) was added to the mixture and cooled to 0° C. 4-fluoro-phenylamine (61 mg, 0.55 mmol) was added. The mixture was stirred at room temperature for 2 h. Solvent was removed and the residue was purified on thin layer chromatography using petroleum ether/ethyl acetate=3:1 as eluent to afford 3-(6-chloro-4,4-dimethyl-1,2,3,4-tetrahydro-quinolin-2-yl)-N-(4-fluoro-phenyl)-benzenesulfonamide as white solid (89 mg, 37% yield). MS (ESI+APCI) M+1=445.1.

Example 91

Pyridine-3-sulfonic acid [3-(6-chloro-4,4-dimethyl-1,2,3,4-tetrahydro-quinolin-2-yl)-phenyl]-amide

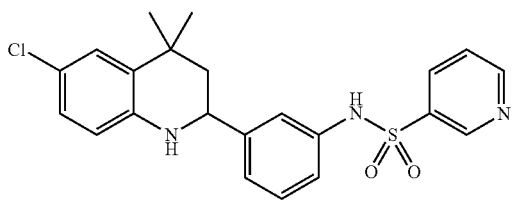 [SMILES: CC1(C)CC(c2cccc(NS(=O)(=O)c3cccnc3)c2)Nc2ccc(Cl)cc21]

3-(6-Chloro-4,4-dimethyl-1,2,3,4-tetrahydro-quinolin-2-yl)-phenylamine (150 mg, 0.53 mmol) and pyridine-3-sulfonyl chloride (102 mg, 0.63 mmol) were dissolved in pyridine (5 mL). The mixture was stirred at room temperature overnight. The solvent was removed and the residue was purified on column chromatography using petroleum ether/ethyl acetate=5:1 as eluent to afford pyridine-3-sulfonic acid [3-(6-chloro-4,4-dimethyl-1,2,3,4-tetrahydro-quinolin-2-yl)-phenyl]-amide (73 mg, yield: 39%) as yellow solid. MS (ESI+APCI) M+1=357.2.

Example 92

ADP Quest™ Assay for AMPK Activators

This method evaluates AMP-activated protein kinase (AMPK) activity through detecting the accumulation of ADP product using an ADP Quest kit and determining the $E_{30}$ values of the small molecular AMPK activators. ADP Quest kit (DiscoveRx, Fremont, Calif.) is stored at −20° C. before use. Before an experiment, thaw the kit (include assay buffer, ADP standard solution, reagent A and reagent B) and equilibrate to room temperature. Dispense the ADP Quest reagents into single-use aliquots and store at −20° C. The compound concentrations typically range from 0 µM to 100 µM by 2-fold dilution. AMP concentrations range from 0.98 µM to 1 mM as the reference control. In an assay, thaw and equilibrate the assay buffer, reagent A and reagent B to room temperature for 30 minutes prior to use. Mix ATP, SAMS peptide substrate and compound, and place them into the 384-well assay plate. Add reagent A and B based on the assay kit protocol. Incubate the assay plate at room temperature for 30 minutes after addition the mixture followed by the addition of AMPK protein (Invitrogen, CA) to initiate the AMPK phosphorylation reaction. At the same time, reactions with AMPK activator AMP in the absence of enzyme is included as blank control. The reaction fluorescence signal is monitored and recorded on Envision in kinetic mode with the excitation wavelength of 530 nm and emission wavelength of 590 nm. The $E_{30}$ value, defined as the fold of AMPK activation to phosphorylate SAMS peptide without and with an activator at the concentration of 30 µM, is calculated and analyzed using Prism 5.0.

The results are indicated in the table below.

| Example Number | E30 |
|---|---|
| Example 1 | 3.30 |
| Example-2 | 2.63 |
| Example-3 | 2.88 |
| Example-4 | 2.43 |
| Example-5 | 2.44 |
| Example-6 | 2.72 |
| Example-7 | 2.27 |
| Example-8 | 1.68 |
| Example-9 | 2.34 |
| Example-10 | 1.70 |
| Example-11 | 2.48 |
| Example-12 | 2.37 |
| Example-13 | 2.08 |
| Example-14 | 1.78 |
| Example-15 | 1.88 |
| Example-16 | 1.89 |
| Example-17 | 1.91 |
| Example-18 | 1.79 |
| Example-19 | 1.64 |
| Example-20 | 1.57 |
| Example-21 | 1.75 |
| Example-22 | 1.40 |
| Example-23 | 1.14 |
| Example-24 | 3.22 |
| Example-25 | 2.02 |
| Example-26 | 1.26 |
| Example-28 | 2.46 |
| Example-29 | 2.70 |
| Example-31 | 2.16 |
| Example-32 | 1.31 |
| Example-33 | 2.13 |
| Example-34 | 2.39 |
| Example-35 | 1.23 |
| Example-36 | 1.34 |
| Example-37 | 1.20 |
| Example-39 | 2.69 |
| Example-40 | 3.01 |
| Example-41 | 2.63 |
| Example-42 | 2.41 |
| Example-43 | 1.14 |
| Example-44 | 1.15 |
| Example-45 | 1.15 |
| Example-46 | 1.20 |
| Example-50 | 1.19 |
| Example-58 | 1.34 |

Example A

A compound of formula (I) can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
| Total | 425 mg |

Example B

A compound of formula (I) can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
| Total | 220.0 mg |

The invention claimed is:
1. A compound of formula (I)

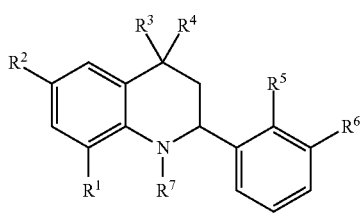

(I)

wherein
$R^1$ is selected from the group consisting of hydrogen, alkyl, haloalkyl, halogen, cyano and carboxy;
$R^2$ is selected from the group consisting of hydrogen, alkyl, haloalkyl, halogen, cyano and carboxy;
$R^3$ and $R^4$ are independently alkyl;
$R^5$ and $R^6$ are independently selected from the group consisting of hydrogen, carboxyalkylamino, carboxycycloalkylamino, alkylsulfonylamino, phenylsulfonylamino, halophenylsulfonylamino, alkylphenylsulfonylamino, phenylcarbonylamino, halophenylcarbonylamino, pyridinylsulfonylamino, alkylaminosulfonyl and halophenylaminosulfonyl;
provided that $R^5$ and $R^6$ are not both hydrogen at the same time; and
$R^7$ is hydrogen or alkyl;
or a pharmaceutically acceptable salt or ester thereof.

2. A compound according to claim 1, wherein $R^1$ is selected from the group consisting of hydrogen, alkyl, halogen and carboxy.
3. A compound according to claim 1, wherein $R^1$ is selected from the group consisting of hydrogen, methyl and chloro.
4. A compound according to claim 1, wherein $R^2$ is selected from the group consisting of haloalkyl, halogen, cyano and carboxy.
5. A compound according to claim 1, wherein $R^2$ is selected from the group consisting of trifluoromethyl, chloro, cyano and carboxy.
6. A compound according to claim 1, wherein $R^3$ and $R^4$ are both methyl at the same time.
7. A compound according to claim 1, wherein $R^5$ is selected from the group consisting of hydrogen, alkylsulfonylamino, halophenylsulfonylamino, carboxyalkylamino, carboxycycloalkylamino, halophenylcarbonylamino, pyridinylsulfonylamino and phenylsulfonylamino.
8. A compound according to claim 1, wherein $R^5$ is selected from the group consisting of hydrogen, carboxyalkylamino, halophenylsulfonylamino, pyridinylsulfonylamino and phenylsulfonylamino.
9. A compound according to claim 1, wherein $R^5$ is selected from the group consisting of hydrogen, carboxyisopropylamino, phenylsulfonylamino, fluorophenylsulfonylamino and pyridinylsulfonylamino.
10. A compound according to claim 1, wherein $R^6$ is selected from the group consisting of hydrogen, carboxyalkylamino, carboxycycloalkylamino, alkylsulfonylamino, phenylsulfonylamino, halophenylsulfonylamino, alkylphenylsulfonylamino, halophenylaminosulfonyl, pyridinylsulfonylamino and alkylaminosulfonyl.
11. A compound according to claim 1, wherein $R^6$ is selected from the group consisting of hydrogen, carboxyalkylamino and carboxycycloalkylamino.
12. A compound according to claim 1, wherein $R^6$ is selected from the group consisting of hydrogen, carboxyisopropylamino and carboxycyclopropylamino.
13. A compound according to claim 1, wherein $R^7$ is hydrogen or methyl.
14. A compound according to claim 1 selected from the group consisting of
2-[3-(6-Chloro-4,4-dimethyl-1,2,3,4-tetrahydro-quinolin-2-yl)-phenylamino]-2-methyl-propionic acid;
1-[3-(6-Chloro-4,4-dimethyl-1,2,3,4-tetrahydro-quinolin-2-yl)-phenylamino]-cyclopropanecarboxylic acid;
2-[3-(6-Cyano-4,4-dimethyl-1,2,3,4-tetrahydro-quinolin-2-yl)-phenylamino]-2-methyl-propionic acid;
1-[3-(6-Cyano-4,4-dimethyl-1,2,3,4-tetrahydro-quinolin-2-yl)-phenylamino]-cyclopropanecarboxylic acid;
2-[3-(1-Carboxy-cyclopropylamino)-phenyl]-4,4-dimethyl-1,2,3,4-tetrahydro-quinoline-8-carboxylic acid;
2-[3-(1-Carboxy-cyclopropylamino)-phenyl]-6-chloro-4,4-dimethyl-1,2,3,4-tetrahydro-quinoline-8-carboxylic acid;
2-[3-(1-Carboxy-cyclopropylamino)-phenyl]-6-chloro-4,4-dimethyl-1,2,3,4-tetrahydro-quinoline-8-carboxylic acid;
1-[3-(6-Cyano-4,4,8-trimethyl-1,2,3,4-tetrahydro-quinolin-2-yl)-phenylamino]-cyclopropanecarboxylic acid;
2-[3-(4,4-Dimethyl-6-trifluoromethyl-1,2,3,4-tetrahydro-quinolin-2-yl)-phenylamino]-2-methyl-propionic acid; and
N-[2-(6-Chloro-4,4-dimethyl-1,2,3,4-tetrahydro-quinolin-2-yl)-phenyl]-methanesulfonamide.
15. A compound according to claim 1 selected from the group consisting of 2-Methyl-2-[3-(1,4,4-trimethyl-6-trifluoromethyl-1,2,3,4-tetrahydro-quinolin-2-yl)-phenylamino]-propionic acid;

2-[3-(6-Cyano-4,4,8-trimethyl-1,2,3,4-tetrahydro-quinolin-2-yl)-phenylamino]-2-methyl-propionic acid;

1-[3-(1,4,4-Trimethyl-6-trifluoromethyl-1,2,3,4-tetrahydro-quinolin-2-yl)-phenylamino]-cyclopropanecarboxylic acid;

N-[2-(6-Chloro-4,4-dimethyl-1,2,3,4-tetrahydro-quinolin-2-yl)-phenyl]-3-fluoro-benzenesulfonamide;

2-[3-(1-Carboxy-1-methyl-ethylamino)-phenyl]-4,4-dimethyl-1,2,3,4-tetrahydro-quinoline-8-carboxylic acid;

Ethanesulfonic acid [2-(6-chloro-4,4-dimethyl-1,2,3,4-tetrahydro-quinolin-2-yl)-phenyl]-amide;

1-[3-(4,4-Dimethyl-6-trifluoromethyl-1,2,3,4-tetrahydro-quinolin-2-yl)-phenylamino]-cyclopropanecarboxylic acid;

1-[3-(8-Chloro-6-cyano-4,4-dimethyl-1,2,3,4-tetrahydro-quinolin-2-yl)-phenylamino]-cyclopropanecarboxylic acid;

N-[2-(6-Chloro-4,4-dimethyl-1,2,3,4-tetrahydro-quinolin-2-yl)-phenyl]-4-fluoro-benzenesulfonamide; and 2-[2-(6-Cyano-4,4-dimethyl-1,2,3,4-tetrahydro-quinolin-2-yl)-phenylamino]-2-methyl-propionic acid.

16. A compound according to claim 1 selected from the group consisting of N-[2-(6-Chloro-4,4-dimethyl-1,2,3,4-tetrahydro-quinolin-2-yl)-phenyl]-2-fluoro-benzenesulfonamide;

1-[2-(6-Chloro-4,4-dimethyl-1,2,3,4-tetrahydro-quinolin-2-yl)-phenylamino]-cyclopropanecarboxylic acid;

N-[2-(6-Cyano-4,4-dimethyl-1,2,3,4-tetrahydro-quinolin-2-yl)-phenyl]-methanesulfonamide;

2-[3-(6-Cyano-1,4,4-trimethyl-1,2,3,4-tetrahydro-quinolin-2-yl)-phenylamino]-2-methyl-propionic acid;

1-[2-(6-Cyano-4,4-dimethyl-1,2,3,4-tetrahydro-quinolin-2-yl)-phenylamino]-cyclopropanecarboxylic acid;

2-[2-(6-Chloro-4,4-dimethyl-1,2,3,4-tetrahydro-quinolin-2-yl)-phenylamino]-2-methyl-propionic acid;

1-[3-(6-Fluoro-4,4,8-trimethyl-1,2,3,4-tetrahydro-quinolin-2-yl)-phenylamino]-cyclopropanecarboxylic acid;

1-[3-(6-Cyano-1,4,4-trimethyl-1,2,3,4-tetrahydro-quinolin-2-yl)-phenylamino]-cyclopropanecarboxylic acid;

2-[3-(8-Chloro-6-cyano-4,4-dimethyl-1,2,3,4-tetrahydro-quinolin-2-yl)-phenylamino]-2-methyl-propionic acid; and 2-Methyl-2-[3-(4,4,6-trimethyl-1,2,3,4-tetrahydro-quinolin-2-yl)-phenylamino]-propionic acid.

17. A compound according to claim 1 selected from the group consisting of 2-[3-(6-Fluoro-4,4,8-trimethyl-1,2,3,4-tetrahydro-quinolin-2-yl)-phenylamino]-2-methyl-propionic acid;

2-[2-(4-Fluoro-benzoylamino)-phenyl]-4,4-dimethyl-1,2,3,4-tetrahydro-quinoline-6-carboxylic acid;

2-(2-Ethanesulfonylamino-phenyl)-4,4-dimethyl-1,2,3,4-tetrahydro-quinoline-6-carboxylic acid;

4,4-Dimethyl-2-[2-(pyridine-3-sulfonylamino)-phenyl]-1,2,3,4-tetrahydro-quinoline-6-carboxylic acid;

2-[2-(2-Fluoro-benzoylamino)-phenyl]-4,4-dimethyl-1,2,3,4-tetrahydro-quinoline-6-carboxylic acid;

Pyridine-3-sulfonic acid [2-(6-chloro-4,4-dimethyl-1,2,3,4-tetrahydro-quinolin-2-yl)-phenyl]-amide;

2-[2-(3-Fluoro-benzoylamino)-phenyl]-4,4-dimethyl-1,2,3,4-tetrahydro-quinoline-6-carboxylic acid;

N-[2-(6-Chloro-4,4-dimethyl-1,2,3,4-tetrahydro-quinolin-2-yl)-phenyl]-benzenesulfonamide;

2-[2-(2-Fluoro-benzenesulfonylamino)-phenyl]-4,4-dimethyl-1,2,3,4-tetrahydro-quinoline-6-carboxylic acid; and 2-[2-(4-Fluoro-benzenesulfonylamino)-phenyl]-4,4-dimethyl-1,2,3,4-tetrahydro-quinoline-6-carboxylic acid.

18. A compound according to claim 1 selected from the group consisting of 2-(2-Benzenesulfonylamino-phenyl)-4,4-dimethyl-1,2,3,4-tetrahydro-quinoline-6-carboxylic acid;

2-[2-(3-Fluoro-benzenesulfonylamino)-phenyl]-4,4-dimethyl-1,2,3,4-tetrahydro-quinoline-6-carboxylic acid;

N-[2-(4,4-Dimethyl-6-trifluoromethyl-1,2,3,4-tetrahydro-quinolin-2-yl)-phenyl]-3-fluoro-benzenesulfonamide;

N-[2-(4,4-Dimethyl-6-trifluoromethyl-1,2,3,4-tetrahydro-quinolin-2-yl)-phenyl]-2-fluoro-benzenesulfonamide;

N-[2-(4,4-Dimethyl-6-trifluoromethyl-1,2,3,4-tetrahydro-quinolin-2-yl)-phenyl]-4-fluoro-benzenesulfonamide;

Ethanesulfonic acid [2-(4,4-dimethyl-6-trifluoromethyl-1,2,3,4-tetrahydro-quinolin-2-yl)-phenyl]-amide;

N-[2-(4,4-Dimethyl-6-trifluoromethyl-1,2,3,4-tetrahydro-quinolin-2-yl)-phenyl]-benzenesulfonamide;

N-[2-(4,4-Dimethyl-6-trifluoromethyl-1,2,3,4-tetrahydro-quinolin-2-yl)-phenyl]-methanesulfonamide;

N-[2-(6-Cyano-4,4-dimethyl-1,2,3,4-tetrahydro-quinolin-2-yl)-phenyl]-benzenesulfonamide; and Propane-2-sulfonic acid [2-(6-cyano-4,4-dimethyl-1,2,3,4-tetrahydro-quinolin-2-yl)-phenyl]-amide.

19. A compound according to claim 1 selected from the group consisting of N-[2-(4,4,6-Trimethyl-1,2,3,4-tetrahydro-quinolin-2-yl)-phenyl]-benzenesulfonamide;

3-Fluoro-N-[2-(4,4,6-trimethyl-1,2,3,4-tetrahydro-quinolin-2-yl)-phenyl]-benzenesulfonamide;

N-[2-(4,4,6-Trimethyl-1,2,3,4-tetrahydro-quinolin-2-yl)-phenyl]-methanesulfonamide;

Pyridine-3-sulfonic acid [2-(6-cyano-4,4-dimethyl-1,2,3,4-tetrahydro-quinolin-2-yl)-phenyl]-amide;

Pyridine-3-sulfonic acid [2-(4,4-dimethyl-6-trifluoromethyl-1,2,3,4-tetrahydro-quinolin-2-yl)-phenyl]-amide;

Ethanesulfonic acid [3-(4,4-dimethyl-6-trifluoromethyl-1,2,3,4-tetrahydro-quinolin-2-yl)-phenyl]-amide;

N-[3-(4,4-Dimethyl-6-trifluoromethyl-1,2,3,4-tetrahydro-quinolin-2-yl)-phenyl]-benzenesulfonamide;

N-[3-(4,4-Dimethyl-6-trifluoromethyl-1,2,3,4-tetrahydro-quinolin-2-yl)-phenyl]-4-fluoro-benzenesulfonamide;

N-[3-(4,4-Dimethyl-6-trifluoromethyl-1,2,3,4-tetrahydro-quinolin-2-yl)-phenyl]-methanesulfonamide; and N-[3-(4,4-Dimethyl-6-trifluoromethyl-1,2,3,4-tetrahydro-quinolin-2-yl)-phenyl]-2-fluoro-benzenesulfonamide.

20. A compound according to claim 1 selected from the group consisting of N-[3-(4,4-Dimethyl-6-trifluoromethyl-1,2,3,4-tetrahydro-quinolin-2-yl)-phenyl]-3-fluoro-benzenesulfonamide;

Propane-2-sulfonic acid [3-(4,4-dimethyl-6-trifluoromethyl-1,2,3,4-tetrahydro-quinolin-2-yl)-phenyl]-amide;

N-[3-(4,4-Dimethyl-6-trifluoromethyl-1,2,3,4-tetrahydro-quinolin-2-yl)-phenyl]-4-methyl-benzenesulfonamide;

Pyridine-3-sulfonic acid [3-(4,4-dimethyl-6-trifluoromethyl-1,2,3,4-tetrahydro-quinolin-2-yl)-phenyl]-amide;

4-Fluoro-N-[3-(4,4,6-trimethyl-1,2,3,4-tetrahydro-quinolin-2-yl)-phenyl]-benzenesulfonamide;
2-Fluoro-N-[3-(4,4,6-trimethyl-1,2,3,4-tetrahydro-quinolin-2-yl)-phenyl]-benzenesulfonamide;
3-Fluoro-N-[3-(4,4,6-trimethyl-1,2,3,4-tetrahydro-quinolin-2-yl)-phenyl]-benzenesulfonamide;
N-[3-(4,4,6-Trimethyl-1,2,3,4-tetrahydro-quinolin-2-yl)-phenyl]-benzenesulfonamide;
4-Methyl-N-[3-(4,4,6-trimethyl-1,2,3,4-tetrahydro-quinolin-2-yl)-phenyl]-benzenesulfonamide; and
N-[3-(4,4,6-Trimethyl-1,2,3,4-tetrahydro-quinolin-2-yl)-phenyl]-methanesulfonamide.

21. A compound according to claim 1 selected from the group consisting of
Ethanesulfonic acid [3-(4,4,6-trimethyl-1,2,3,4-tetrahydro-quinolin-2-yl)-phenyl]-amide;
Pyridine-3-sulfonic acid [3-(4,4,6-trimethyl-1,2,3,4-tetrahydro-quinolin-2-yl)-phenyl]-amide;
N-[3-(6-Cyano-4,4-dimethyl-1,2,3,4-tetrahydro-quinolin-2-yl)-phenyl]-2-fluoro-benzenesulfonamide;
N-[3-(6-Cyano-4,4-dimethyl-1,2,3,4-tetrahydro-quinolin-2-yl)-phenyl]-3-fluoro-benzenesulfonamide;
N-[3-(6-Cyano-4,4-dimethyl-1,2,3,4-tetrahydro-quinolin-2-yl)-phenyl]-4-fluoro-benzenesulfonamide;
N-[3-(6-Cyano-4,4-dimethyl-1,2,3,4-tetrahydro-quinolin-2-yl)-phenyl]-benzenesulfonamide;
N-[3-(6-Cyano-4,4-dimethyl-1,2,3,4-tetrahydro-quinolin-2-yl)-phenyl]-methanesulfonamide;
Ethanesulfonic acid [3-(6-cyano-4,4-dimethyl-1,2,3,4-tetrahydro-quinolin-2-yl)-phenyl]-amide;
Propane-2-sulfonic acid [3-(6-cyano-4,4-dimethyl-1,2,3,4-tetrahydro-quinolin-2-yl)-phenyl]-amide; and
N-[3-(6-Cyano-4,4-dimethyl-1,2,3,4-tetrahydro-quinolin-2-yl)-phenyl]-4-methyl-benzenesulfonamide.

22. A compound according to claim 1 selected from the group consisting of
Pyridine-3-sulfonic acid [3-(6-cyano-4,4-dimethyl-1,2,3,4-tetrahydro-quinolin-2-yl)-phenyl]-amide;
N-[3-(6-Chloro-4,4-dimethyl-1,2,3,4-tetrahydro-quinolin-2-yl)-phenyl]-4-fluoro-benzenesulfonamide;
N-[3-(6-Chloro-4,4-dimethyl-1,2,3,4-tetrahydro-quinolin-2-yl)-phenyl]-2-fluoro-benzenesulfonamide;
N-[3-(6-Chloro-4,4-dimethyl-1,2,3,4-tetrahydro-quinolin-2-yl)-phenyl]-4-methyl-benzenesulfonamide;
N-[3-(6-Chloro-4,4-dimethyl-1,2,3,4-tetrahydro-quinolin-2-yl)-phenyl]-benzenesulfonamide;
N-[3-(6-Chloro-4,4-dimethyl-1,2,3,4-tetrahydro-quinolin-2-yl)-phenyl]-3-fluoro-benzenesulfonamide;
N-[3-(6-Chloro-4,4-dimethyl-1,2,3,4-tetrahydro-quinolin-2-yl)-phenyl]-methanesulfonamide;
3-(6-Chloro-4,4-dimethyl-1,2,3,4-tetrahydro-quinolin-2-yl)-N-methyl-benzenesulfonamide;
Ethanesulfonic acid [3-(6-chloro-4,4-dimethyl-1,2,3,4-tetrahydro-quinolin-2-yl)-phenyl]-amide;
3-(6-Chloro-4,4-dimethyl-1,2,3,4-tetrahydro-quinolin-2-yl)-N-(4-fluoro-phenyl)-benzenesulfonamide; and
Pyridine-3-sulfonic acid [3-(6-chloro-4,4-dimethyl-1,2,3,4-tetrahydro-quinolin-2-yl)-phenyl]-amide.

23. A compound according to claim 1 selected from the group consisting of
2-[3-(6-Chloro-4,4-dimethyl-1,2,3,4-tetrahydro-quinolin-2-yl)-phenylamino]-2-methyl-propionic acid;
1-[3-(6-Chloro-4,4-dimethyl-1,2,3,4-tetrahydro-quinolin-2-yl)-phenylamino]-cyclopropanecarboxylic acid;
2-[3-(6-Cyano-4,4-dimethyl-1,2,3,4-tetrahydro-quinolin-2-yl)-phenylamino]-2-methyl-propionic acid;
2-Methyl-2-[3-(1,4,4-trimethyl-6-trifluoromethyl-1,2,3,4-tetrahydro-quinolin-2-yl)-phenylamino]-propionic acid;
2-[3-(6-Cyano-4,4,8-trimethyl-1,2,3,4-tetrahydro-quinolin-2-yl)-phenylamino]-2-methyl-propionic acid;
2-[2-(6-Cyano-4,4-dimethyl-1,2,3,4-tetrahydro-quinolin-2-yl)-phenylamino]-2-methyl-propionic acid;
N-[2-(6-Chloro-4,4-dimethyl-1,2,3,4-tetrahydro-quinolin-2-yl)-phenyl]-2-fluoro-benzenesulfonamide;
2-[3-(6-Cyano-1,4,4-trimethyl-1,2,3,4-tetrahydro-quinolin-2-yl)-phenylamino]-2-methyl-propionic acid;
1-[3-(6-Cyano-1,4,4-trimethyl-1,2,3,4-tetrahydro-quinolin-2-yl)-phenylamino]-cyclopropanecarboxylic acid;
2-[3-(8-Chloro-6-cyano-4,4-dimethyl-1,2,3,4-tetrahydro-quinolin-2-yl)-phenylamino]-2-methyl-propionic acid;
4,4-Dimethyl-2-[2-(pyridine-3-sulfonylamino)-phenyl]-1,2,3,4-tetrahydro-quinoline-6-carboxylic acid;
2-[2-(2-Fluoro-benzenesulfonylamino)-phenyl]-4,4-dimethyl-1,2,3,4-tetrahydro-quinoline-6-carboxylic acid;
2-[2-(4-Fluoro-benzenesulfonylamino)-phenyl]-4,4-dimethyl-1,2,3,4-tetrahydro-quinoline-6-carboxylic acid;
2-(2-Benzenesulfonylamino-phenyl)-4,4-dimethyl-1,2,3,4-tetrahydro-quinoline-6-carboxylic acid; and
2-[2-(3-Fluoro-benzenesulfonylamino)-phenyl]-4,4-dimethyl-1,2,3,4-tetrahydro-quinoline-6-carboxylic acid.

24. A pharmaceutical composition comprising a compound according to claim 1 and a therapeutically inert carrier.

* * * * *